US011278346B2

United States Patent
Messerly et al.

(10) Patent No.: US 11,278,346 B2
(45) Date of Patent: Mar. 22, 2022

(54) SYSTEMS AND METHODS OF DISPLAYING SURGICAL INSTRUMENT STATUS

(71) Applicant: Cilag GmbH International, Zug (CH)

(72) Inventors: Jeffrey D. Messerly, Cincinnati, OH (US); David C. Yates, Morrow, OH (US); Mark A. Davison, Maineville, OH (US); Jason L. Harris, Lebanon, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 103 days.

(21) Appl. No.: 15/636,103

(22) Filed: Jun. 28, 2017

(65) Prior Publication Data
US 2019/0000533 A1   Jan. 3, 2019

(51) Int. Cl.
*A61B 18/14*   (2006.01)
*A61B 18/12*   (2006.01)
(Continued)

(52) U.S. Cl.
CPC .... *A61B 18/1445* (2013.01); *A61B 17/07207* (2013.01); *A61B 17/282* (2013.01); *A61B 18/1206* (2013.01); *A61B 17/295* (2013.01); *A61B 2017/00026* (2013.01); *A61B 2017/0046* (2013.01); *A61B 2017/00075* (2013.01); *A61B 2017/00119* (2013.01); *A61B 2017/00128* (2013.01); *A61B 2017/00398* (2013.01); *A61B 2017/00734* (2013.01); *A61B 2017/07214* (2013.01); *A61B 2017/07257* (2013.01); *A61B 2017/07271* (2013.01); *A61B 2017/07278* (2013.01); *A61B 2017/07285* (2013.01);
(Continued)

(58) Field of Classification Search
CPC ............ A61B 18/1445; A61B 18/1206; A61B 17/07207; A61B 17/282; G06T 11/206; G06T 2210/41
See application file for complete search history.

(56) References Cited

U.S. PATENT DOCUMENTS

| 2,961,385 A | 11/1960 | McGall |
| 3,370,263 A | 2/1968 | Schreieck |

(Continued)

FOREIGN PATENT DOCUMENTS

| GB | 1526401 A | 9/1978 |
| JP | 2004130126 A | 4/2004 |
| WO | WO-9937225 A1 | 7/1999 |

OTHER PUBLICATIONS

Bay Area Circuits (https://bayareacircuits.com/multi-layer-stackups/) (Year: 2015).

*Primary Examiner* — Tigist S Demie

(57) ABSTRACT

A surgical instrument is disclosed. The surgical instrument includes a circuit configured to deliver RF energy to a cartridge disposed in an end effector configured to receive the cartridge, a closure mechanism configured to transition the end effector between an open position and a closed position, a display, and a control circuit operably coupled to the display. The control circuit configured to determine an amount of RF energy delivered to a tissue through the cartridge, display the amount of RF energy on the display, determine a position of the closure mechanism, and display the position of the closure mechanism on the display.

19 Claims, 29 Drawing Sheets

(51) Int. Cl.
*A61B 18/00* (2006.01)
*A61B 17/00* (2006.01)
*A61B 17/072* (2006.01)
*A61B 17/28* (2006.01)
*A61B 90/00* (2016.01)
*A61B 17/29* (2006.01)
*A61B 17/295* (2006.01)
*G06T 11/20* (2006.01)

(52) U.S. Cl.
CPC .......... *A61B 2017/2845* (2013.01); *A61B 2017/2926* (2013.01); *A61B 2017/2927* (2013.01); *A61B 2018/0063* (2013.01); *A61B 2018/00589* (2013.01); *A61B 2018/00702* (2013.01); *A61B 2018/00779* (2013.01); *A61B 2018/00875* (2013.01); *A61B 2018/00916* (2013.01); *A61B 2018/00922* (2013.01); *A61B 2018/00988* (2013.01); *A61B 2018/1452* (2013.01); *A61B 2018/1455* (2013.01); *A61B 2090/0808* (2016.02); *A61B 2090/0811* (2016.02); *G06T 11/206* (2013.01); *G06T 2210/41* (2013.01)

(56) References Cited

U.S. PATENT DOCUMENTS

| | | |
|---|---|---|
| D278,081 S | 3/1985 | Green |
| D297,764 S | 9/1988 | Hunt et al. |
| 5,007,907 A | 4/1991 | Nishigaki et al. |
| 5,364,395 A | 11/1994 | West, Jr. |
| 5,403,312 A | 4/1995 | Yates et al. |
| D360,688 S | 7/1995 | Ferragamo et al. |
| 5,485,947 A | 1/1996 | Olson et al. |
| 5,658,281 A | 8/1997 | Heard |
| 5,673,842 A | 10/1997 | Bittner et al. |
| 5,735,848 A | 4/1998 | Yates et al. |
| 5,817,093 A | 10/1998 | Williamson, IV et al. |
| 5,827,279 A | 10/1998 | Hughett et al. |
| 5,833,690 A | 11/1998 | Yates et al. |
| 5,835,829 A | 11/1998 | Genovese et al. |
| 6,004,320 A | 12/1999 | Casscells et al. |
| D480,808 S | 10/2003 | Wells et al. |
| 6,730,081 B1 | 5/2004 | Desai |
| 6,905,497 B2 | 6/2005 | Truckai et al. |
| 6,918,906 B2 | 7/2005 | Long |
| D509,297 S | 9/2005 | Wells |
| 6,988,649 B2 | 1/2006 | Shelton, IV et al. |
| 7,044,352 B2 | 5/2006 | Shelton, IV et al. |
| 7,223,267 B2 | 5/2007 | Isola et al. |
| 7,383,611 B2 | 6/2008 | Foster |
| D576,278 S | 9/2008 | Nalagatla et al. |
| 7,431,720 B2 | 10/2008 | Pendekanti et al. |
| 7,476,222 B2 | 1/2009 | Sun et al. |
| 7,517,356 B2 | 4/2009 | Heinrich |
| 7,559,452 B2 | 7/2009 | Wales et al. |
| 7,575,144 B2 | 8/2009 | Ortiz et al. |
| 7,617,961 B2 | 11/2009 | Viola |
| D605,762 S | 12/2009 | Nalagatla et al. |
| 7,673,781 B2 | 3/2010 | Swayze et al. |
| 7,722,607 B2 | 5/2010 | Dumbauld et al. |
| 7,780,663 B2 | 8/2010 | Yates et al. |
| 7,819,296 B2 | 10/2010 | Hueil et al. |
| 7,861,906 B2 | 1/2011 | Doll et al. |
| 7,896,877 B2 | 3/2011 | Hall et al. |
| 7,953,823 B2 | 5/2011 | Rider et al. |
| D650,074 S | 12/2011 | Hunt et al. |
| 8,277,446 B2 | 10/2012 | Heard |
| 8,453,906 B2 | 6/2013 | Huang et al. |
| 8,465,534 B2 | 6/2013 | Schechter |
| 8,485,413 B2 | 7/2013 | Scheib et al. |
| 8,517,239 B2 | 8/2013 | Scheib et al. |
| 8,523,043 B2 | 9/2013 | Ullrich et al. |
| 8,573,461 B2 | 11/2013 | Shelton, IV et al. |
| 8,579,176 B2 | 11/2013 | Smith et al. |
| 8,608,045 B2 | 12/2013 | Smith et al. |
| 8,616,431 B2 | 12/2013 | Timm et al. |
| 8,622,274 B2 | 1/2014 | Yates et al. |
| 8,636,736 B2 | 1/2014 | Yates et al. |
| 8,663,222 B2 | 3/2014 | Anderson et al. |
| 8,708,213 B2 | 4/2014 | Shelton, IV et al. |
| 8,764,747 B2 | 7/2014 | Cummings et al. |
| 8,784,415 B2 | 7/2014 | Malackowski et al. |
| 8,858,547 B2 | 10/2014 | Brogna |
| 8,876,858 B2 | 11/2014 | Braun |
| 8,888,771 B2 | 11/2014 | Twomey |
| 8,888,776 B2 | 11/2014 | Dietz et al. |
| 8,926,607 B2 | 1/2015 | Norvell et al. |
| 8,968,317 B2 | 3/2015 | Evans et al. |
| 8,979,890 B2 | 3/2015 | Boudreaux |
| 8,998,060 B2 | 4/2015 | Bruewer et al. |
| 9,005,199 B2 | 4/2015 | Beckman et al. |
| 9,060,775 B2 | 6/2015 | Wiener et al. |
| 9,072,535 B2 | 7/2015 | Shelton, IV et al. |
| 9,149,325 B2 | 10/2015 | Worrell et al. |
| 9,161,802 B2 | 10/2015 | Przybyszewski |
| 9,161,803 B2 | 10/2015 | Yates et al. |
| 9,345,481 B2 | 5/2016 | Hall et al. |
| 9,358,003 B2 | 6/2016 | Hall et al. |
| 9,402,627 B2 | 8/2016 | Stevenson et al. |
| 9,510,906 B2 | 12/2016 | Boudreaux et al. |
| 9,526,564 B2 | 12/2016 | Rusin |
| 9,549,733 B2 | 1/2017 | Knodel |
| 9,561,031 B2 | 2/2017 | Heinrich et al. |
| 9,566,062 B2 | 2/2017 | Boudreaux |
| 9,572,622 B2 | 2/2017 | Shelton, IV et al. |
| 9,585,657 B2 | 3/2017 | Shelton, IV et al. |
| 9,629,627 B2 | 4/2017 | Kostrzewski et al. |
| 9,629,628 B2 | 4/2017 | Aranyi |
| 9,700,309 B2 | 7/2017 | Jaworek et al. |
| 9,706,993 B2 | 7/2017 | Hessler et al. |
| 9,707,028 B2 | 7/2017 | Batchelor et al. |
| 9,724,095 B2 | 8/2017 | Gupta et al. |
| 9,743,929 B2 | 8/2017 | Leimbach et al. |
| 9,757,142 B2 | 9/2017 | Shimizu |
| D800,904 S | 10/2017 | Leimbach et al. |
| 9,788,835 B2 | 10/2017 | Morgan et al. |
| 9,795,379 B2 | 10/2017 | Leimbach et al. |
| 9,808,246 B2 | 11/2017 | Shelton, IV et al. |
| 9,814,514 B2 | 11/2017 | Shelton, IV et al. |
| 9,839,421 B2 | 12/2017 | Zerkle et al. |
| 9,844,375 B2 | 12/2017 | Overmyer et al. |
| 9,877,722 B2 | 1/2018 | Schellin et al. |
| D809,659 S | 2/2018 | Menn |
| 9,888,958 B2 | 2/2018 | Evans et al. |
| 9,924,942 B2 | 3/2018 | Swayze et al. |
| 9,924,944 B2 | 3/2018 | Shelton, IV et al. |
| 9,924,998 B2 | 3/2018 | Martin et al. |
| 9,968,355 B2 | 5/2018 | Shelton, IV et al. |
| 9,980,769 B2 | 5/2018 | Trees et al. |
| 10,010,366 B2 | 7/2018 | Strobl |
| 10,016,186 B2 | 7/2018 | Benn |
| 10,052,100 B2 | 8/2018 | Morgan et al. |
| D831,209 S | 10/2018 | Huitema et al. |
| D836,198 S | 12/2018 | Harris et al. |
| 10,178,992 B2 | 1/2019 | Wise et al. |
| 10,194,912 B2 | 2/2019 | Scheib et al. |
| 10,201,348 B2 | 2/2019 | Scheib et al. |
| 10,211,586 B2 | 2/2019 | Adams et al. |
| 10,213,198 B2 | 2/2019 | Aronhalt et al. |
| 10,231,776 B2 | 3/2019 | Artale et al. |
| 10,238,385 B2 | 3/2019 | Yates et al. |
| 10,245,027 B2 | 4/2019 | Shelton, IV et al. |
| 10,265,120 B2 | 4/2019 | Yates et al. |
| D847,989 S | 5/2019 | Shelton, IV et al. |
| D850,617 S | 6/2019 | Shelton, IV et al. |
| 10,327,776 B2 | 6/2019 | Harris et al. |
| 10,335,147 B2 | 7/2019 | Rector et al. |
| 10,357,305 B2 | 7/2019 | Esch et al. |
| D865,175 S | 10/2019 | Widenhouse et al. |
| 10,456,137 B2 | 10/2019 | Vendely et al. |
| 10,485,567 B2 | 11/2019 | Piskun |
| 10,548,504 B2 | 2/2020 | Shelton, IV et al. |

(56) References Cited

U.S. PATENT DOCUMENTS

| | | |
|---|---|---|
| 10,603,117 B2 | 3/2020 | Schings et al. |
| 10,610,289 B2 | 4/2020 | Jensen |
| 10,617,412 B2 | 4/2020 | Shelton, IV et al. |
| 10,716,614 B2 | 7/2020 | Yates et al. |
| D893,717 S | 8/2020 | Messerly et al. |
| D908,216 S | 1/2021 | Messerly et al. |
| 10,903,685 B2 | 1/2021 | Yates et al. |
| 2004/0122423 A1 | 6/2004 | Dycus et al. |
| 2005/0203504 A1* | 9/2005 | Wham ............... A61B 18/1442 606/34 |
| 2006/0064086 A1 | 3/2006 | Odom |
| 2007/0102472 A1 | 5/2007 | Shelton |
| 2008/0147062 A1 | 6/2008 | Truckai et al. |
| 2009/0206133 A1 | 8/2009 | Morgan et al. |
| 2010/0193566 A1 | 8/2010 | Scheib et al. |
| 2010/0228250 A1 | 9/2010 | Brogna |
| 2010/0294829 A1* | 11/2010 | Giordano ............. A61B 17/068 227/176.1 |
| 2011/0028964 A1 | 2/2011 | Edwards |
| 2011/0087217 A1* | 4/2011 | Yates ................ A61B 18/1206 606/39 |
| 2011/0106076 A1 | 5/2011 | Hernandez Zendejas |
| 2011/0125176 A1 | 5/2011 | Yates et al. |
| 2011/0174862 A1* | 7/2011 | Shelton, IV ..... A61B 17/07207 227/176.1 |
| 2012/0016413 A1 | 1/2012 | Timm et al. |
| 2012/0041436 A1* | 2/2012 | Ullrich ................... A61B 18/12 606/39 |
| 2012/0181322 A1* | 7/2012 | Whitman ......... A61B 17/07207 227/176.1 |
| 2012/0245576 A1* | 9/2012 | Epstein .............. A61B 18/1477 606/33 |
| 2014/0005654 A1* | 1/2014 | Batross .......... A61B 17/320092 606/33 |
| 2014/0263541 A1 | 9/2014 | Leimbach et al. |
| 2014/0263552 A1 | 9/2014 | Hall et al. |
| 2015/0060519 A1* | 3/2015 | Swayze ................ A61B 17/072 227/175.3 |
| 2015/0080876 A1 | 3/2015 | Worrell et al. |
| 2015/0080887 A1 | 3/2015 | Sobajima et al. |
| 2015/0272575 A1* | 10/2015 | Leimbach ............ A61B 17/072 227/175.3 |
| 2015/0297235 A1 | 10/2015 | Harris et al. |
| 2016/0066913 A1 | 3/2016 | Swayze et al. |
| 2016/0066916 A1* | 3/2016 | Overmyer ............ A61B 17/105 227/176.1 |
| 2016/0120545 A1 | 5/2016 | Shelton, IV et al. |
| 2016/0270842 A1 | 9/2016 | Strobl et al. |
| 2017/0105782 A1 | 4/2017 | Scheib et al. |
| 2017/0105786 A1 | 4/2017 | Scheib et al. |
| 2017/0119388 A1 | 5/2017 | Kostrzewski |
| 2017/0143336 A1 | 5/2017 | Shah et al. |
| 2017/0224330 A1 | 8/2017 | Worthington et al. |
| 2017/0296213 A1 | 10/2017 | Swensgard et al. |
| 2017/0312019 A1 | 11/2017 | Trees et al. |
| 2018/0168621 A1 | 6/2018 | Shelton, IV et al. |
| 2018/0168650 A1 | 6/2018 | Shelton, IV et al. |
| 2018/0360452 A1 | 12/2018 | Shelton, IV et al. |
| 2019/0000463 A1 | 1/2019 | Shelton, IV et al. |
| 2019/0000464 A1 | 1/2019 | Shelton, IV et al. |
| 2019/0000468 A1 | 1/2019 | Adams et al. |
| 2019/0000470 A1 | 1/2019 | Yates et al. |
| 2019/0000472 A1 | 1/2019 | Shelton, IV et al. |
| 2019/0000478 A1 | 1/2019 | Messerly et al. |
| 2019/0000479 A1 | 1/2019 | Harris et al. |
| 2019/0000525 A1 | 1/2019 | Messerly et al. |
| 2019/0000531 A1 | 1/2019 | Messerly et al. |
| 2019/0000532 A1 | 1/2019 | Shelton, IV et al. |
| 2019/0000534 A1 | 1/2019 | Messerly et al. |
| 2019/0000535 A1 | 1/2019 | Messerly et al. |
| 2019/0000537 A1 | 1/2019 | Widenhouse et al. |
| 2019/0000538 A1 | 1/2019 | Widenhouse et al. |
| 2019/0000539 A1 | 1/2019 | Messerly et al. |
| 2020/0397432 A1 | 12/2020 | Messerly et al. |
| 2021/0068891 A1 | 3/2021 | Messerly et al. |
| 2021/0093322 A1 | 4/2021 | Adams et al. |

* cited by examiner

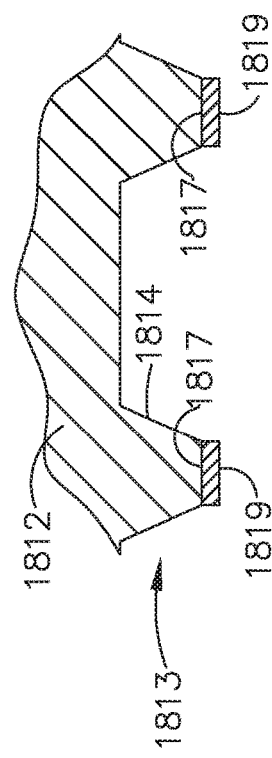
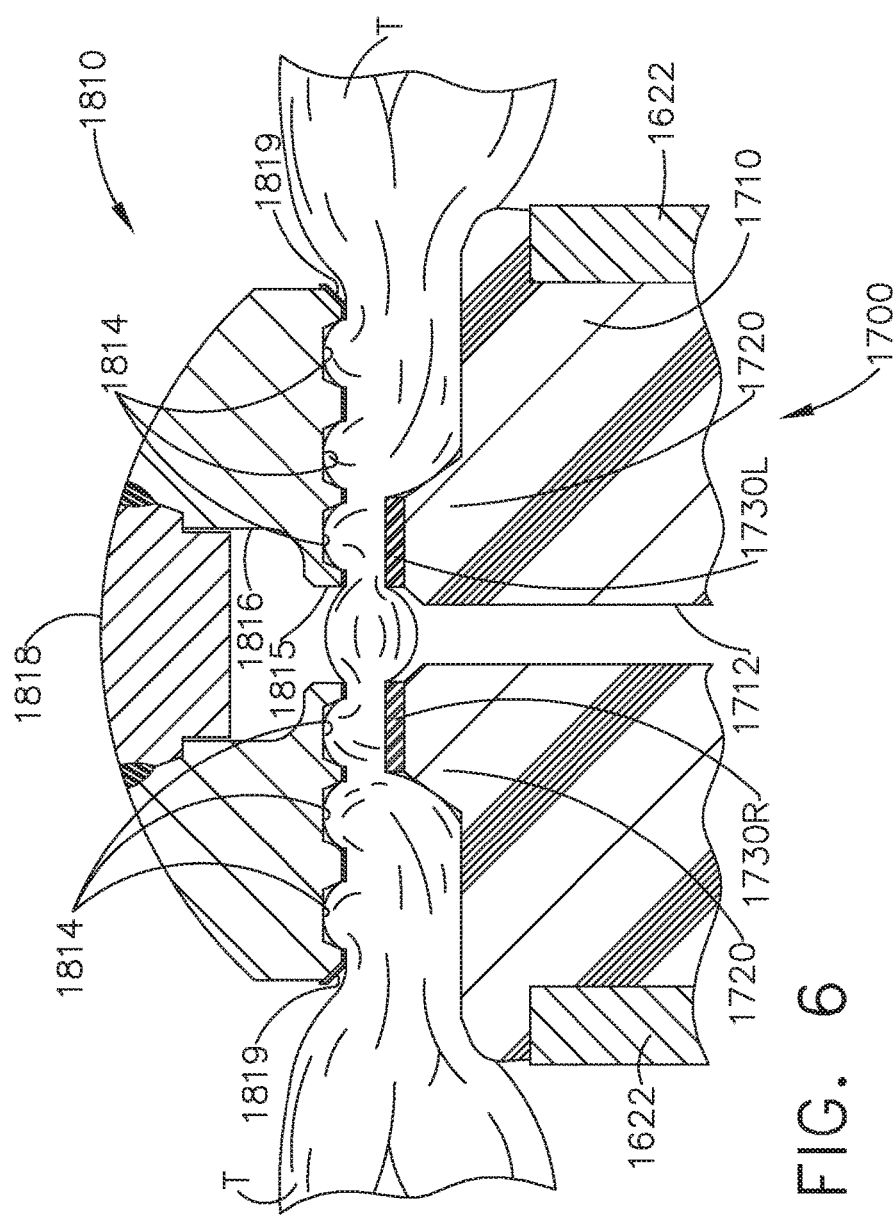
FIG. 7
FIG. 6

SYSTEMS AND METHODS OF DISPLAYING SURGICAL INSTRUMENT STATUS

TECHNICAL FIELD

The present disclosure relates to surgical instruments and, in various circumstances, surgical sealing and cutting instruments and staple cartridges therefor that are designed to seal and cut tissue.

BACKGROUND

In a surgical sealing and stapling instrument, it may be useful to display a variety of information captured by the sensors of the surgical instrument to the operator so that the operator can ensure that the instrument is functioning properly or take corrective action if unexpected tissue conditions are being encountered or if the instrument is not functioning properly.

SUMMARY

In one aspect, a surgical instrument is provided. The surgical instrument comprises a circuit configured to deliver RF energy to a cartridge disposed in an end effector configured to receive the cartridge; a closure mechanism configured to transition the end effector between an open position and a closed position; a display; and a control circuit operably coupled to the display, the control circuit configured to: determine an amount of RF energy delivered to a tissue through the cartridge; display the amount of RF energy on the display; determine a position of the closure mechanism; and display the position of the closure mechanism on the display.

In another aspect, the surgical instrument comprises a circuit configured to deliver RF energy to a cartridge disposed in an end effector; a closure mechanism configured to transition the end effector between an open position and a closed position; a display; and a processor operably coupled to the display; a memory operably coupled to the processor, the memory storing program instructions that, when executed by the processor, cause the processor to: determine a status of RF energy delivered to a tissue through the cartridge; display the status of RF energy; determine a status of the closure mechanism; and display the status of the closure mechanism.

In another aspect, a method of controlling a display in a surgical instrument is provided. The surgical instrument comprises a circuit configured to deliver RF energy to a cartridge disposed within an end effector configured to receive the cartridge, a closure mechanism configured to transition the end effector between an open position and a closed position, a display, and a control circuit coupled to the display. The method comprises determining, by the control circuit, an amount of RF energy applied to a tissue through the cartridge; displaying, by the control circuit, the amount of RF energy on the display; determining, by the control circuit, a position of the closure mechanism; and displaying, by the control circuit, the position of the closure mechanism on the display.

FIGURES

The novel features of the aspects described herein are set forth with particularity in the appended claims. These aspects, however, both as to organization and methods of operation may be better understood by reference to the following description, taken in conjunction with the accompanying drawings.

FIG. 6 is a partial cross-sectional view of the end effector depicted in FIGS. 1-5 supporting an RF cartridge therein and with tissue clamped between the cartridge and the anvil according to one aspect of this disclosure.

FIG. 7 is a partial cross-sectional view of the anvil of FIG. 6 according to one aspect of this disclosure.

DESCRIPTION

Figure 1:
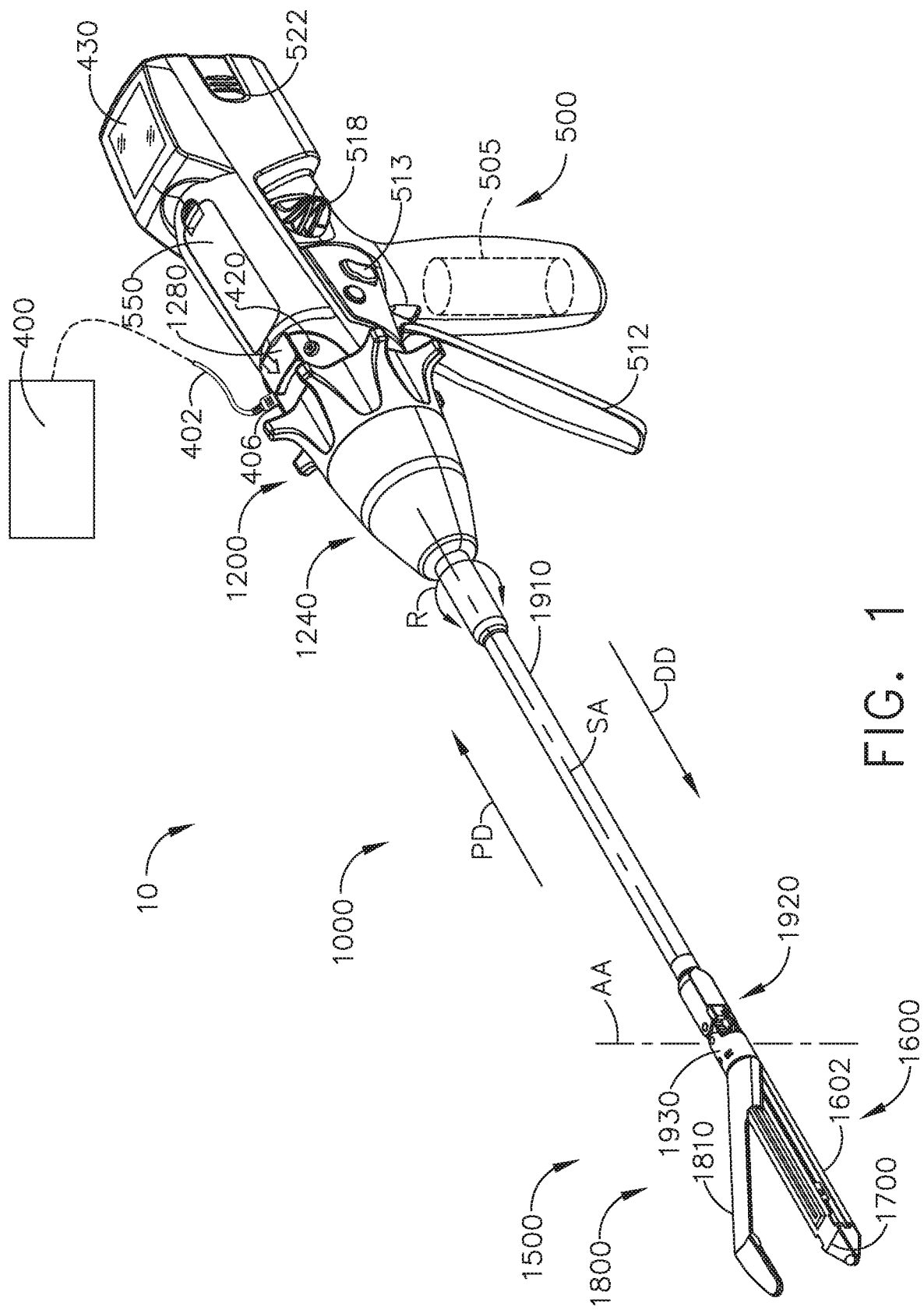
FIG. 1 is a perspective view of a surgical system including a handle assembly coupled to an interchangeable surgical tool assembly that is configured to be used in connection with conventional surgical staple/fastener cartridges and radio frequency (RF) cartridges according to one aspect of this disclosure.

Applicant of the present application owns the following patent applications filed Jun. 28, 2017 and which are each herein incorporated by reference in their respective entireties:

U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, by inventors Jeffrey D. Messerly et al., filed Jun. 28, 2017.

U.S. patent application Ser. No. 15/636,110, titled SHAFT MODULE CIRCUITRY ARRANGEMENTS, by inventors Jeffrey D. Messerly et al., filed Jun. 28, 2017.

U.S. patent application Ser. No. 15/636,116, titled SYSTEMS AND METHODS FOR CONTROLLING CONTROL CIRCUITS FOR INDEPENDENT ENERGY DELIVERY OVER SEGMENTED SECTIONS, by inventors Jeffrey D. Messerly et al., filed Jun. 28, 2017.

U.S. patent application Ser. No. 15/636,123, titled FLEXIBLE CIRCUIT ARRANGEMENT FOR SURGICAL FASTENING INSTRUMENTS, by inventors Jeffrey D. Messerly et al., filed Jun. 28, 2017.

U.S. patent application Ser. No. 15/636,134, titled SURGICAL SYSTEM COUPLEABLE WITH STAPLE CARTRIDGE AND RADIO FREQUENCY CARTRIDGE, AND HAVING A PLURALITY OF RADIO-FREQUENCY ENERGY RETURN PATHS, by inventors Jeffrey D. Messerly et al., filed Jun. 28, 2017.

U.S. patent application Ser. No. 15/636,144, titled SYSTEMS AND METHODS FOR CONTROLLING CONTROL CIRCUITS FOR AN INDEPENDENT ENERGY DELIVERY OVER SEGMENTED SECTIONS, by inventors David C. Yates et al., filed Jun. 28, 2017.

U.S. patent application Serial No. 15/636,150, titled SURGICAL END EFFECTOR FOR APPLYING ELECTROSURGICAL ENERGY TO DIFFERENT ELECTRODES ON DIFFERENT TIME PERIODS, by inventors Tamara Widenhouse et al., filed Jun. 28, 2017.

U.S. patent application Ser. No. 15/636,162, titled ELECTROSURGICAL CARTRIDGE FOR USE IN THIN PROFILE SURGICAL CUTTING AND STAPLING INSTRUMENT, by inventors Tamara Widenhouse et al., filed Jun. 28, 2017.

U.S. patent application Ser. No. 15/636,169, titled SURGICAL END EFFECTOR TO ADJUST JAW COMPRESSION, by inventors Frederick E. Shelton, IV et al., filed Jun. 28, 2017.

U.S. patent application Ser. No. 15/636,177, titled CARTRIDGE ARRANGEMENTS FOR SURGICAL CUTTING AND FASTENING INSTRUMENTS WITH LOCKOUT DISABLEMENT FEATURES, by inventors Jason L. Harris et al., filed Jun. 28, 2017.

U.S. patent application Ser. No. 15/636,180, titled SURGICAL CUTTING AND FASTENING INSTRUMENTS WITH DUAL POWER SOURCES, by inventors Jeffrey D. Messerly et al., filed Jun. 28, 2017.

Electrosurgical devices may be used in many surgical operations. Electrosurgical devices may apply electrical energy to tissue in order to treat tissue. An electrosurgical device may comprise an instrument having a distally mounted end effector comprising one or more electrodes. The end effector can be positioned against tissue such that electrical current may be introduced into the tissue. Electrosurgical devices can be configured for monopolar or bipolar operation. During monopolar operation, current may be introduced into the tissue by an active (or source) electrode on the end effector and returned through a return electrode. The return electrode may be a grounding pad and separately located on a patient's body. During bipolar operation, current may be introduced into and returned from the tissue by the active and return electrodes, respectively, of the end effector.

The end effector may include two or more jaw members. At least one of the jaw members may have at least one electrode. At least one jaw may be moveable from a position spaced apart from the opposing jaw for receiving tissues to a position in which the space between the jaw members is less than that of the first position. This movement of the moveable jaw may compress the tissue held between. Heat generated by the current flow through the tissue in combination with the compression achieved by the jaw's movement may form hemostatic seals within the tissue and/or between tissues and, thus, may be particularly useful for sealing blood vessels, for example. The end effector may comprise a cutting member. The cutting member may be movable relative to the tissue and the electrodes to transect the tissue.

Electrosurgical devices also may include mechanisms to clamp tissue together, such as a stapling device, and/or mechanisms to sever tissue, such as a tissue knife. An electrosurgical device may include a shaft for placing the end effector proximate to tissue undergoing treatment. The shaft may be straight or curved, bendable or non-bendable. In an electrosurgical device including a straight and bendable shaft, the shaft may have one or more articulation joints to permit controlled bending of the shaft. Such joints may permit a user of the electrosurgical device to place the end effector in contact with tissue at an angle to the shaft when the tissue being treated is not readily accessible using an electrosurgical device having a straight, non-bending shaft.

Electrical energy applied by electrosurgical devices can be transmitted to the instrument by a generator in communication with the hand piece. The electrical energy may be in the form of radio frequency ("RF") energy. RF energy is a form of electrical energy that may be in the frequency range of 200 kilohertz (kHz) to 1 megahertz (MHz). In application, an electrosurgical instrument can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

The RF energy may be in a frequency range described in EN 60601-2-2:2009+A11:2011, Definition 201.3.218—HIGH FREQUENCY. For example, the frequency in monopolar RF applications may be typically restricted to less than 5 MHz. However, in bipolar RF applications, the frequency can be almost anything. Frequencies above 200 kHz can be typically used for monopolar applications in order to avoid the unwanted stimulation of nerves and muscles that would result from the use of low frequency current. Lower frequencies may be used for bipolar applications if the risk analysis shows the possibility of neuromuscular stimulation has been mitigated to an acceptable level. Normally, frequencies above 5 MHz are not used in order to minimize the problems associated with high frequency leakage currents. Higher frequencies may, however, be used in the case of bipolar applications. It is generally recognized that 10 mA is the lower threshold of thermal effects on tissue.

Figure 2:
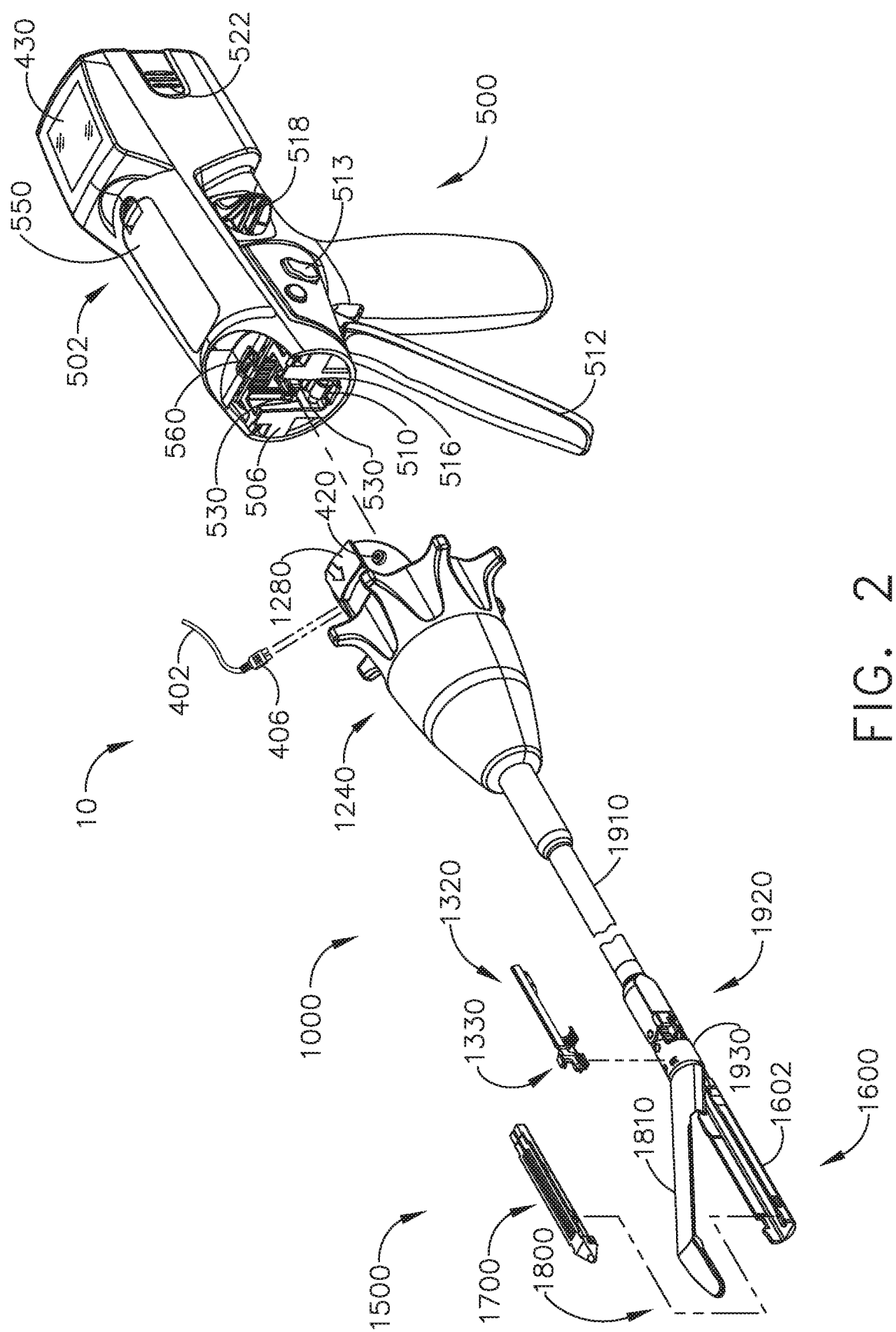
FIG. 2 is an exploded perspective assembly view of the surgical system of FIG. 1 according to one aspect of this disclosure.

FIGS. 1 and 2 depict a motor-driven surgical system 10 that may be used to perform a variety of different surgical procedures. In the illustrated arrangement, the surgical system 10 comprises an interchangeable surgical tool assembly 1000 that is operably coupled to a handle assembly 500. In another surgical system aspect, the interchangeable surgical tool assembly 1000 may also be effectively employed with a tool drive assembly of a robotically controlled or automated surgical system. For example, the surgical tool assembly 1000 disclosed herein may be employed with various robotic systems, instruments, components and methods such as, but not limited to, those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety.

In the illustrated aspect, the handle assembly 500 may comprise a handle housing 502 that includes a pistol grip portion 504 that can be gripped and manipulated by the clinician. As will be briefly discussed below, the handle assembly 500 operably supports a plurality of drive systems that are configured to generate and apply various control motions to corresponding portions of the interchangeable surgical tool assembly 1000. As shown in FIG. 2, the handle assembly 500 may further include a handle frame 506 that operably supports the plurality of drive systems. For example, the handle frame 506 can operably support a "first" or closure drive system, generally designated as 510, which may be employed to apply closing and opening motions to the interchangeable surgical tool assembly 1000. In at least one form, the closure drive system 510 may include an actuator in the form of a closure trigger 512 that is pivotally supported by the handle frame 506. Such arrangement enables the closure trigger 512 to be manipulated by a clinician such that when the clinician grips the pistol grip portion 504 of the handle assembly 500, the closure trigger 512 may be easily pivoted from a starting or "unactuated" position to an "actuated" position and more particularly to a fully compressed or fully actuated position. In use, to actuate the closure drive system 510, the clinician depresses the closure trigger 512 towards the pistol grip portion 504. As described in further detail in U.S. patent application Ser. No. 14/226,142, entitled SURGICAL INSTRUMENT COMPRISING A SENSOR SYSTEM, now U.S. Patent Application Publication No. 2015/0272575, which is hereby incorporated by reference in its entirety herein, when the clinician fully depresses the closure trigger 512 to attain the full closure stroke, the closure drive system 510 is configured to lock the closure trigger 512 into the fully depressed or fully actuated position. When the clinician desires to unlock the closure trigger 512 to permit it to be biased to the unactuated position, the clinician simply activates a closure release button assembly 518 which enables the closure trigger to return to unactuated position. The closure release button assembly 518 may also be configured to interact with various sensors that communicate with a microcontroller in the handle assembly 500 for tracking the position of the closure trigger 512. Further details concerning the configuration and operation of the closure release button assembly 518 may be found in U.S. Patent Application Publication No. 2015/0272575.

In at least one form, the handle assembly 500 and the handle frame 506 may operably support another drive system referred to herein as a firing drive system 530 that is configured to apply firing motions to corresponding portions of the interchangeable surgical tool assembly that is attached thereto. As was described in detail in U.S. Patent Application Publication No. 2015/0272575, the firing drive system 530 may employ an electric motor 505 that is located in the pistol grip portion 504 of the handle assembly 500. In various forms, the motor 505 may be a DC brushed driving motor having a maximum rotation of, approximately, 25,000 RPM, for example. In other arrangements, the motor 505 may include a brushless motor, a cordless motor, a synchronous motor, a stepper motor, or any other suitable electric motor. The motor 505 may be powered by a power source 522 that in one form may comprise a removable power pack. The power pack may support a plurality of Lithium Ion ("LI") or other suitable batteries therein. A number of batteries connected in series or parallel may be used as the power source 522 for the surgical system 10. In addition, the power source 522 may be replaceable and/or rechargeable.

The electric motor 505 is configured to axially drive a longitudinally movable drive member 540 (FIG. 3) in distal and proximal directions depending upon the polarity of the motor. For example, when the motor 505 is driven in one rotary direction, the longitudinally movable drive member will be axially driven in a distal direction "DD". When the motor 505 is driven in the opposite rotary direction, the longitudinally movable drive member 540 will be axially driven in a proximal direction "PD". The handle assembly 500 can include a switch 513 which can be configured to reverse the polarity applied to the electric motor 505 by the power source 522 or otherwise control the motor 505. The handle assembly 500 can also include a sensor or sensors (not shown) that is configured to detect the position of the drive member and/or the direction in which the drive member is being moved. Actuation of the motor 505 can be controlled by a firing trigger (not shown) that is adjacent to the closure trigger 512 and pivotally supported on the handle assembly 500. The firing trigger may be pivoted between an unactuated position and an actuated position. The firing trigger may be biased into the unactuated position by a spring or other biasing arrangement such that when the clinician releases the firing trigger, it may be pivoted or otherwise returned to the unactuated position by the spring or biasing arrangement. In at least one form, the firing trigger can be positioned "outboard" of the closure trigger 512. As discussed in U.S. Patent Application Publication No. 2015/0272575, the handle assembly 500 may be equipped with a firing trigger safety button (not shown) to prevent inadvertent actuation of the firing trigger. When the closure trigger 512 is in the unactuated position, the safety button is contained in the handle assembly 500 where the clinician cannot readily access it and move it between a safety position, preventing actuation of the firing trigger and a firing position, wherein the firing trigger may be fired. As the clinician depresses the closure trigger, the safety button and the firing trigger pivot down wherein they can then be manipulated by the clinician.

In at least one form, the longitudinally movable drive member 540 may have a rack of teeth 542 formed thereon for meshing engagement with a corresponding drive gear arrangement (not shown) that interfaces with the motor. See FIG. 3. Further details regarding those features may be found in U.S. Patent Application Publication No. 2015/0272575. In at least one arrangement, however, the longitudinally movable drive member is insulated to protect it from inadvertent RF energy. At least one form also includes a manually-actuatable "bailout" assembly that is configured to enable the clinician to manually retract the longitudinally movable drive member should the motor 505 become disabled. The bailout assembly may include a lever or bailout handle assembly that is stored within the handle assembly 500 under a releasable door 550. See FIG. 2. The lever may be configured to be manually pivoted into ratcheting engagement with the teeth in the drive member. Thus, the clinician can manually retract the drive member 540 by using the bailout handle assembly to ratchet the drive member in the proximal direction "PD". U.S. Pat. No. 8,608,045, entitled POWERED SURGICAL CUTTING AND STAPLING APPARATUS WITH MANUALLY RETRACTABLE FIRING SYSTEM, the entire disclosure of which is hereby incorporated by reference herein, discloses bailout arrangements and other components, arrangements and systems that may also be employed with any one of the various interchangeable surgical tool assemblies disclosed herein.

In the illustrated aspect, the interchangeable surgical tool assembly 1000 includes a surgical end effector 1500 that comprises a first jaw 1600 and a second jaw 1800. In one arrangement, the first jaw comprises an elongate channel 1602 that is configured to operably support a conventional (mechanical) surgical staple/fastener cartridge 1400 (FIG. 4) or a radio frequency (RF) cartridge 1700 (FIGS. 1 and 2) therein. The second jaw 1800 comprises an anvil 1810 that is pivotally supported relative to the elongate channel 1602. The anvil 1810 may be selectively moved toward and away from a surgical cartridge supported in the elongate channel 1602 between open and closed positions by actuating the closure drive system 510. In the illustrated arrangement, the anvil 1810 is pivotally supported on a proximal end portion of the elongate channel 1602 for selective pivotal travel about a pivot axis that is transverse to the shaft axis SA. Actuation of the closure drive system 510 may result in the distal axial movement of a proximal closure member or proximal closure tube 1910 that is attached to an articulation connector 1920.

Figure 3:
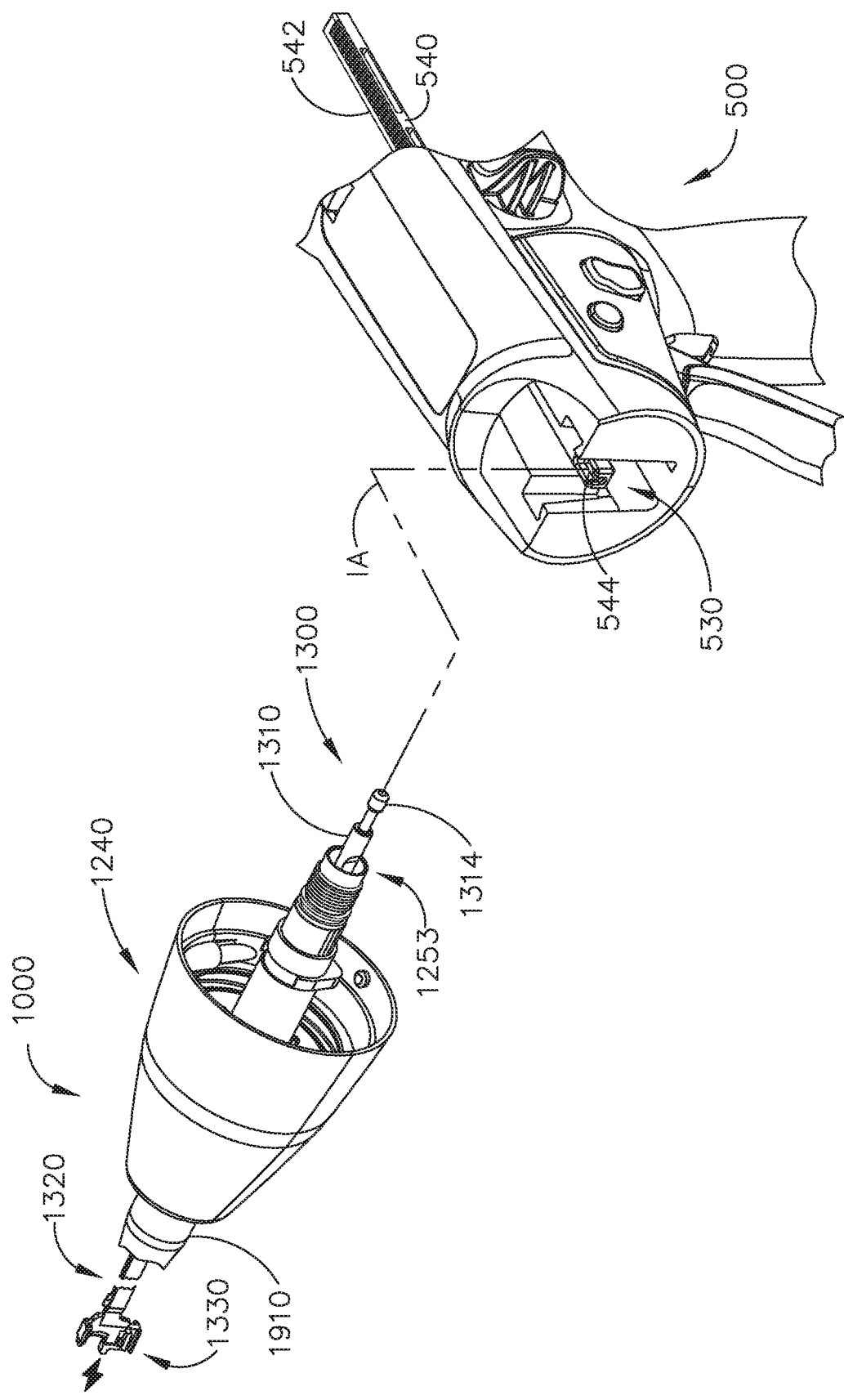
FIG. 3 is another exploded perspective assembly view of portions of the handle assembly and interchangeable surgical tool assembly of FIGS. 1 and 2 according to one aspect of this disclosure.
Figure 4:
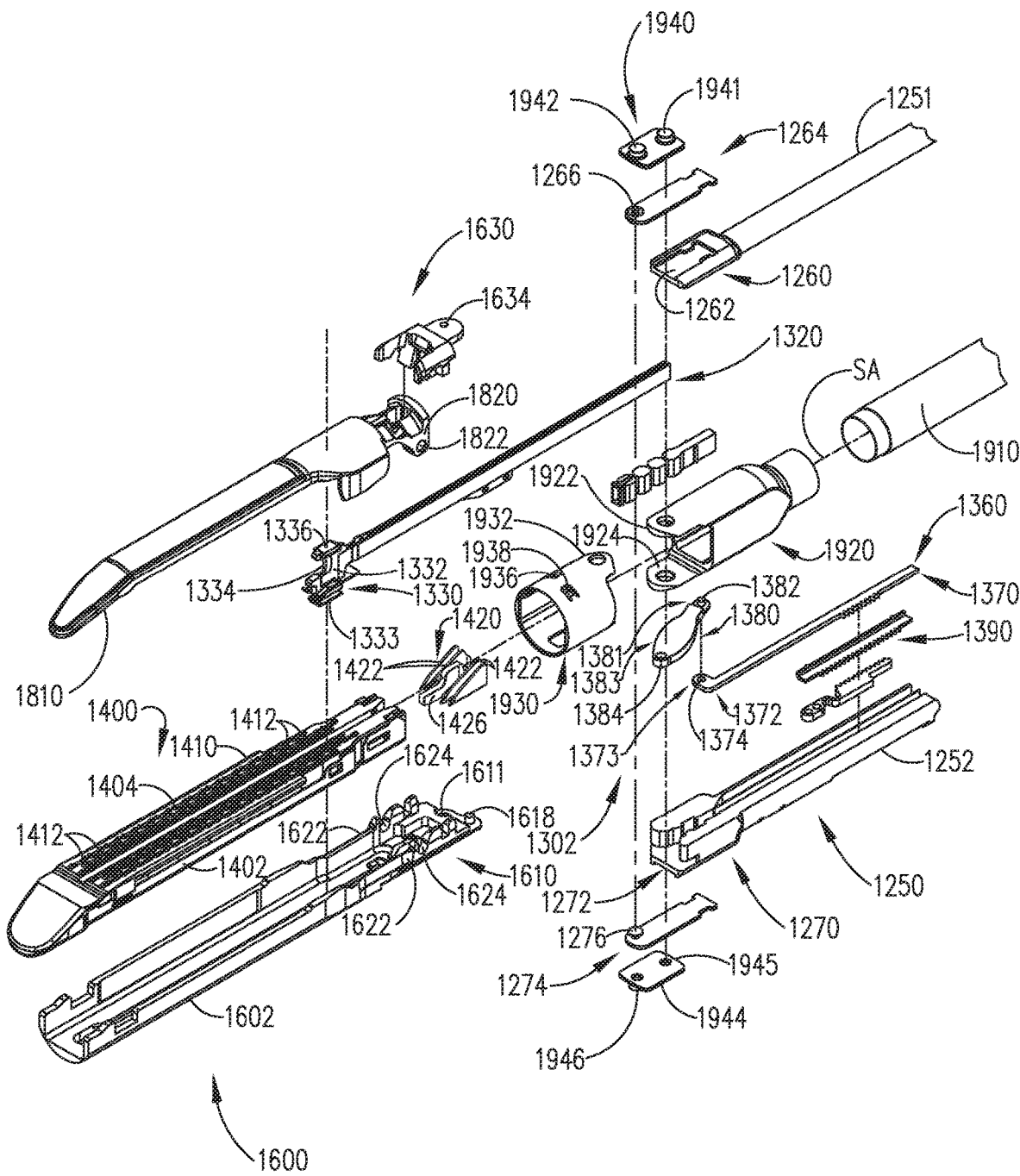
FIG. 4 is an exploded assembly view of a proximal portion of the interchangeable surgical tool assembly of FIGS. 1-3 according to one aspect of this disclosure.

Turning to FIG. 4, the articulation connector 1920 includes upper and lower tangs 1922, 1924 protrude distally from a distal end of the articulation connector 1920 to be movably coupled to an end effector closure sleeve or distal closure tube segment 1930. See FIG. 3. The distal closure tube segment 1930 includes an upper tang 1932 and a lower tang (not shown) that protrude proximally from a proximal end thereof. An upper double pivot link 1940 includes proximal and distal pins 1941, 1942 that engage corresponding holes in the upper tangs 1922, 1932 of the articulation connector 1920 and distal closure tube segment 1930, respectively. Similarly, a lower double pivot link 1944 includes proximal and distal pins 1945, 1946 that engage corresponding holes in the lower tangs 1924 of the articulation connector 1920 and distal closure tube segment 1930, respectively.

Still referring to FIG. 4, in the illustrated example, the distal closure tube segment 1930 includes positive jaw opening features or tabs 1936, 1938 that correspond with corresponding portions of the anvil 1810 to apply opening motions to the anvil 1810 as the distal closure tube segment 1930 is retracted in the proximal direction PD to a starting position. Further details regarding the opening and closing of the anvil 1810 may be found in U.S. patent application Ser. No. 15/635,621, entitled SURGICAL INSTRUMENT WITH POSITIVE JAW OPENING FEATURES, now U.S. Patent Application Publication No. 2019/0000463, filed on Jun. 28, 2017, the entire disclosure of which is hereby incorporated by reference herein.

Figure 5:
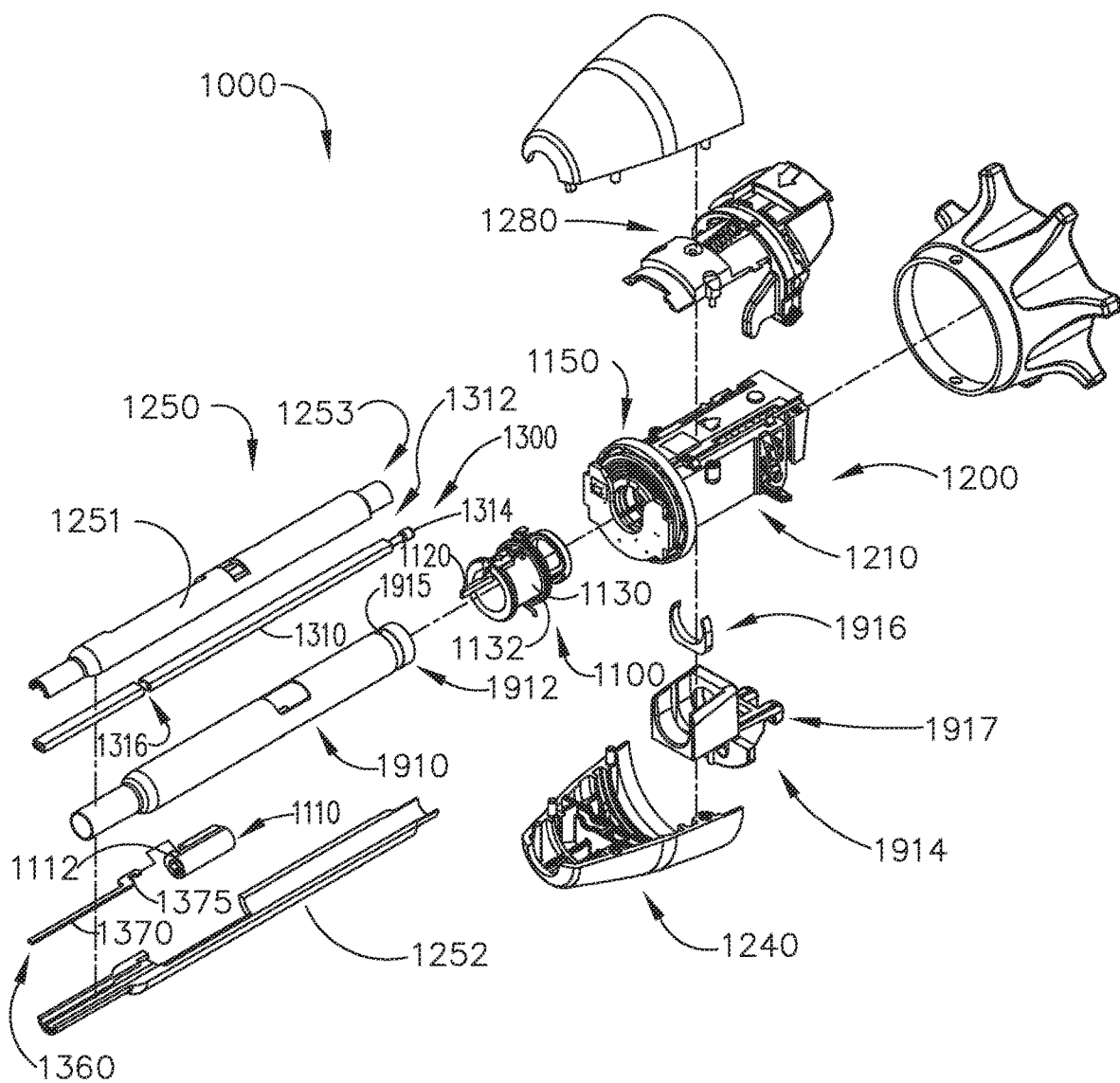
FIG. 5 is another exploded assembly view of a distal portion of the interchangeable surgical tool assembly of FIGS. 1-5 according to one aspect of this disclosure.

As shown in FIG. 5, in at least one arrangement, the interchangeable surgical tool assembly 1000 includes a tool frame assembly 1200 that comprises a tool chassis 1210 that operably supports a nozzle assembly 1240 thereon. As further discussed in detail in U.S. patent application Ser. No. 15/635,631, entitled SURGICAL INSTRUMENT WITH AXIALLY MOVABLE CLOSURE MEMBER, now U.S. Patent Application Publication No. 2019/0000464, filed on Jun. 28, 2017, and which is hereby incorporated by reference in its entirety herein, the tool chassis 1210 and nozzle arrangement 1240 facilitate rotation of the surgical end effector 1500 about a shaft axis SA relative to the tool chassis 1210. Such rotational travel is represented by arrow R in FIG. 1. As also shown in FIGS. 4 and 5, the interchangeable surgical tool assembly 1000 includes a spine assembly 1250 that operably supports the proximal closure tube 1910 and is coupled to the surgical end effector 1500. In various circumstances, for ease of assembly, the spine assembly 1250 may be fabricated from an upper spine segment 1251 and a lower spine segment 1252 that are interconnected together by snap features, adhesive, welding, etc. In assembled form, the spine assembly 1250 includes a proximal end 1253 that is rotatably supported in the tool chassis 1210. In one arrangement, for example, the proximal end 1253 of the spine assembly 1250 is attached to a spine bearing (not shown) that is configured to be supported within the tool chassis 1210. Such arrangement facilitates rotatable attachment of the spine assembly 1250 to the tool chassis such that the spine assembly 1250 may be selectively rotated about a shaft axis SA relative to the tool chassis 1210.

As shown in FIG. 4, the upper spine segment 1251 terminates in an upper lug mount feature 1260 and the lower spine segment 1252 terminates in a lower lug mount feature 1270. The upper lug mount feature 1260 is formed with a lug slot 1262 therein that is adapted to mountingly support an upper mounting link 1264 therein. Similarly, the lower lug mount feature 1270 is formed with a lug slot 1272 therein that is adapted to mountingly support a lower mounting link 1274 therein. The upper mounting link 1264 includes a pivot socket 1266 therein that is offset from the shaft axis SA. The pivot socket 1266 is adapted to rotatably receive therein a pivot pin 1634 that is formed on a channel cap or anvil retainer 1630 that is attached to a proximal end portion 1610 of the elongate channel 1602. The lower mounting link 1274 includes lower pivot pin 1276 that adapted to be received within a pivot hole 1611 formed in the proximal end portion 1610 of the elongate channel 1602. The lower pivot pin 1276 as well as the pivot hole 1611 is offset from the shaft axis SA. The lower pivot pin 1276 is vertically aligned with the pivot socket 1266 to define the articulation axis AA about which the surgical end effector 1500 may articulate relative to the shaft axis SA. See FIG. 1. Although the articulation axis AA is transverse to the shaft axis SA, in at least one arrangement, the articulation axis AA is laterally offset therefrom and does not intersect the shaft axis SA.

Turning to FIG. 5, a proximal end 1912 of the proximal closure tube 1910 is rotatably coupled to a closure shuttle 1914 by a connector 1916 that is seated in an annular groove 1915 in the proximal closure tube segment 1910. The closure shuttle 1914 is supported for axial travel within the tool chassis 1210 and has a pair of hooks 1917 thereon configured to engage the closure drive system 510 when the tool chassis 1210 is coupled to the handle frame 506. The tool chassis 1210 further supports a latch assembly 1280 for releasably latching the tool chassis 1210 to the handle frame 506. Further details regarding the tool chassis 1210 and latch assembly 1280 may be found in U.S. patent application Ser. No. 15/635,631, entitled SURGICAL INSTRUMENT WITH AXIALLY MOVABLE CLOSURE MEMBER, Attorney now U.S. Patent Application Publication No. 2019/0000464, filed on Jun. 28, 2017, and the entire disclosure of which is hereby incorporated by reference herein.

The firing drive system 530 in the handle assembly 500 is configured to be operably coupled to a firing system 1300 that is operably supported in the interchangeable surgical tool assembly 1000. The firing system 1300 may include an intermediate firing shaft portion 1310 that is configured to be axially moved in the distal and proximal directions in response to corresponding firing motions applied thereto by the firing drive system 530. See FIG. 4. As shown in FIG. 5, a proximal end 1312 of the intermediate firing shaft portion 1310 has a firing shaft attachment lug 1314 formed thereon that is configured to be seated into an attachment cradle 544 (FIG. 3) that is on the distal end of the longitudinally movable drive member 540 of the firing drive system 530 within the handle assembly 500. Such arrangement facilitates the axial movement of the intermediate firing shaft portion 1310 upon actuation of the firing drive system 530. In the illustrated example, the intermediate firing shaft portion 1310 is configured for attachment to a distal cutting portion or knife bar 1320. As shown in FIG. 4, the knife bar 1320 is connected to a firing member or knife member 1330. The knife member 1330 comprises a knife body 1332 that operably supports a tissue cutting blade 1334 thereon. The knife body 1332 may further include anvil engagement tabs or features 1336 and channel engagement features or a foot 1338. The anvil engagement features 1336 may serve to apply additional closure motions to the anvil 1810 as the knife member 1330 is advanced distally through the end effector 1500.

In the illustrated example, the surgical end effector 1500 is selectively articulatable about the articulation axis AA by an articulation system 1360. In one form, the articulation system 1360 includes proximal articulation driver 1370 that is pivotally coupled to an articulation link 1380. As can be most particularly seen in FIG. 4, an offset attachment lug 1373 is formed on a distal end 1372 of the proximal articulation driver 1370. A pivot hole 1374 is formed in the offset attachment lug 1373 and is configured to pivotally receive therein a proximal link pin 1382 formed on the proximal end 1381 of the articulation link 1380. A distal end 1383 of the articulation link 1380 includes a pivot hole 1384 that is configured to pivotally receive therein a channel pin 1618 formed on the proximal end portion 1610 of the elongate channel 1602. Thus, axial movement of proximal articulation driver 1370 will thereby apply articulation motions to the elongate channel 1602 to thereby cause the surgical end effector 1500 to articulate about the articulation axis AA relative to the spine assembly 1250. In various circumstances, the proximal articulation driver 1370 can be held in position by an articulation lock 1390 when the proximal articulation driver 1370 is not being moved in the proximal or distal directions. Further details regarding an example form of articulation lock 1390 may be found in U.S. patent application Ser. No. 15/635,837, entitled SURGICAL INSTRUMENT COMPRISING AN ARTICULATION SYSTEM LOCKABLE TO A FRAME, now U.S. Patent Application Publication No. 2019/0000472, filed on Jun. 28, 2017, the entire disclosure of which is hereby incorporated by reference herein.

Further to the above, the interchangeable surgical tool assembly 1000 can include a shifter assembly 1100 which can be configured to selectively and releasably couple the proximal articulation driver 1310 to the firing system 1300. As illustrated in FIG. 5, for example, in one form, the shifter assembly 1100 includes a lock collar, or lock sleeve 1110, positioned around the intermediate firing shaft portion 1310 of the firing system 1300 wherein the lock sleeve 1110 can be rotated between an engaged position in which the lock sleeve 1110 operably couples the proximal articulation driver 1370 to the firing member assembly 1300 and a disengaged position in which the proximal articulation driver 1370 is not operably coupled to the firing member assembly 1300. When lock sleeve 1110 is in its engaged position, distal movement of the firing member assembly 1300 can move the proximal articulation driver 1370 distally and, correspondingly, proximal movement of the firing member assembly 1300 can move the proximal articulation driver 1370 proximally. When lock sleeve 1110 is in its disengaged position, movement of the firing member assembly 1300 is not transmitted to the proximal articulation driver 1370 and, as a result, the firing member assembly 1300 can move independently of the proximal articulation driver 1370. In various circumstances, the proximal articulation driver 1370 can be held in position by the articulation lock 1390 when the proximal articulation driver 1370 is not being moved in the proximal or distal directions by the firing member assembly 1300.

In the illustrated arrangement, the intermediate firing shaft portion 1310 of the firing member assembly 1300 is formed with two opposed flat sides with a drive notch 1316 formed therein. See FIG. 5. As can also be seen in FIG. 5, the lock sleeve 1110 comprises a cylindrical, or an at least substantially cylindrical, body that includes a longitudinal aperture that is configured to receive the intermediate firing shaft portion 1310 therethrough. The lock sleeve 1110 can comprise diametrically-opposed, inwardly-facing lock protrusions that, when the lock sleeve 1110 is in one position, are engagingly received within corresponding portions of the drive notch 1316 in the intermediate firing shaft portion 1310 and, when in another position, are not received within the drive notch 1316 to thereby permit relative axial motion between the lock sleeve 1110 and the intermediate firing shaft 1310. As can be further seen in FIG. 5, the lock sleeve 1110 further includes a lock member 1112 that is sized to be movably received within a notch 1375 in a proximal end of the proximal articulation driver 1370. Such arrangement permits the lock sleeve 1110 to slightly rotate into and out of engagement with the intermediate firing shaft portion 1310 while remaining in position for engagement or in engagement with the notch 1375 in the proximal articulation driver 1370. For example, when the lock sleeve 1110 is in its engaged position, the lock protrusions are positioned within the drive notch 1316 in the intermediate firing shaft portion 1310 such that a distal pushing force and/or a proximal pulling force can be transmitted from the firing member assembly 1300 to the lock sleeve 1110. Such axial pushing or pulling motion is then transmitted from the lock sleeve 1110 to the proximal articulation driver 1370 to thereby articulate the surgical end effector 1500. In effect, the firing member assembly 1300, the lock sleeve 1110, and the proximal articulation driver 1370 will move together when the lock sleeve 1110 is in its engaged (articulation) position. On the other hand, when the lock sleeve 1110 is in its disengaged position, the lock protrusions are not received within the drive notch 1316 in the intermediate firing shaft portion 1310 and, as a result, a distal pushing force and/or a proximal pulling force may not be transmitted from the firing member assembly 1300 to the lock sleeve 1110 (and the proximal articulation driver 1370).

In the illustrated example, relative movement of the lock sleeve 1110 between its engaged and disengaged positions may be controlled by the shifter assembly 1100 that interfaces with the proximal closure tube 1910. Still referring to FIG. 5, the shifter assembly 1100 further includes a shifter key 1120 that is configured to be slidably received within a key groove formed in the outer perimeter of the lock sleeve 1110. Such arrangement enables the shifter key 1120 to move axially with respect to the lock sleeve 1110. As discussed in further detail in U.S. patent application Ser. No. 15/635,631, entitled SURGICAL INSTRUMENT WITH AXIALLY MOVABLE CLOSURE MEMBER, now U.S. Patent Application Publication No. 2019/0000464, filed on Jun. 28, 2017, the entire disclosure of which is hereby incorporated by reference herein, a portion of the shifter key 1120 is configured to cammingly interact with a cam opening (not shown) in the proximal closure tube portion 1910. Also in the illustrated example, the shifter assembly 1100 further includes a switch drum 1130 that is rotatably received on a proximal end portion of the proximal closure tube portion 1910. A portion of the shifter key 1120 extends through an axial slot segment in the switch drum 1130 and is movably received within an arcuate slot segment in the switch drum 1130. A switch drum torsion spring 1132 is mounted on the switch drum 1130 and engages a portion of the nozzle assembly 1240 to apply a torsional bias or rotation which serves to rotate the switch drum 1130 until the portion of the shifter key 1120 reaches an end portion of the cam opening in the proximal closure tube portion 1910. When in this position, the switch drum 1130 may provide a torsional bias to the shifter key 1120 which thereby causes the lock sleeve 1110 to rotate into its engaged position with the intermediate firing shaft portion 1310. This position also corresponds to the unactuated configuration of the proximal closure tube 1910 (and distal closure tube segment 1930).

In one arrangement, for example, when the proximal closure tube 1910 is in an unactuated configuration (anvil 1810 is in an open position spaced away from the cartridge mounted in the elongate channel 1602) actuation of the intermediate firing shaft portion 1310 will result in the axial movement of the proximal articulation driver 1370 to facilitate articulation of the end effector 1500. Once the user has articulated the surgical end effector 1500 to a desired orientation, the user may then actuate the proximal closure tube portion 1910. Actuation of the proximal closure tube portion 1910 will result in the distal travel of the distal closure tube segment 1930 to ultimately apply a closing motion to the anvil 1810. This distal travel of the proximal closure tube portion 1910 will result in the cam opening therein cammingly interacting with a cam portion of the shifter key 1120 to thereby cause the shifter key 1120 to rotate the lock sleeve 1110 in an actuation direction. Such rotation of the lock sleeve 1110 will result in the disengagement of the lock protrusions from the drive notch 1316 in the intermediate firing shaft portion 1310. When in such configuration, the firing drive system 530 may be actuated to actuate the intermediate firing shaft portion 1310 without actuating the proximal articulation driver 1370. Further details concerning the operation of the switch drum 1130 and lock sleeve 1110, as well as alternative articulation and firing drive arrangements that may be employed with the various interchangeable surgical tool assemblies described herein, may be found in U.S. patent application Ser. No. 13/803,086, now U.S. Patent Application Publication No. 2014/0263541, and U.S. patent application Ser. No. 15/019,196, the entire disclosures of which are hereby incorporated by reference herein.

Figure 15:
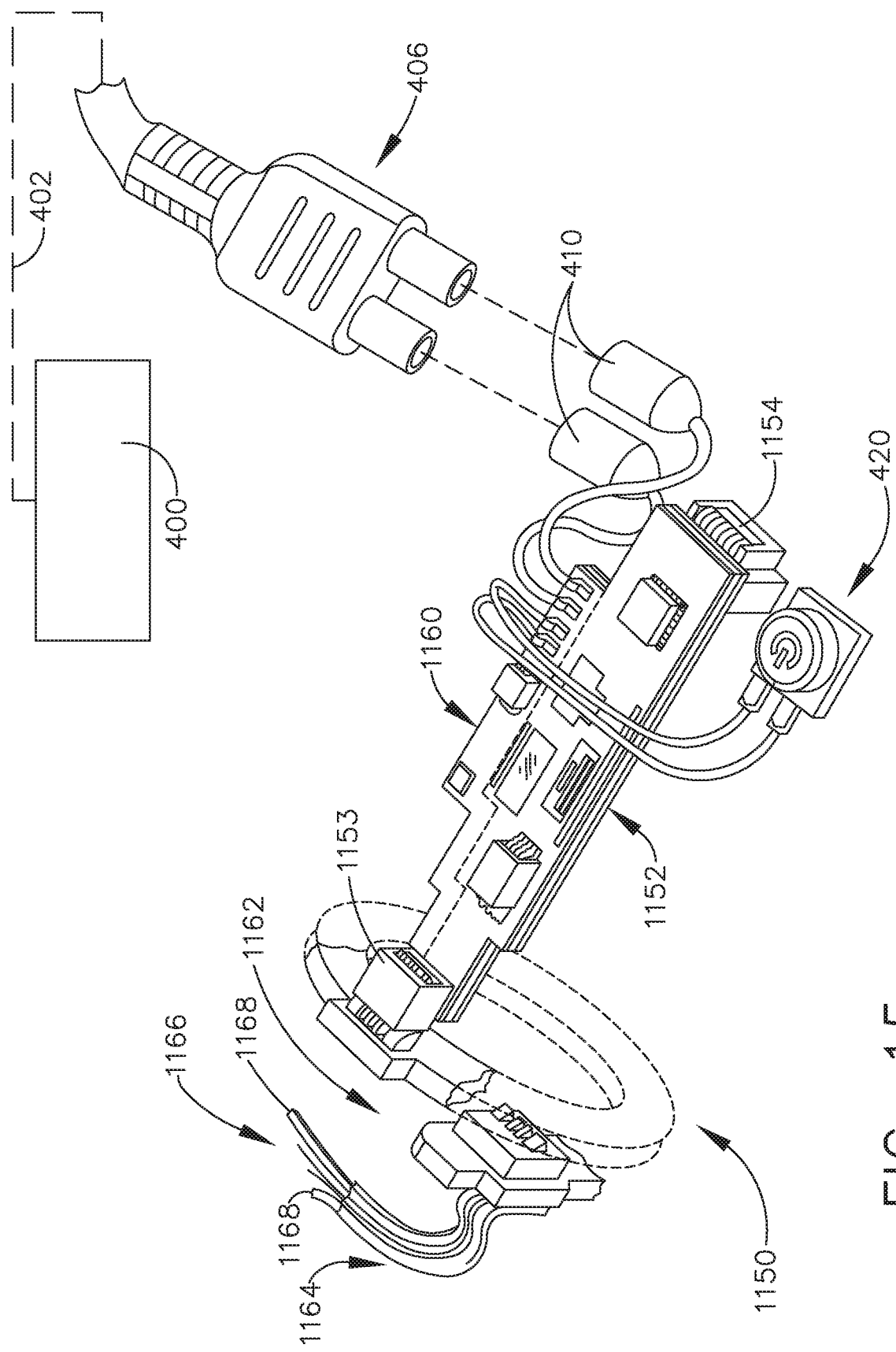
FIG. 15 is a perspective view of an onboard circuit board arrangement and RF generator plus configuration according to one aspect of this disclosure.

As also illustrated in FIGS. 5 and 15, the interchangeable surgical tool assembly 1000 can comprise a slip ring assembly 1150 which can be configured to conduct electrical power to and/or from the surgical end effector 1500 and/or communicate signals to and/or from the surgical end effector 1500, back to an onboard circuit board 1152, while facilitating rotational travel of the shaft and end effector 1500 about the shaft axis SA relative to the tool chassis 1210 by rotating the nozzle assembly 1240. As shown in FIG. 15, in at least one arrangement, the onboard circuit board 1152 includes an onboard connector 1154 that is configured to interface with a housing connector 560 (FIG. 9) communicating with a microprocessor 560 that is supported in the handle assembly 500 or robotic system controller, for example. The slip ring assembly 1150 is configured to interface with a proximal connector 1153 that interfaces with the onboard circuit board 1152. Further details concerning the slip ring assembly 1150 and associated connectors may be found in U.S. patent application Ser. No. 13/803,086, now U.S. Patent Application Publication No. 2014/0263541, and U.S. patent application Ser. No. 15/019,196 which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety.

An example version of the interchangeable surgical tool assembly 1000 disclosed herein may be employed in connection with a standard (mechanical) surgical fastener cartridge 1400 or a cartridge 1700 that is configured to facilitate cutting of tissue with the knife member and seal the cut tissue using radio frequency (RF) energy. Turning again to FIG. 4, a conventional or standard mechanical-type cartridge 1400 is depicted. Such cartridge arrangements are known and may comprise a cartridge body 1402 that is sized and shaped to be removably received and supported in the elongate channel 1602. For example, the cartridge body 1402 may be configured to be removably retained in snap engagement with the elongate channel 1602. The cartridge body 1402 includes an elongate slot 1404 to accommodate axial travel of the knife member 1330 therethrough. The cartridge body 1402 operably supports therein a plurality of staple drivers (not shown) that are aligned in rows on each side of the centrally disposed elongate slot 1404. The drivers are associated with corresponding staple/fastener pockets 1412 that open through the upper deck surface 1410 of the cartridge body 1402. Each of the staple drivers supports one or more surgical staple or fastener (not shown) thereon. A sled assembly 1420 is supported within a proximal end of the cartridge body 1402 and is located proximal to the drivers and fasteners in a starting position when the cartridge 1400 is new and unfired. The sled assembly 1420 includes a plurality of sloped or wedge-shaped cams 1422 wherein each cam 1422 corresponds to a particular line of fasteners or drivers located on a side of the slot 1404. The sled assembly 1420 is configured to be contacted and driven by the knife member 1330 as the knife member is driven distally through the tissue that is clamped between the anvil and the cartridge deck surface 1410. As the drivers are driven upward toward the cartridge deck surface 1410, the fastener(s) supported thereon are driven out of their staple pockets 1412 and through the tissue that is clamped between anvil and the cartridge.

Still referring to FIG. 4, the anvil 1810 in at least one form includes an anvil mounting portion 1820 that has a pair of anvil trunnions 1822 protruding laterally therefrom to be pivotally received in corresponding trunnion cradles 1614 formed in the upstanding walls 1622 of the proximal end portion 1610 of the elongate channel 1602. The anvil trunnions 1822 are pivotally retained in their corresponding trunnion cradle 1614 by the channel cap or anvil retainer 1630. The anvil mounting portion 1820 is movably or pivotably supported on the elongate channel 1602 for selective pivotal travel relative thereto about a fixed anvil pivot axis that is transverse to the shaft axis SA. As shown in FIGS. 6 and 7, in at least one form, the anvil 1810 includes an anvil body portion 1812 that is fabricated from an electrically conductive metal material for example and has a staple forming undersurface 1813 that has a series of fastener forming pockets 1814 formed therein on each side of a centrally disposed anvil slot 1815 that is configured to slidably accommodate the knife member 1330 therein. The anvil slot 1815 opens into an upper opening 1816 that extends longitudinally through the anvil body 1812 to accommodate the anvil engagement features 1336 on the knife member 1330 during firing. When a conventional mechanical surgical staple/fastener cartridge 1400 is installed in the elongate channel 1602, the staples/fasteners are driven through the tissue T and into forming contact with the corresponding fastener forming pockets 1814. The anvil body 1812 may have an opening in the upper portion thereof to facilitate ease of installation for example. An anvil cap 1818 may be inserted therein and welded to the anvil body 1812 to enclose the opening and improve the overall stiffness of the anvil body 1812. As shown in FIG. 7, to facilitate use of the end effector 1500 in connection with RF cartridges 1700, the tissue facing segments 1817 of the fastener forming undersurface 1813 may have electrically insulative material 1819 thereon.

Figure 8:
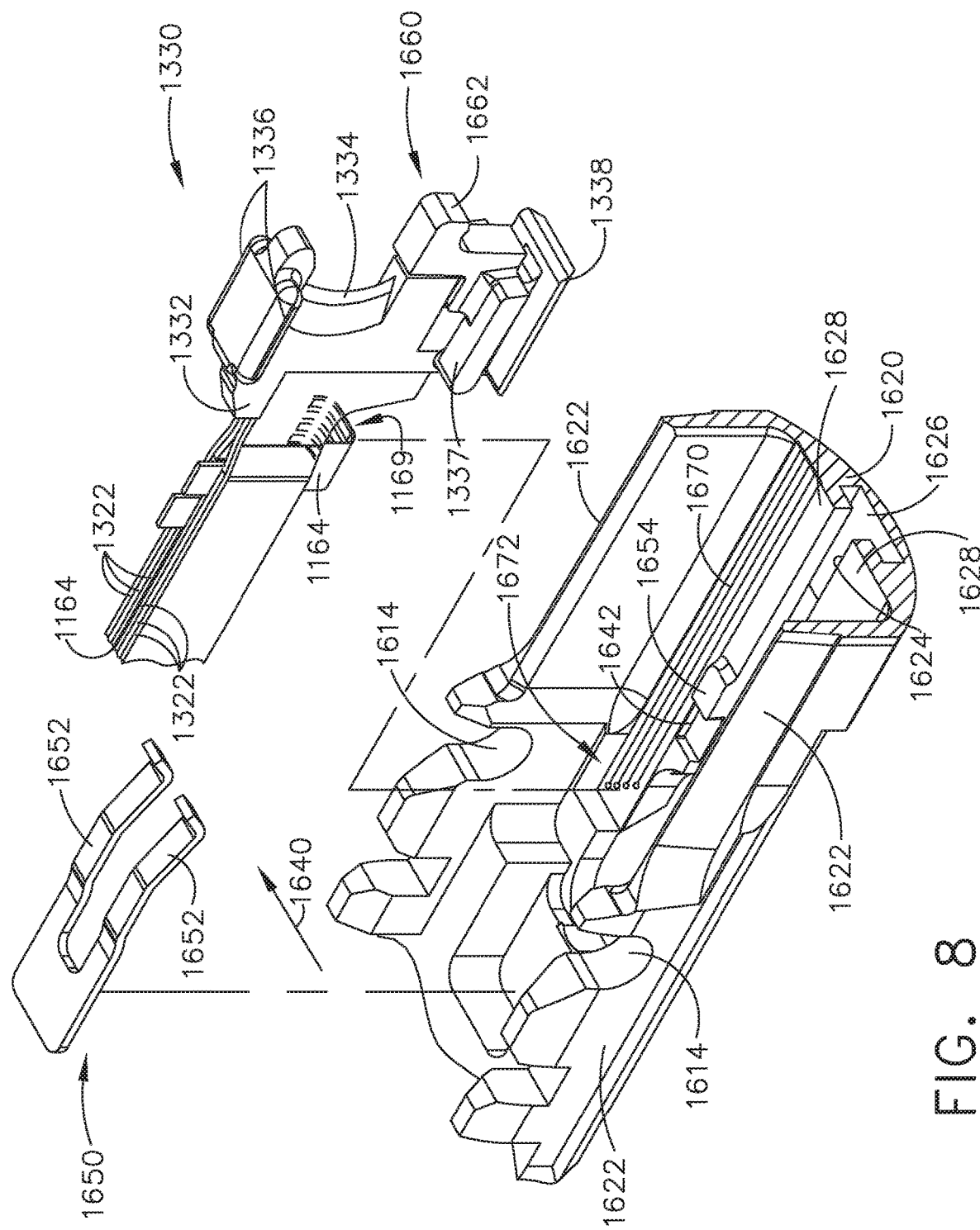
FIG. 8 is another exploded assembly view of a portion of the interchangeable surgical tool assembly of FIGS. 1-5 according to one aspect of this disclosure.

In the illustrated arrangement, the interchangeable surgical tool assembly 1000 is configured with a firing member lockout system, generally designated as 1640. See FIG. 8. As shown in FIG. 8, the elongate channel 1602 includes a bottom surface or bottom portion 1620 that has two upstanding side walls 1622 protruding therefrom. A centrally disposed longitudinal channel slot 1624 is formed through the bottom portion 1620 to facilitate the axial travel of the knife member 1330 therethrough. The channel slot 1624 opens into a longitudinal passage 1626 that accommodates the channel engagement feature or foot 1338 on the knife member 1330. The passage 1626 serves to define two inwardly extending ledge portions 1628 that serve to engage corresponding portions of the channel engagement feature or foot 1338. The firing member lockout system 1640 includes proximal openings 1642 located on each side of the channel slot 1624 that are each configured to receive corresponding portions of the channel engagement feature or foot 1338 when the knife member 1330 is in a starting position. A knife lockout spring 1650 is supported in the proximal end 1610 of the elongate channel 1602 and serves to bias the knife member 1330 downward. As shown in FIG. 8, the knife lockout spring 1650 includes two distally ending spring arms 1652 that are configured to engage corresponding central channel engagement features 1337 on the knife body 1332. The spring arms 1652 are configured to bias the central channel engagement features 1337 downward. Thus, when in the starting (unfired position), the knife member 1330 is biased downward such that the channel engagement features or foot 1338 is received within the corresponding proximal openings 1642 in the elongate 1602 channel. When in that locked position, if one were to attempt to distally advance the knife 1330, the central channel engagement features 1137 and/or foot 1338 would engage upstanding ledges 1654 on the elongate channel 1602 (FIGS. 8 and 11) and the knife 1330 could not be fired.

Still referring to FIG. 8, the firing member lockout system 1640 also includes an unlocking assembly 1660 formed or supported on a distal end of the firing member body 1332. The unlocking assembly 1660 includes a distally extending ledge 1662 that is configured to engage an unlocking feature 1426 formed on the sled assembly 1420 when the sled assembly 1420 is in its starting position in an unfired surgical staple cartridge 1400. Thus, when an unfired surgical staple cartridge 1400 is properly installed in the elongate channel 1602, the ledge 1662 on the unlocking assembly 1660 contacts the unlocking feature 1426 on the sled assembly 1420 which serves to bias the knife member 1330 upward such that the central channel engagement features 1137 and/or foot 1338 clear the upstanding ledges 1654 in the channel bottom 1620 to facilitate axial passage of the knife member 1330 through the elongate channel 1602. If a partially fired cartridge 1400 is unwittingly installed in the elongate channel, the sled assembly 1420 will not be in the starting position and the knife member 1330 will remain in the locked position.

Figure 9:
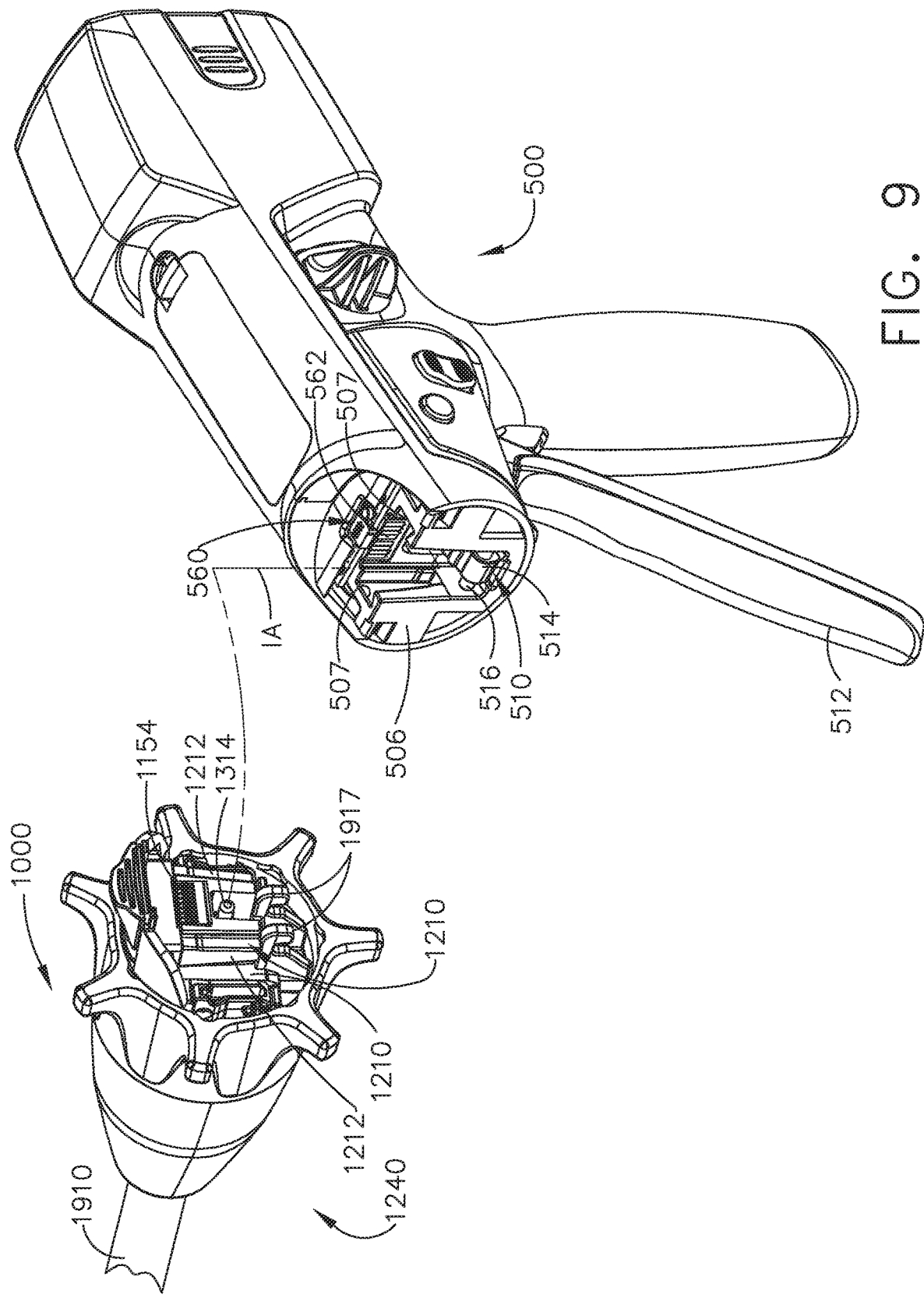
FIG. 9 is another exploded assembly view of the interchangeable surgical tool assembly and handle assembly of FIGS. 1 and 2 according to one aspect of this disclosure.

Attachment of the interchangeable surgical tool assembly 1000 to the handle assembly 500 will now be described with reference to FIGS. 3 and 9. To commence the coupling process, the clinician may position the tool chassis 1210 of the interchangeable surgical tool assembly 1000 above or adjacent to the distal end of the handle frame 506 such that tapered attachment portions 1212 formed on the tool chassis 1210 are aligned with dovetail slots 507 in the handle frame 506. The clinician may then move the surgical tool assembly 1000 along an installation axis IA that is perpendicular to the shaft axis SA to seat the tapered attachment portions 1212 in "operable engagement" with the corresponding dovetail receiving slots 507 in the distal end of the handle frame 506. In doing so, the firing shaft attachment lug 1314 on the intermediate firing shaft portion 1310 will also be seated in the cradle 544 in the longitudinally movable drive member 540 within the handle assembly 500 and the portions of a pin 516 on a closure link 514 will be seated in the corresponding hooks 1917 in the closure shuttle 1914. As used herein, the term "operable engagement" in the context of two components means that the two components are sufficiently engaged with each other so that upon application of an actuation motion thereto, the components may carry out their intended action, function and/or procedure. Also during this process, the onboard connector 1154 on the surgical tool assembly 1000 is coupled to the housing connector 562 that communicates with the microprocessor 560 that is supported in the handle assembly 500 or robotic system controller, for example.

During a typical surgical procedure, the clinician may introduce the surgical end effector 1500 into the surgical site through a trocar or other opening in the patient to access the target tissue. When doing so, the clinician typically axially aligns the surgical end effector 1500 along the shaft axis SA (unarticulated state). Once the surgical end effector 1500 has passed through the trocar port, for example, the clinician may need to articulate the end effector 1500 to advantageously position it adjacent the target tissue. This is prior to closing the anvil 1810 onto the target tissue, so the closure drive system 510 would remain unactuated. When in this position, actuation of the firing drive system 530 will result in the application of articulation motions to the proximal articulation driver 1370. Once the end effector 1500 has attained the desired articulated position, the firing drive system 530 is deactivated and the articulation lock 1390 may retain the surgical end effector 1500 in the articulated position. The clinician may then actuate the closure drive system 510 to close the anvil 1810 onto the target tissue. Such actuation of the closure drive system 510 may also result in the shifter assembly 1100 delinking the proximal articulation driver 1370 from the intermediate firing shaft portion 1310. Thus, once the target tissue has been captured in the surgical end effector 1500, the clinician may once again actuate the firing drive system 530 to axially advance the firing member 1330 through the surgical staple/fastener cartridge 1400 or RF cartridge 1700 to cut the clamped tissue and fire the staples/fasteners into the cut tissue T. Other closure and firing drive arrangements, actuator arrangements (both handheld, manual and automated or robotic) may also be employed to control the axial movement of the closure system components, the articulation system components and/or the firing system components of the surgical tool assembly 1000 without departing from the scope of the present disclosure.

As indicated above, the surgical tool assembly 1000 is configured to be used in connection with conventional mechanical surgical staple/fastener cartridges 1400 as well as with RF cartridges 1700. In at least one form, the RF cartridge 1700 may facilitate mechanical cutting of tissue that is clamped between the anvil 1810 and the RF cartridge 1700 with the knife member 1330 while coagulating electrical current is delivered to the tissue in the current path. Alternative arrangements for mechanically cutting and coagulating tissue using electrical current are disclosed in, for example, U.S. Pat. Nos. 5,403,312; 7,780,663 and U.S. patent application Ser. No. 15/142,609, entitled ELECTROSURGICAL INSTRUMENT WITH ELECTRICALLY CONDUCTIVE GAP SETTING AND TISSUE ENGAGING MEMBERS, the entire disclosures of each said references being incorporated by reference herein. Such instruments, may, for example, improve hemostasis, reduce surgical complexity as well as operating room time.

Figure 10:
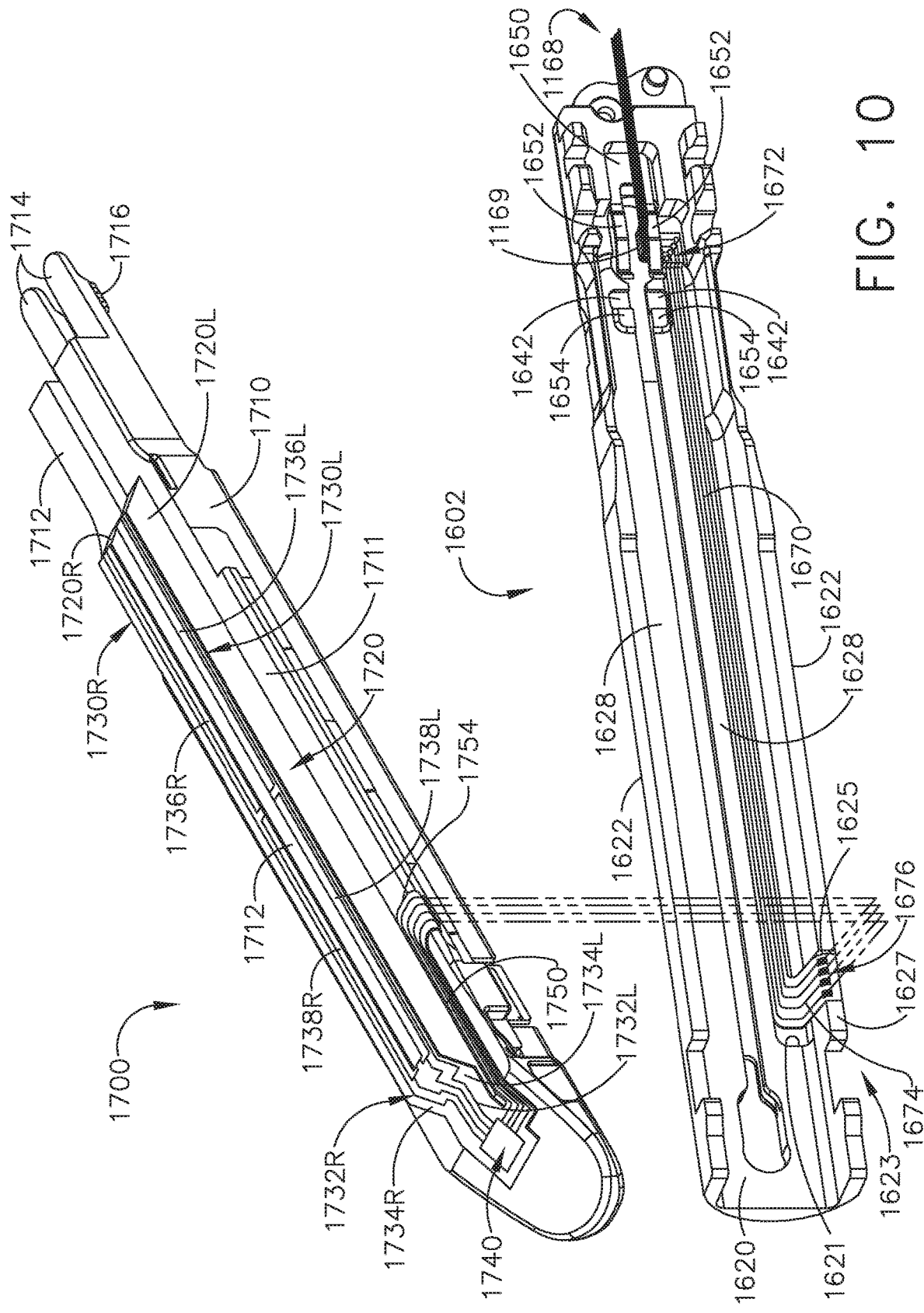
FIG. 10 is a perspective view of an RF cartridge and an elongate channel of the interchangeable surgical tool assembly of FIGS. 1-5 according to one aspect of this disclosure.
Figure 11:
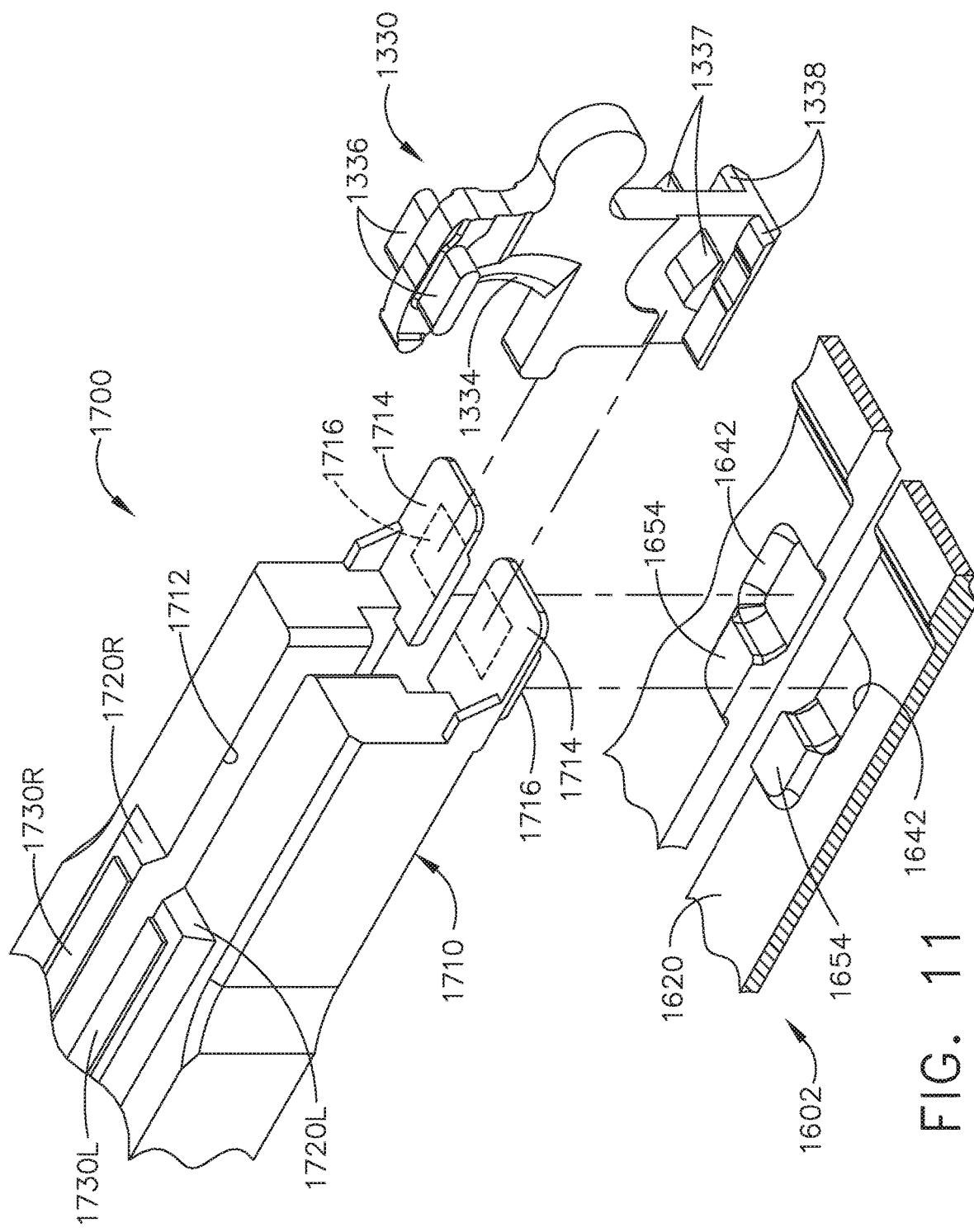
FIG. 11 is a partial perspective view of portions of the RF cartridge and elongate channel of FIG. 10 with a knife member according to one aspect of this disclosure.
Figure 12:
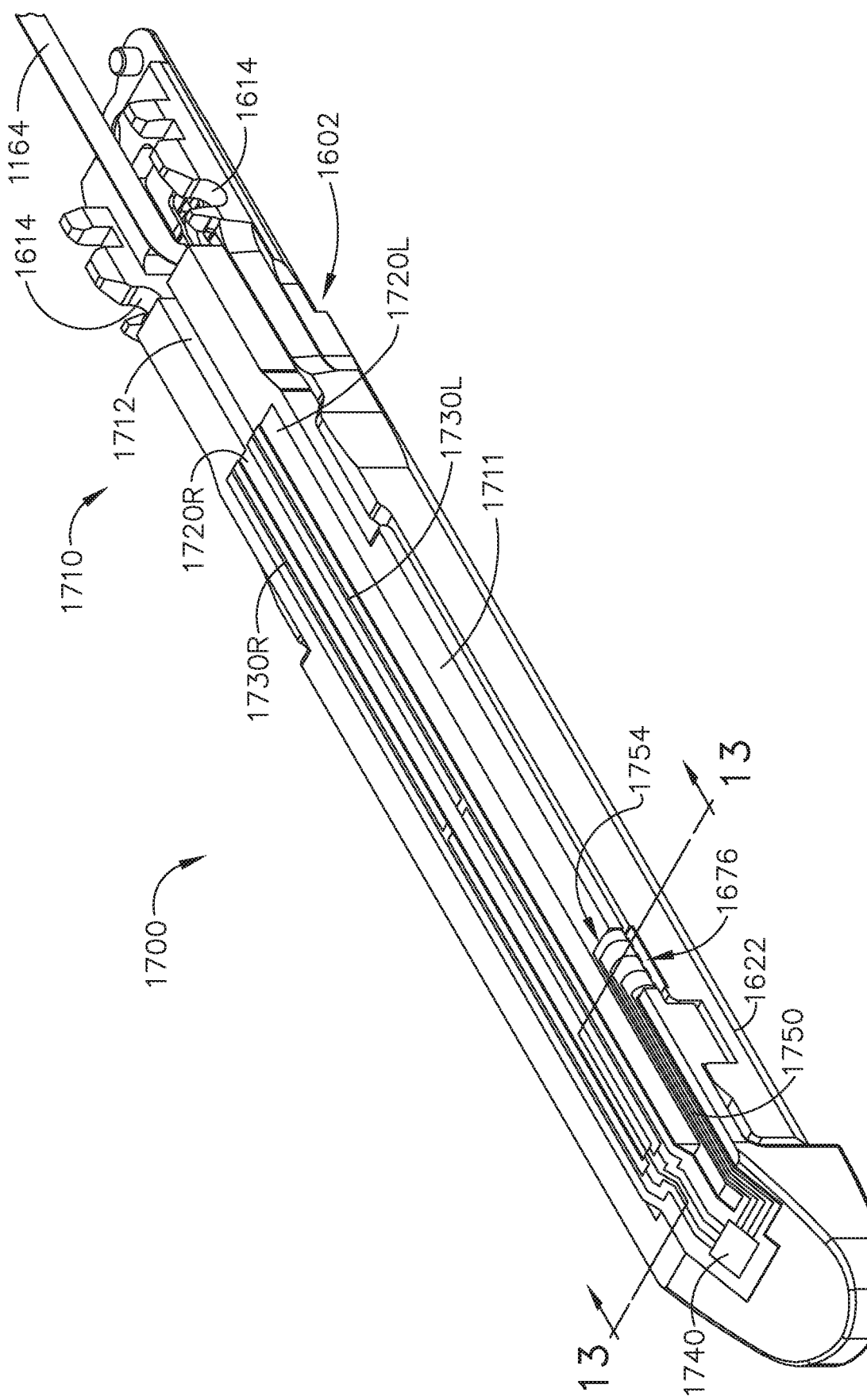
FIG. 12 is another perspective view of the RF cartridge installed in the elongate channel of FIG. 10 and illustrating a portion of a flexible shaft circuit arrangement according to one aspect of this disclosure.
Figure 13:
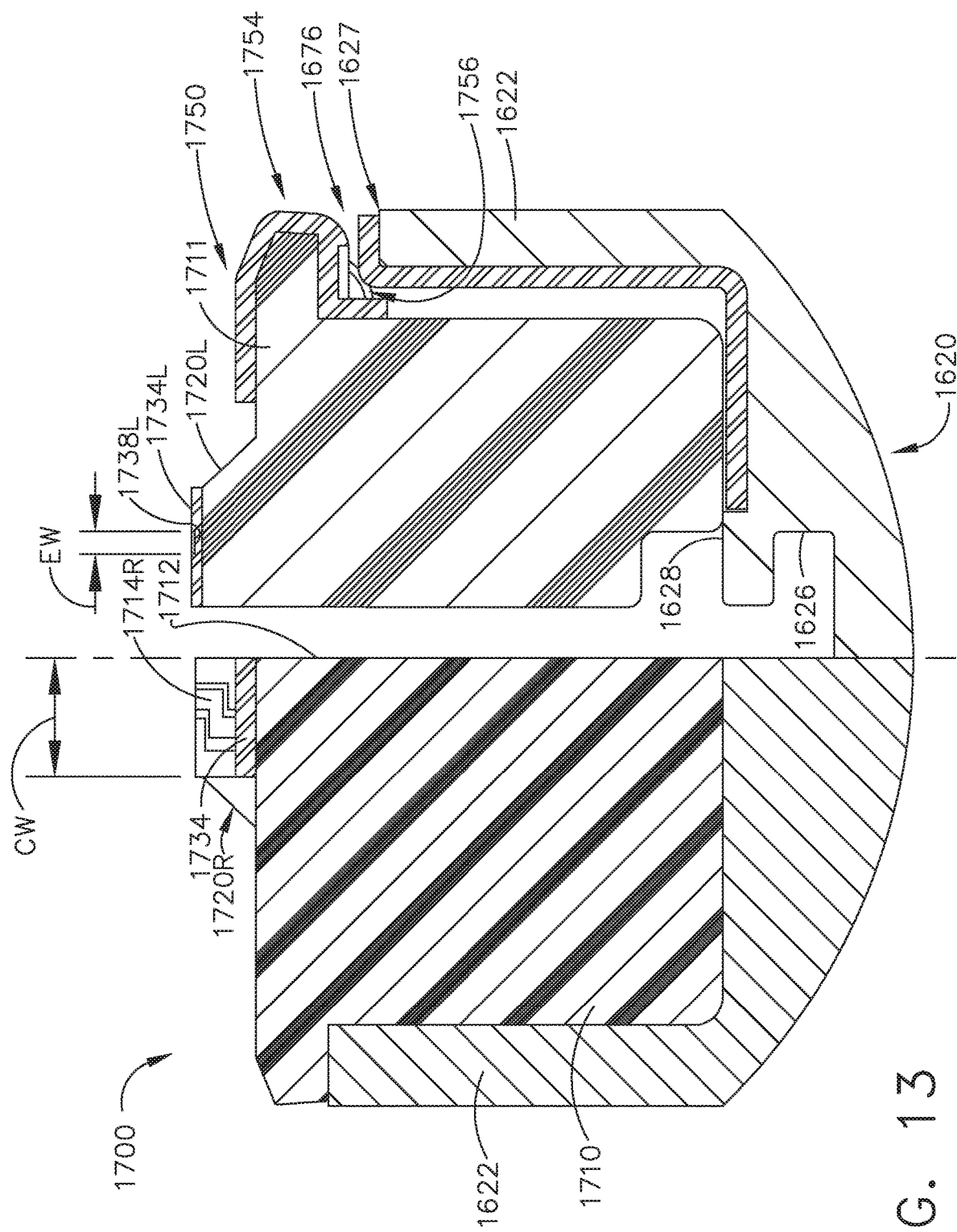
FIG. 13 is a cross-sectional end view of the RF cartridge and elongate channel of FIG. 12 taken along lines 13-13 in FIG. 12 according to one aspect of this disclosure.

As shown in FIGS. 10-12, in at least one arrangement, the RF surgical cartridge 1700 includes a cartridge body 1710 that is sized and shaped to be removably received and supported in the elongate channel 1602. For example, the cartridge body 1710 may be configured to be removably retained in snap engagement with the elongate channel 1602. In various arrangements, the cartridge body 1710 may be fabricated from a polymer material, such as, for example, an engineering thermoplastic such as the liquid crystal polymer (LCP) VECTRA™ and the elongate channel 1602 may be fabricated from metal. In at least one aspect, the cartridge body 1710 includes a centrally disposed elongate slot 1712 that extends longitudinally through the cartridge body to accommodate longitudinal travel of the knife 1330 therethrough. As shown in FIGS. 10 and 11, a pair of lockout engagement tails 1714 extend proximally from the cartridge body 1710. Each lockout engagement tail 1714 has a lockout pad 1716 formed on the underside thereof that are sized to be received within a corresponding proximal opening portion 1642 in the channel bottom 1620. Thus, when the cartridge 1700 is properly installed in the elongate channel 1602, the lockout engagement tails 1714 cover the openings 1642 and ledges 1654 to retain the knife 1330 in an unlocked position ready for firing.

Turning now to FIGS. 10-13, in the illustrated example, the cartridge body 1710 is formed with a centrally disposed raised electrode pad 1720. As can be most particularly seen in FIG. 6, the elongate slot 1712 extends through the center of the electrode pad 1720 and serves to divide the pad 1720 into a left pad segment 1720L and a right pad segment 1720R. A right flexible circuit assembly 1730R is attached to the right pad segment 1720R and a left flexible circuit assembly 1730L is attached to the left pad segment 1720L. In at least one arrangement for example, the right flexible circuit 1730R comprises a plurality of electrical conductors 1732R that may include, for example, wider electrical conductors/conductors for RF purposes and thinner electrical conductors for conventional stapling purposes that are supported or attached or embedded into a right insulator sheath/member 1734R that is attached to the right pad 1720R. In addition, the right flexible circuit assembly 1730R includes a "phase one", proximal right electrode 1736R and a "phase two" distal right electrode 1738R. Likewise, the left flexible circuit assembly 1730L comprises a plurality of electrical conductors 1732L that may include, for example, wider electrical conductors/conductors for RF purposes and thinner electrical conductors for conventional stapling purposes that are supported or attached or embedded into a left insulator sheath/member 1734L that is attached to the left pad 1720L. In addition, the left flexible circuit assembly 1730L includes a "phase one", proximal left electrode 1736L and a "phase two" distal left electrode 1738L. The left and right electrical conductors 1732L, 1732R are attached to a distal micro-chip 1740 mounted to the distal end portion of the cartridge body 1710. In one arrangement, for example, each of the right and left flexible circuits 1730R, 1730L may have an overall width "CW" of approximately 0.025 inches and each of the electrodes 1736R, 1736L, 1738R, 1738R has a width "EW" of approximately 0.010 inches for example. See FIG. 13. However, other widths/sizes are contemplated and may be employed in alternative aspects.

Figure 14:
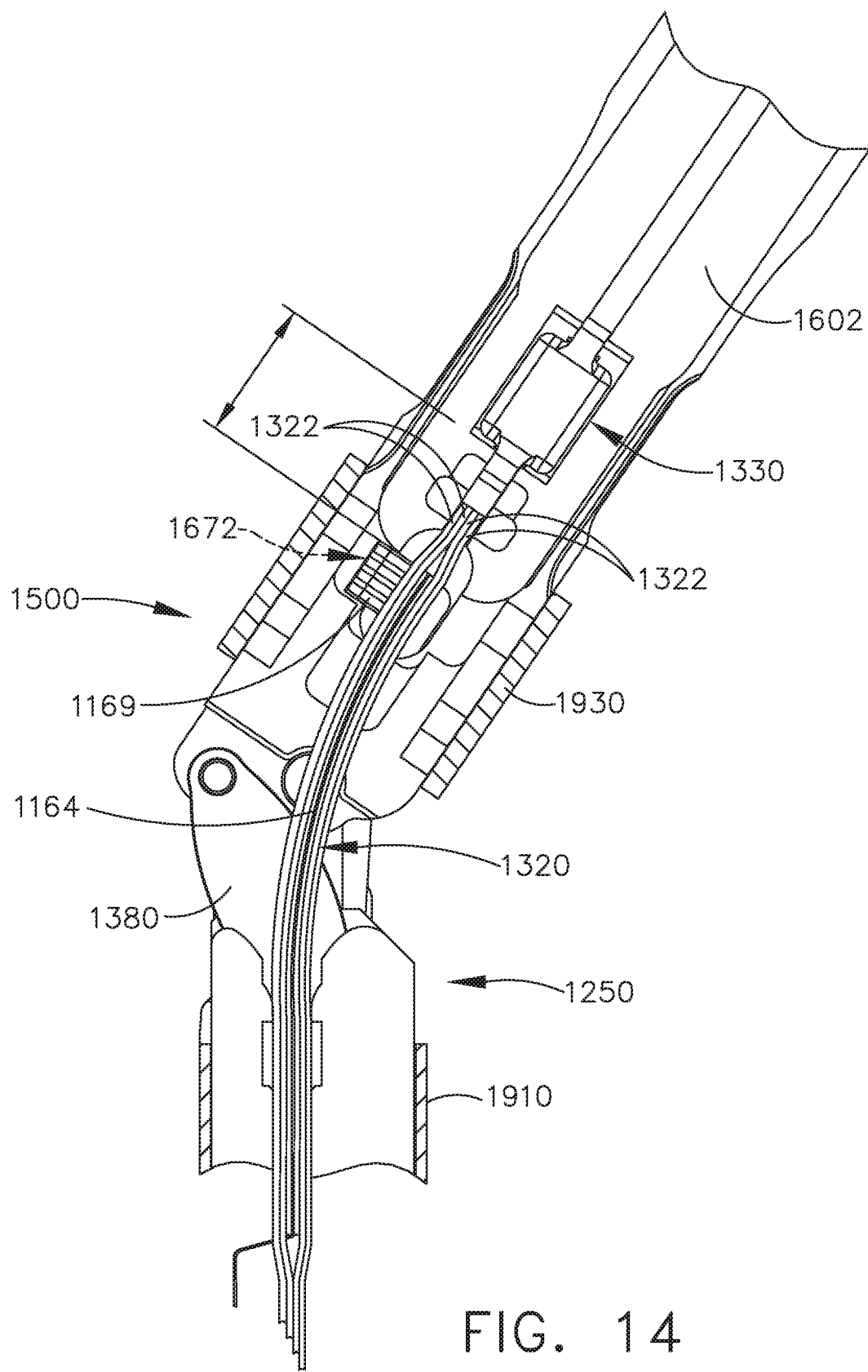
FIG. 14 is a top cross-sectional view of a portion of the interchangeable surgical tool assembly of FIGS. 1 and 5 with the end effector thereof in an articulated position according to one aspect of this disclosure.

In at least one arrangement, RF energy is supplied to the surgical tool assembly 1000 by a conventional RF generator 400 through a supply lead 402. In at least one arrangement, the supply lead 402 includes a male plug assembly 406 that is configured to be plugged into corresponding female connectors 410 that are attached to a segmented RF circuit 1160 on the an onboard circuit board 1152. See FIG. 15. Such arrangement facilitates rotational travel of the shaft and end effector 1500 about the shaft axis SA relative to the tool chassis 1210 by rotating the nozzle assembly 1240 without winding up the supply lead 402 from the generator 400. An onboard on/off power switch 420 is supported on the latch assembly 1280 and tool chassis 1210 for turning the RF generator on and off. When the tool assembly 1000 is operably coupled to the handle assembly 500 or robotic system, the onboard segmented RF circuit 1160 communicates with the microprocessor 560 through the connectors 1154 and 562. As shown in FIG. 1, the handle assembly 500 may also include a display screen 430 for viewing information about the progress of sealing, stapling, knife location, status of the cartridge, tissue, temperature, etc. As can also be seen FIG. 15, the slip ring assembly 1150 interfaces with a distal connector 1162 that includes a flexible shaft circuit strip or assembly 1164 that may include a plurality of narrow electrical conductors 1166 for stapling related activities and wider electrical conductors 1168 used for RF purposes. As shown in FIGS. 14 and 15, the flexible shaft circuit strip 1164 is centrally supported between the laminated plates or bars 1322 that form the knife bar 1320. Such arrangement facilitates sufficient flexing of the knife bar 1320 and flexible shaft circuit strip 1164 during articulation of the end effector 1500 while remaining sufficiently stiff so as to enable the knife member 1330 to be distally advanced through the clamped tissue.

Turning again to FIG. 10, in at least one illustrated arrangement, the elongate channel 1602 includes a channel circuit 1670 supported in a recess 1621 that extends from the proximal end 1610 of the elongate channel 1602 to a distal location 1623 in the elongate channel bottom portion 1620. The channel circuit 1670 includes a proximal contact portion 1672 that contacts a distal contact portion 1169 of the flexible shaft circuit strip 1164 for electrical contact therewith. A distal end 1674 of the channel circuit 1670 is received within a corresponding wall recess 1625 formed in one of the channel walls 1622 and is folded over and attached to an upper edge 1627 of the channel wall 1622. A series of corresponding exposed contacts 1676 are provided in the distal end 1674 of the channel circuit 1670 as shown in FIG. 10. As can also be seen in FIG. 10, an end 1752 of a flexible cartridge circuit 1750 is attached to the distal micro-chip 1740 and is affixed to the distal end portion of the cartridge body 1710. Another end 1754 is folded over the edge of the cartridge deck surface 1711 and includes exposed contacts 1756 configured to make electrical contact with the exposed contacts 1676 of the channel circuit 1670. Thus, when the RF cartridge 1700 is installed in the elongate channel 1602, the electrodes as well as the distal micro-chip 1740 are powered and communicate with the onboard circuit board 1152 through contact between the flexible cartridge circuit 1750, the flexible channel circuit 1670, the flexible shaft circuit 1164 and the slip ring assembly 1150.

Figure 16A:
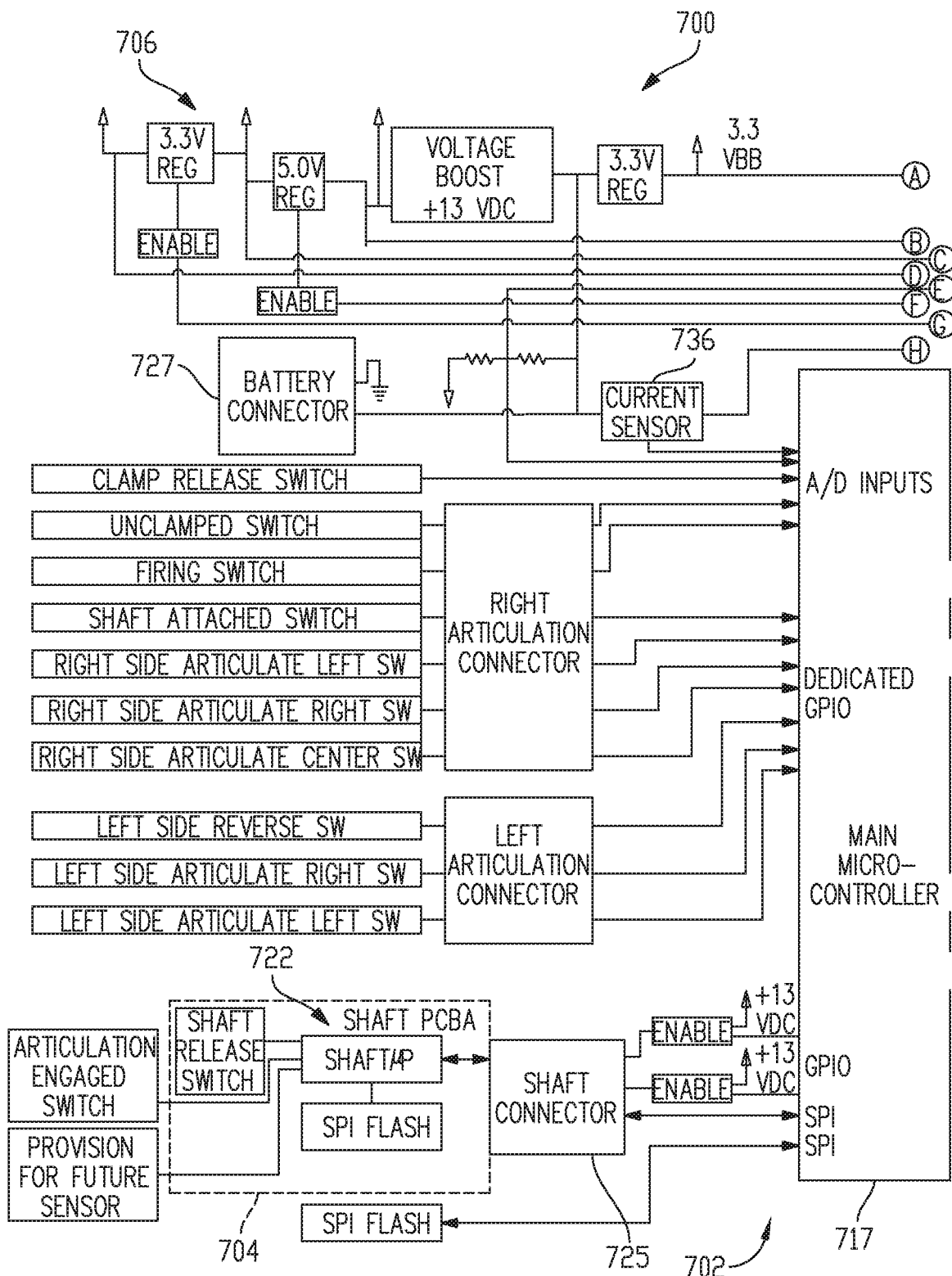
FIGS. 16A-16B is a block diagram of a control circuit of the surgical instrument of FIG. 1 spanning two drawing sheets according to one aspect of this disclosure.
Figure 16B:
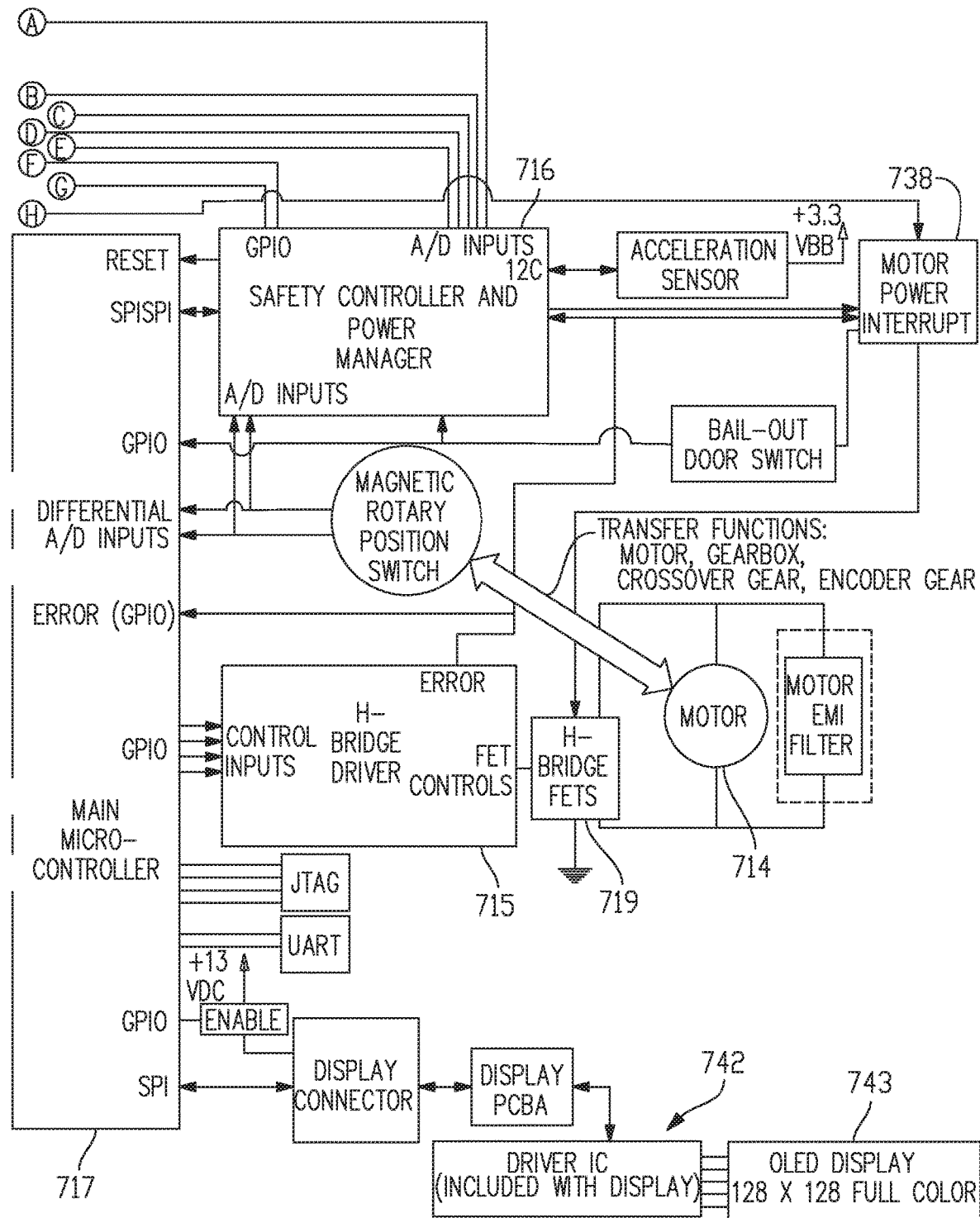

FIGS. 16A-16B is a block diagram of a control circuit 700 of the surgical instrument 10 of FIG. 1 spanning two drawing sheets according to one aspect of this disclosure. Referring primarily to FIGS. 16A-16B, a handle assembly 702 may include a motor 714 which can be controlled by a motor driver 715 and can be employed by the firing system of the surgical instrument 10. In various forms, the motor 714 may be a DC brushed driving motor having a maximum rotational speed of approximately 25,000 RPM. In other arrangements, the motor 714 may include a brushless motor, a cordless motor, a synchronous motor, a stepper motor, or any other suitable electric motor. The motor driver 715 may comprise an H-Bridge driver comprising field-effect transistors (FETs) 719, for example. The motor 714 can be powered by the power assembly 706 releasably mounted to the handle assembly 500 for supplying control power to the surgical instrument 10. The power assembly 706 may comprise a battery which may include a number of battery cells connected in series that can be used as the power source to power the surgical instrument 10. In certain circumstances, the battery cells of the power assembly 706 may be replaceable and/or rechargeable. In at least one example, the battery cells can be Lithium-Ion batteries which can be separably couplable to the power assembly 706.

The shaft assembly 704 may include a shaft assembly controller 722 which can communicate with a safety controller and power management controller 716 through an interface while the shaft assembly 704 and the power assembly 706 are coupled to the handle assembly 702. For example, the interface may comprise a first interface portion 725 which may include one or more electric connectors for coupling engagement with corresponding shaft assembly electric connectors and a second interface portion 727 which may include one or more electric connectors for coupling engagement with corresponding power assembly electric connectors to permit electrical communication between the shaft assembly controller 722 and the power management controller 716 while the shaft assembly 704 and the power assembly 706 are coupled to the handle assembly 702. One or more communication signals can be transmitted through the interface to communicate one or more of the power requirements of the attached interchangeable shaft assembly 704 to the power management controller 716. In response, the power management controller may modulate the power output of the battery of the power assembly 706, as described below in greater detail, in accordance with the power requirements of the attached shaft assembly 704. The connectors may comprise switches which can be activated after mechanical coupling engagement of the handle assembly 702 to the shaft assembly 704 and/or to the power assembly 706 to allow electrical communication between the shaft assembly controller 722 and the power management controller 716.

The interface can facilitate transmission of the one or more communication signals between the power management controller 716 and the shaft assembly controller 722 by routing such communication signals through a main controller 717 residing in the handle assembly 702, for example. In other circumstances, the interface can facilitate a direct line of communication between the power management controller 716 and the shaft assembly controller 722 through the handle assembly 702 while the shaft assembly 704 and the power assembly 706 are coupled to the handle assembly 702.

The main controller 717 may be any single core or multicore processor such as those known under the trade name ARM Cortex by Texas Instruments. In one aspect, the main controller 717 may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

The safety controller may be a safety controller platform comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The power assembly 706 may include a power management circuit which may comprise the power management controller 716, a power modulator 738, and a current sense circuit 736. The power management circuit can be configured to modulate power output of the battery based on the power requirements of the shaft assembly 704 while the shaft assembly 704 and the power assembly 706 are coupled to the handle assembly 702. The power management controller 716 can be programmed to control the power modulator 738 of the power output of the power assembly 706 and the current sense circuit 736 can be employed to monitor power output of the power assembly 706 to provide feedback to the power management controller 716 about the power output of the battery so that the power management controller 716 may adjust the power output of the power assembly 706 to maintain a desired output. The power management controller 716 and/or the shaft assembly controller 722 each may comprise one or more processors and/or memory units which may store a number of software modules.

The surgical instrument 10 (FIGS. 1-5) may comprise an output device 742 which may include devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 742 may comprise a display 743 which may be included in the handle assembly 702. The shaft assembly controller 722 and/or the power management controller 716 can provide feedback to a user of the surgical instrument 10 through the output device 742. The interface can be configured to connect the shaft assembly controller 722 and/or the power management controller 716 to the output device 742. The output device 742 can instead be integrated with the power assembly 706. In such circumstances, communication between the output device 742 and the shaft assembly controller 722 may be accomplished through the interface while the shaft assembly 704 is coupled to the handle assembly 702.

The control circuit 700 comprises circuit segments configured to control operations of the powered surgical instrument 10. A safety controller segment (Segment 1) comprises a safety controller and the main controller 717 segment (Segment 2). The safety controller and/or the main controller 717 are configured to interact with one or more additional circuit segments such as an acceleration segment, a display segment, a shaft segment, an encoder segment, a motor segment, and a power segment. Each of the circuit segments may be coupled to the safety controller and/or the main controller 717. The main controller 717 is also coupled to a flash memory. The main controller 717 also comprises a serial communication interface. The main controller 717 comprises a plurality of inputs coupled to, for example, one or more circuit segments, a battery, and/or a plurality of switches. The segmented circuit may be implemented by any suitable circuit, such as, for example, a printed circuit board assembly (PCBA) within the powered surgical instrument 10. It should be understood that the term processor as used herein includes any microprocessor, processors, controller, controllers, or other basic computing device that incorporates the functions of a computer's central processing unit (CPU) on an integrated circuit or at most a few integrated circuits. The main controller 717 is a multipurpose, programmable device that accepts digital data as input, processes it according to instructions stored in its memory, and provides results as output. It is an example of sequential digital logic, as it has internal memory. The control circuit 700 can be configured to implement one or more of the processes described herein.

The acceleration segment (Segment 3) comprises an accelerometer. The accelerometer is configured to detect movement or acceleration of the powered surgical instrument 10. Input from the accelerometer may be used to transition to and from a sleep mode, identify an orientation of the powered surgical instrument, and/or identify when the surgical instrument has been dropped. In some examples, the acceleration segment is coupled to the safety controller and/or the main controller 717.

The display segment (Segment 4) comprises a display connector coupled to the main controller 717. The display connector couples the main controller 717 to a display through one or more integrated circuit drivers of the display. The integrated circuit drivers of the display may be integrated with the display and/or may be located separately from the display. The display may comprise any suitable display, such as, for example, an organic light-emitting diode (OLED) display, a liquid-crystal display (LCD), and/or any other suitable display. In some examples, the display segment is coupled to the safety controller.

The shaft segment (Segment 5) comprises controls for an interchangeable shaft assembly 500 coupled to the surgical instrument 10 (FIGS. 1-5) and/or one or more controls for an end effector 1500 coupled to the interchangeable shaft assembly 500. The shaft segment comprises a shaft connector configured to couple the main controller 717 to a shaft PCBA. The shaft PCBA comprises a low-power microcontroller with a ferroelectric random access memory (FRAM), an articulation switch, a shaft release Hall effect switch, and a shaft PCBA EEPROM. The shaft PCBA EEPROM comprises one or more parameters, routines, and/or programs specific to the interchangeable shaft assembly 500 and/or the shaft PCBA. The shaft PCBA may be coupled to the interchangeable shaft assembly 500 and/or integral with the surgical instrument 10. In some examples, the shaft segment comprises a second shaft EEPROM. The second shaft EEPROM comprises a plurality of algorithms, routines, parameters, and/or other data corresponding to one or more shaft assemblies 500 and/or end effectors 1500 that may be interfaced with the powered surgical instrument 10.

The position encoder segment (Segment 6) comprises one or more magnetic angle rotary position encoders. The one or more magnetic angle rotary position encoders are configured to identify the rotational position of the motor 714, an interchangeable shaft assembly 500, and/or an end effector 1500 of the surgical instrument 10 (FIGS. 1-5). In some examples, the magnetic angle rotary position encoders may be coupled to the safety controller and/or the main controller 717.

The motor circuit segment (Segment 7) comprises a motor 714 configured to control movements of the powered surgical instrument 10 (FIGS. 1-5). The motor 714 is coupled to the main microcontroller processor 717 by an H-bridge driver comprising one or more H-bridge field-effect transistors (FETs) and a motor controller. The H-bridge driver is also coupled to the safety controller. A motor current sensor is coupled in series with the motor to measure the current draw of the motor. The motor current sensor is in signal communication with the main controller 717 and/or the safety controller. In some examples, the motor 714 is coupled to a motor electromagnetic interference (EMI) filter.

The motor controller controls a first motor flag and a second motor flag to indicate the status and position of the motor 714 to the main controller 717. The main controller 717 provides a pulse-width modulation (PWM) high signal, a PWM low signal, a direction signal, a synchronize signal, and a motor reset signal to the motor controller through a buffer. The power segment is configured to provide a segment voltage to each of the circuit segments.

The power segment (Segment 8) comprises a battery coupled to the safety controller, the main controller 717, and additional circuit segments. The battery is coupled to the segmented circuit by a battery connector and a current sensor. The current sensor is configured to measure the total current draw of the segmented circuit. In some examples, one or more voltage converters are configured to provide predetermined voltage values to one or more circuit segments. For example, in some examples, the segmented circuit may comprise 3.3V voltage converters and/or 5V voltage converters. A boost converter is configured to provide a boost voltage up to a predetermined amount, such as, for example, up to 13V. The boost converter is configured to provide additional voltage and/or current during power intensive operations and prevent brownout or low-power conditions.

A plurality of switches are coupled to the safety controller and/or the main controller 717. The switches may be configured to control operations of the surgical instrument 10 (FIGS. 1-5), of the segmented circuit, and/or indicate a status of the surgical instrument 10. A bail-out door switch and Hall effect switch for bailout are configured to indicate the status of a bail-out door. A plurality of articulation switches, such as, for example, a left side articulation left switch, a left side articulation right switch, a left side articulation center switch, a right side articulation left switch, a right side articulation right switch, and a right side articulation center switch are configured to control articulation of an interchangeable shaft assembly 500 (FIGS. 1 and 3) and/or the end effector 300 (FIGS. 1 and 4). A left side reverse switch and a right side reverse switch are coupled to the main controller 717. The left side switches comprising the left side articulation left switch, the left side articulation right switch, the left side articulation center switch, and the left side reverse switch are coupled to the main controller 717 by a left flex connector. The right side switches comprising the right side articulation left switch, the right side articulation right switch, the right side articulation center switch, and the right side reverse switch are coupled to the main controller 717 by a right flex connector. A firing switch, a clamp release switch, and a shaft engaged switch are coupled to the main controller 717.

Any suitable mechanical, electromechanical, or solid state switches may be employed to implement the plurality of switches, in any combination. For example, the switches may be limit switches operated by the motion of components associated with the surgical instrument 10 (FIGS. 1-5) or the presence of an object. Such switches may be employed to control various functions associated with the surgical instrument 10. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches may be solid state switches that operate under the influence of a magnetic field such as Hall-effect devices, magneto-resistive (MR) devices, giant magneto-resistive (GMR) devices, magnetometers, among others. In other implementations, the switches may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). Other switches may include electrical conductorless switches, ultrasonic switches, accelerometers, inertial sensors, among others.

Figure 17:
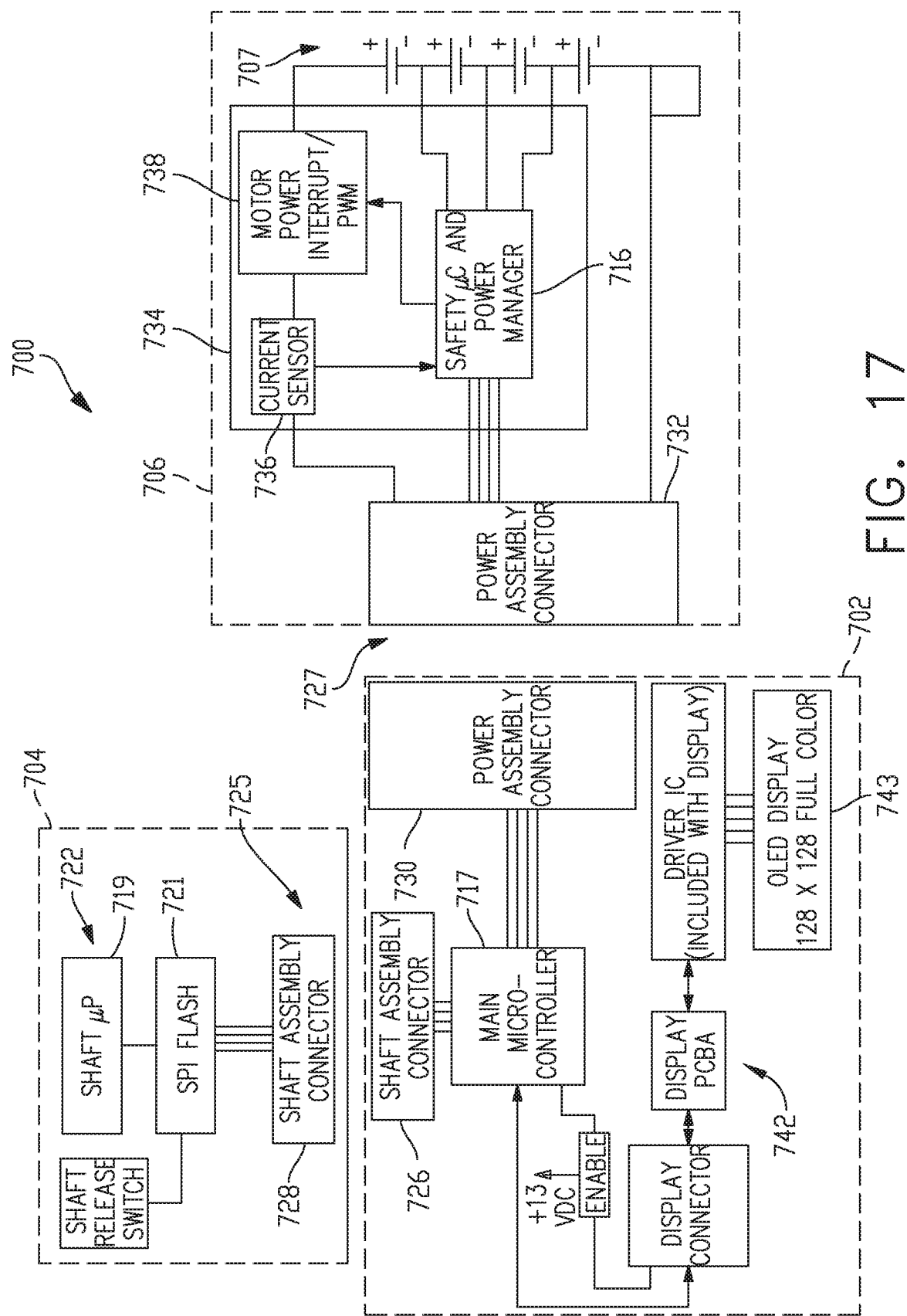
FIG. 17 is a block diagram of the control circuit of the surgical instrument of FIG. 1 illustrating interfaces between the handle assembly, the power assembly, and the handle assembly and the interchangeable shaft assembly according to one aspect of this disclosure.

FIG. 17 is another block diagram of the control circuit 700 of the surgical instrument of FIG. 1 illustrating interfaces between the handle assembly 702 and the power assembly 706 and between the handle assembly 702 and the interchangeable shaft assembly 704 according to one aspect of this disclosure. The handle assembly 702 may comprise a main controller 717, a shaft assembly connector 726 and a power assembly connector 730. The power assembly 706 may include a power assembly connector 732, a power management circuit 734 that may comprise the power management controller 716, a power modulator 738, and a current sense circuit 736. The shaft assembly connectors 730, 732 form an interface 727. The power management circuit 734 can be configured to modulate power output of the battery 707 based on the power requirements of the interchangeable shaft assembly 704 while the interchangeable shaft assembly 704 and the power assembly 706 are coupled to the handle assembly 702. The power management controller 716 can be programmed to control the power modulator 738 of the power output of the power assembly 706 and the current sense circuit 736 can be employed to monitor power output of the power assembly 706 to provide feedback to the power management controller 716 about the power output of the battery 707 so that the power management controller 716 may adjust the power output of the power assembly 706 to maintain a desired output. The shaft assembly 704 comprises a shaft processor 719 coupled to a non-volatile memory 721 and shaft assembly connector 728 to electrically couple the shaft assembly 704 to the handle assembly 702. The shaft assembly connectors 726, 728 form interface 725. The main controller 717, the shaft processor 719, and/or the power management controller 716 can be configured to implement one or more of the processes described herein.

The surgical instrument 10 (FIGS. 1-5) may comprise an output device 742 to a sensory feedback to a user. Such devices may comprise visual feedback devices (e.g., an LCD display screen, LED indicators), audio feedback devices (e.g., a speaker, a buzzer), or tactile feedback devices (e.g., haptic actuators). In certain circumstances, the output device 742 may comprise a display 743 that may be included in the handle assembly 702. The shaft assembly controller 722 and/or the power management controller 716 can provide feedback to a user of the surgical instrument 10 through the output device 742. The interface 727 can be configured to connect the shaft assembly controller 722 and/or the power management controller 716 to the output device 742. The output device 742 can be integrated with the power assembly 706. Communication between the output device 742 and the shaft assembly controller 722 may be accomplished through the interface 725 while the interchangeable shaft assembly 704 is coupled to the handle assembly 702. Having described a control circuit 700 (FIGS. 16A-16B and 6) for controlling the operation of the surgical instrument 10 (FIGS. 1-5), the disclosure now turns to various configurations of the surgical instrument 10 (FIGS. 1-5) and control circuit 700.

Figure 18:
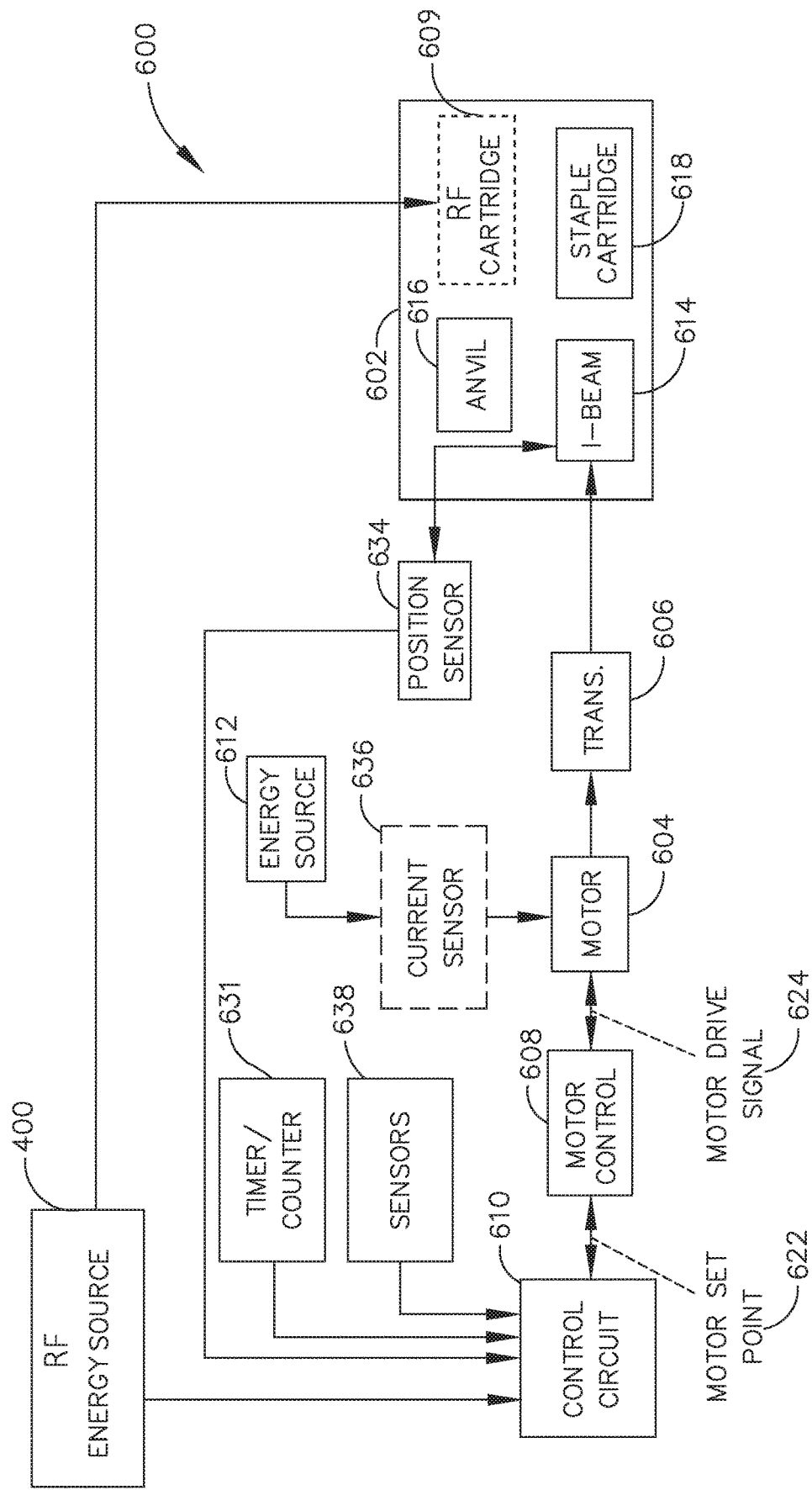
FIG. 18 is a schematic diagram of a surgical instrument configured to control various functions according to one aspect of this disclosure.

FIG. 18 is a schematic diagram of a surgical instrument 600 configured to control various functions according to one aspect of this disclosure. In one aspect, the surgical instrument 600 is programmed to control distal translation of a displacement member such as the I-beam 614. The surgical instrument 600 comprises an end effector 602 that may comprise an anvil 616, an I-beam 614, and a removable staple cartridge 618 which may be interchanged with an RF cartridge 609 (shown in dashed line). The end effector 602, anvil 616, I-beam 614, staple cartridge 618, and RF cartridge 609 may be configured as described herein, for example, with respect to FIGS. 1-15. For conciseness and clarity of disclosure, several aspects of the present disclosure may be described with reference to FIG. 18. It will be appreciated that the components shown schematically in FIG. 18 such as the control circuit 610, sensors 638, position sensor 634, end effector 602, I-beam 614, staple cartridge 618, RF cartridge 609, anvil 616, are described in connection with FIGS. 1-17 of this disclosure.

Accordingly, the components represented schematically in FIG. 18 may be readily substituted with the physical and functional equivalent components described in connection with FIGS. 1-17. For example, in one aspect, the control circuit 610 may be implemented as the control circuit 700 shown and described in connection with FIGS. 16-17. In one aspect, the sensors 638 may be implemented as a limit switch, electromechanical device, solid state switches, Hall-effect devices, magneto-resistive (MR) devices, giant magneto-resistive (GMR) devices, magnetometers, among others. In other implementations, the sensors 638 may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). In other implementations, the sensors 638 may include electrical conductorless switches, ultrasonic switches, accelerometers, inertial sensors, among others. In one aspect, the position sensor 634 may be implemented as an absolute positioning system comprising a magnetic rotary absolute positioning system implemented as an AS5055EQFT single-chip magnetic rotary position sensor available from Austria Microsystems, AG. The position sensor 634 may interface with the control circuit 700 to provide an absolute positioning system. The position may include multiple Hall-effect elements located above a magnet and coupled to a CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. In one aspect, the end effector 602 may be implemented as surgical end effector 1500 shown and described in connection with FIGS. 1, 2, and 4. In one aspect, the I-beam 614 may be implemented as the knife member 1330 comprising a knife body 1332 that operably supports a tissue cutting blade 1334 thereon and may further include anvil engagement tabs or features 1336 and channel engagement features or a foot 1338 as shown and described in connection with FIGS. 2-4, 8, 11 and 14. In one aspect, the staple cartridge 618 may be implemented as the standard (mechanical) surgical fastener cartridge 1400 shown and described in connection with FIG. 4. In one aspect, the RF cartridge 609 may be implemented as the radio frequency (RF) cartridge 1700 shown and described in connection with FIGS. 1, 2, 6, and 10-13. In one aspect, the anvil 616 may be implemented the anvil 1810 shown and described in connection with FIGS. 1, 2, 4, and 6. These and other sensors arrangements are described in commonly owned U.S. patent application Ser. No. 15/628,175, entitled TECHNIQUES FOR ADAPTIVE CONTROL OF MOTOR VELOCITY OF A SURGICAL STAPLING AND CUTTING INSTRUMENT, which is incorporated herein by reference in its entirety.

The position, movement, displacement, and/or translation of a linear displacement member, such as the I-beam 614, can be measured by an absolute positioning system, sensor arrangement, and position sensor represented as position sensor 634. Because the I-beam 614 is coupled to the longitudinally movable drive member 540, the position of the I-beam 614 can be determined by measuring the position of the longitudinally movable drive member 540 employing the position sensor 634. Accordingly, in the following description, the position, displacement, and/or translation of the I-beam 614 can be achieved by the position sensor 634 as described herein. A control circuit 610, such as the control circuit 700 described in FIGS. 16A and 16B, may be programmed to control the translation of the displacement member, such as the I-beam 614, as described herein. The control circuit 610, in some examples, may comprise one or more microcontrollers, microprocessors, or other suitable processors for executing instructions that cause the processor or processors to control the displacement member, e.g., the I-beam 614, in the manner described. In one aspect, a timer/counter circuit 631 provides an output signal, such as elapsed time or a digital count, to the control circuit 610 to correlate the position of the I-beam 614 as determined by the position sensor 634 with the output of the timer/counter circuit 631 such that the control circuit 610 can determine the position of the I-beam 614 at a specific time (t) relative to a starting position. The timer/counter circuit 631 may be configured to measure elapsed time, count external evens, or time external events.

The control circuit 610 may generate a motor set point signal 622. The motor set point signal 622 may be provided to a motor controller 608. The motor controller 608 may comprise one or more circuits configured to provide a motor drive signal 624 to the motor 604 to drive the motor 604 as described herein. In some examples, the motor 604 may be a brushed DC electric motor, such as the motor 505 shown in FIG. 1. For example, the velocity of the motor 604 may be proportional to the motor drive signal 624. In some examples, the motor 604 may be a brushless direct current (DC) electric motor and the motor drive signal 624 may comprise a pulse-width-modulated (PWM) signal provided to one or more stator windings of the motor 604. Also, in some examples, the motor controller 608 may be omitted and the control circuit 610 may generate the motor drive signal 624 directly.

The motor 604 may receive power from an energy source 612. The energy source 612 may be or include a battery, a super capacitor, or any other suitable energy source 612. The motor 604 may be mechanically coupled to the I-beam 614 via a transmission 606. The transmission 606 may include one or more gears or other linkage components to couple the motor 604 to the I-beam 614. A position sensor 634 may sense a position of the I-beam 614. The position sensor 634 may be or include any type of sensor that is capable of generating position data that indicates a position of the I-beam 614. In some examples, the position sensor 634 may include an encoder configured to provide a series of pulses to the control circuit 610 as the I-beam 614 translates distally and proximally. The control circuit 610 may track the pulses to determine the position of the I-beam 614. Other suitable position sensor may be used, including, for example, a proximity sensor. Other types of position sensors may provide other signals indicating motion of the I-beam 614. Also, in some examples, the position sensor 634 may be omitted. Where the motor 604 is a stepper motor, the control circuit 610 may track the position of the I-beam 614 by aggregating the number and direction of steps that the motor 604 has been instructed to execute. The position sensor 634 may be located in the end effector 602 or at any other portion of the instrument.

The control circuit 610 may be in communication with one or more sensors 638. The sensors 638 may be positioned on the end effector 602 and adapted to operate with the surgical instrument 600 to measure the various derived parameters such as gap distance versus time, tissue compression versus time, and anvil strain versus time. The sensors 638 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 602. The sensors 638 may include one or more sensors.

The one or more sensors 638 may comprise a strain gauge, such as a micro-strain gauge, configured to measure the magnitude of the strain in the anvil 616 during a clamped condition. The strain gauge provides an electrical signal whose amplitude varies with the magnitude of the strain. The sensors 638 may comprise a pressure sensor configured to detect a pressure generated by the presence of compressed tissue between the anvil 616 and the staple cartridge 618. The sensors 638 may be configured to detect impedance of a tissue section located between the anvil 616 and the staple cartridge 618 that is indicative of the thickness and/or fullness of tissue located therebetween.

The sensors 638 may be is configured to measure forces exerted on the anvil 616 by the closure drive system. For example, one or more sensors 638 can be at an interaction point between the closure tube 1910 (FIGS. 1-4) and the anvil 616 to detect the closure forces applied by the closure tube 1910 to the anvil 616. The forces exerted on the anvil 616 can be representative of the tissue compression experienced by the tissue section captured between the anvil 616 and the staple cartridge 618. The one or more sensors 638 can be positioned at various interaction points along the closure drive system to detect the closure forces applied to the anvil 616 by the closure drive system. The one or more sensors 638 may be sampled in real time during a clamping operation by a processor as described in FIGS. 16A-16B. The control circuit 610 receives real-time sample measurements to provide analyze time based information and assess, in real time, closure forces applied to the anvil 616.

A current sensor 636 can be employed to measure the current drawn by the motor 604. The force required to advance the I-beam 614 corresponds to the current drawn by the motor 604. The force is converted to a digital signal and provided to the control circuit 610.

The RF energy source 400 is coupled to the end effector 602 and is applied to the RF cartridge 609 when the RF cartridge 609 is loaded in the end effector 602 in place of the staple cartridge 618. The control circuit 610 controls the delivery of the RF energy to the RF cartridge 609.

In various aspects, the surgical instrument can include one or more sensors that are configured to measure a variety of different parameters associated with the operation of the surgical instrument. Such parameters can include the status of the RF energy applied by the surgical instrument, the temperature of the tissue being sealed by the surgical instrument, the water content of the tissue, the operational status of the surgical instrument, and the thickness of the clamped tissue. The surgical instrument can be configured to monitor these various parameters and present information associated with them to the operator of the instrument via, for example, the display 430 (FIG. 1). In various aspects, the display 430 can present the monitored parameters to the operator via a graphical display.

Figure 19:
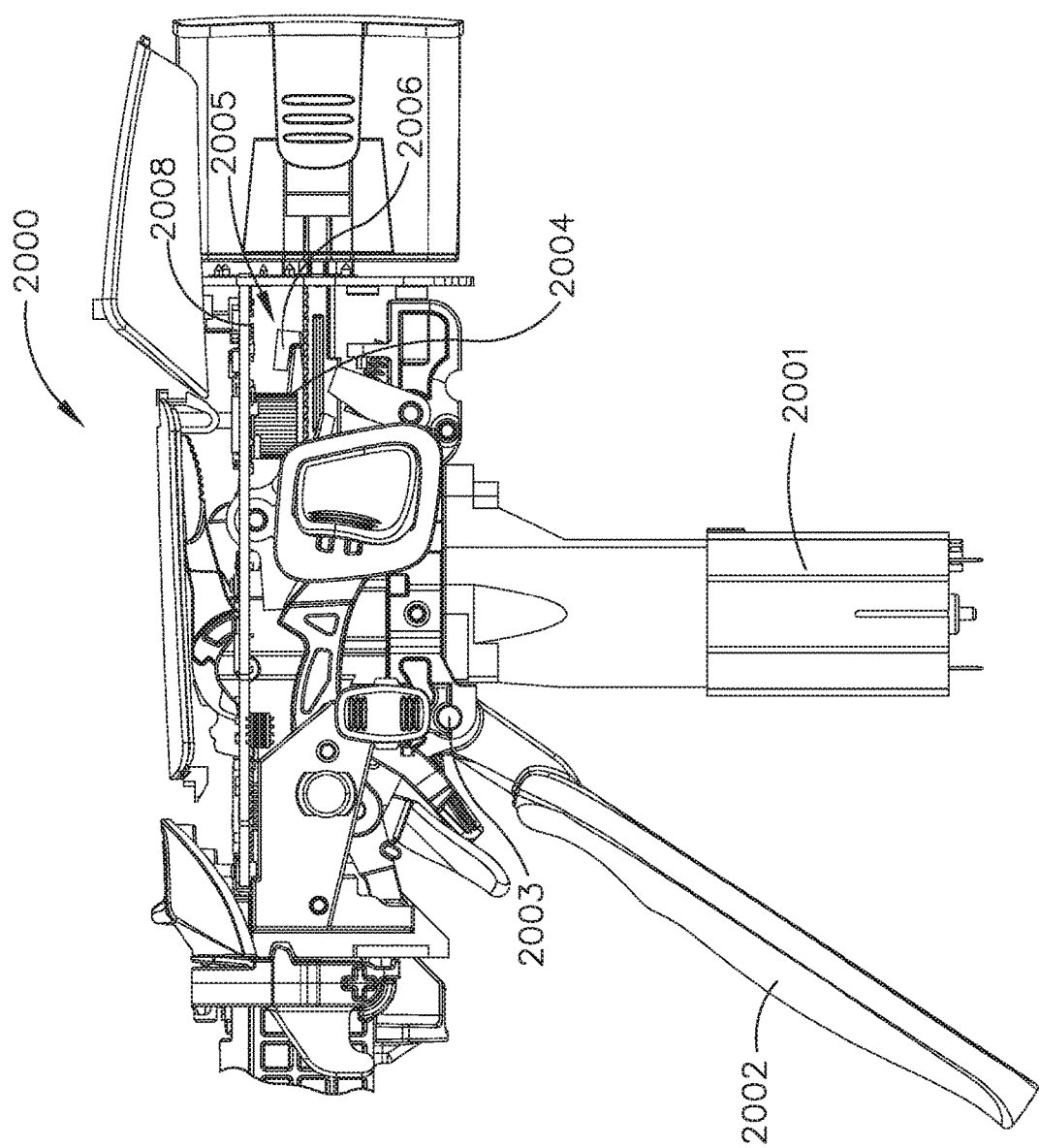
FIG. 19 is side elevational view of the surgical instrument with the casing removed displaying a trigger sensing assembly, wherein the closure trigger is in the unactuated position according to one aspect of this disclosure.
Figure 20:
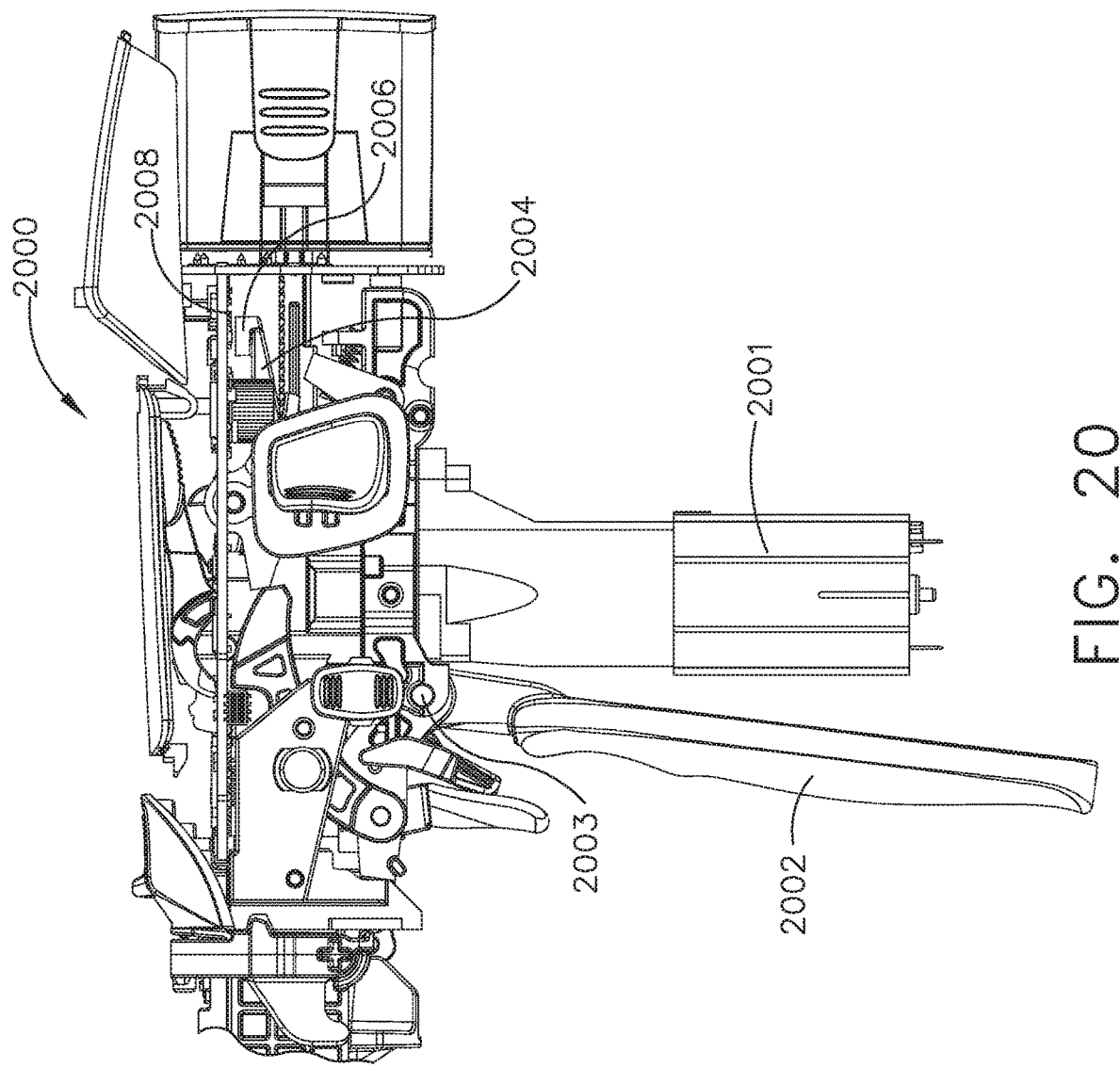
FIG. 20 is a side elevational view of the surgical instrument with the casing removed displaying a trigger sensing assembly, wherein the closure trigger is in the actuated position according to one aspect of this disclosure.

In some aspects, the surgical instrument can include a sensor or sensor assembly configured to detect the position of the closure trigger, i.e., whether the closure trigger is actuated. One such aspect is depicted in FIGS. 19-20, which are side elevational views of the surgical instrument 2000 with the casing removed, wherein the closure trigger 2002 is alternatively in the actuated and unactuated positions, in accordance with one or more aspects of the present disclosure. As described in more detail above, the unactuated position of the closure trigger 2002 is associated with an open or unclamped position for the end effector 1500 (FIG. 1) in which tissue can be positioned between the jaws 1600, 1800 and the actuated position of the closure trigger 2002 is associated with a closed or clamped position for the end effector 1500 in which tissue can be clamped between the jaws 1600, 1800. The closure trigger 2002 can comprise an arm 2004 that is connected either directly thereto or indirectly thereto via a mechanical linkage, such that the arm 2004 rotates upon actuation of the closure trigger 2002. In one aspect, a trigger sensing assembly 2005 comprises a magnetic element 2006, such as a permanent magnet, disposed at a distal end of the arm 2004 and a sensor 2008 that is configured to detect the movement of the magnetic element 2006. The sensor 2008 can comprise, for example, a Hall effect sensor configured to detect changes in a magnetic field surrounding the Hall effect sensor caused by the movement of the magnetic element 2006. As the sensor 2008 can detect the movement of the magnetic element 2006 and the movement of the magnetic element 2006 corresponds to the position of the closure trigger 2002 in a known manner, the trigger sensing assembly 2005 can therefore detect whether the closure trigger 2002 is in the actuated position, the unactuated position, or another position therebetween.

In another aspect, the trigger sensing assembly 2005 comprises a sensor or switch that is tripped when the closure drive system 510 (FIG. 1) locks the closure trigger 2002 into the fully depressed or fully actuated position. In such an aspect, the switch can generate a signal indicating that the lock is engaged and thus that the closure trigger 2002 is fully depressed.

In another aspect described in U.S. Patent Application Pub. No. 2014/0296874, entitled ROBOTICALLY-CONTROLLED END EFFECTOR, which is incorporated by reference in its entirety, the trigger sensing assembly 2005 comprises a force sensor positioned between the closure trigger 2002 and the pivot pin 2003 about which the closure trigger 2002 pivots. In this aspect, pulling the closure trigger 2002 towards the pistol grip portion 2001 causes the closure trigger 512 to exert a force on the pivot pin 2003. The force sensor is configured to detect this force and generate a signal in response thereto.

The trigger sensing assembly 2005 can be in signal communication with a controller 2102 (FIG. 25) via a wired or wireless connection such that any signal generated by the trigger sensing assembly 2005 is relayed to the controller 2102. The trigger sensing assembly 2005 can be configured to continuously monitor the position of the closure trigger 2002 throughout the operation of the instrument by sampling the sensed parameter(s) or transmitting a feedback signal indicative of the sensed parameter(s) with a minimal time delay. In various aspects, the trigger sensing assembly 2005 can comprise an analog sensor configured to generate a signal corresponding to the degree of force exerted on the closure trigger 2002 and/or a particular position of the closure trigger 2002. In such aspects, an analog-to-digital converter may be positioned between the trigger sensing assembly 2005 and the controller 2102. In various other aspects, the trigger sensing assembly 2005 can comprise a digital sensor configured to generate a signal indicative only of whether the closure trigger 2002 is actuated or unactuated.

Figure 21:
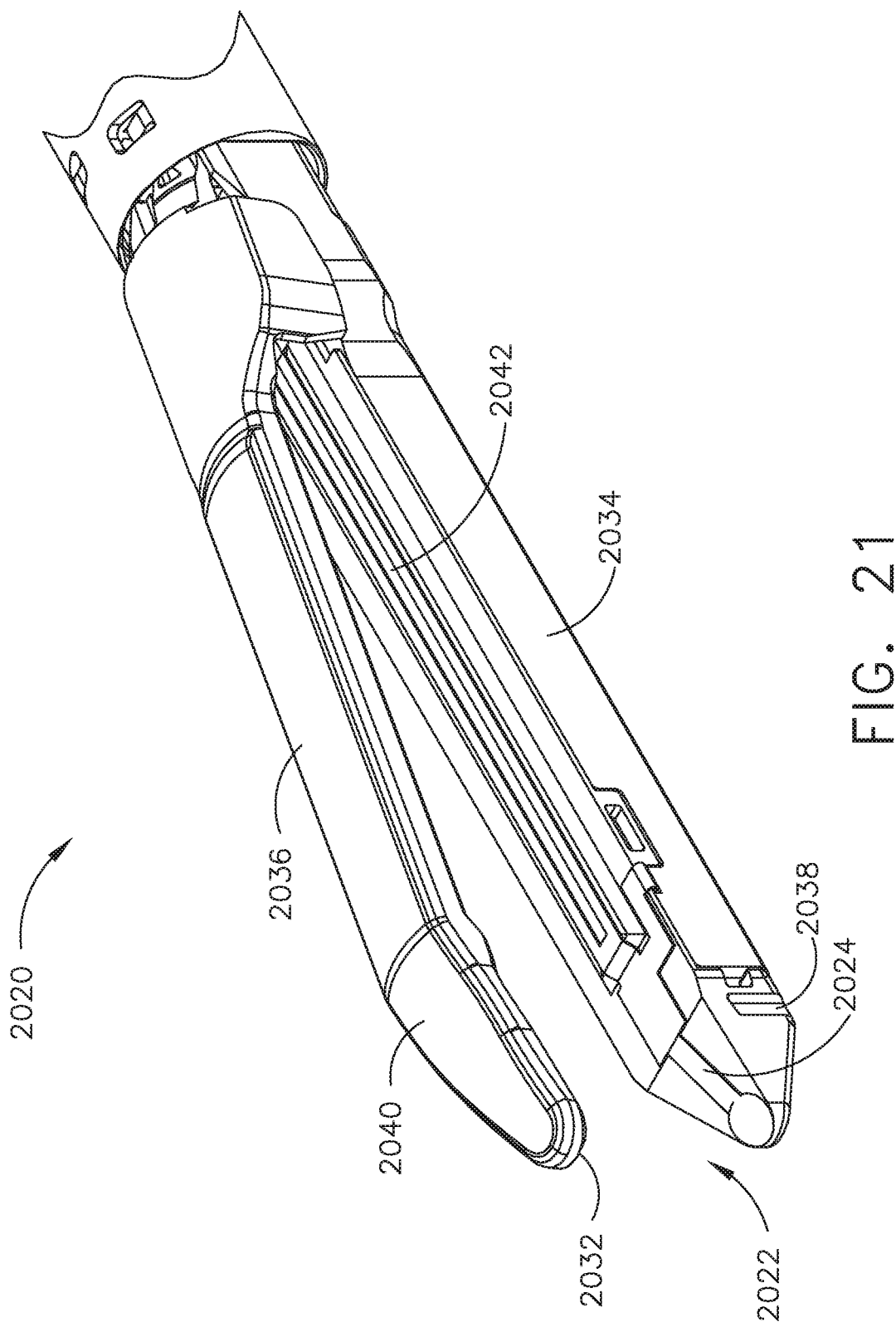
FIG. 21 is a perspective view of an end effector comprising a tissue thickness sensing assembly according to one aspect of this disclosure.
Figure 22:
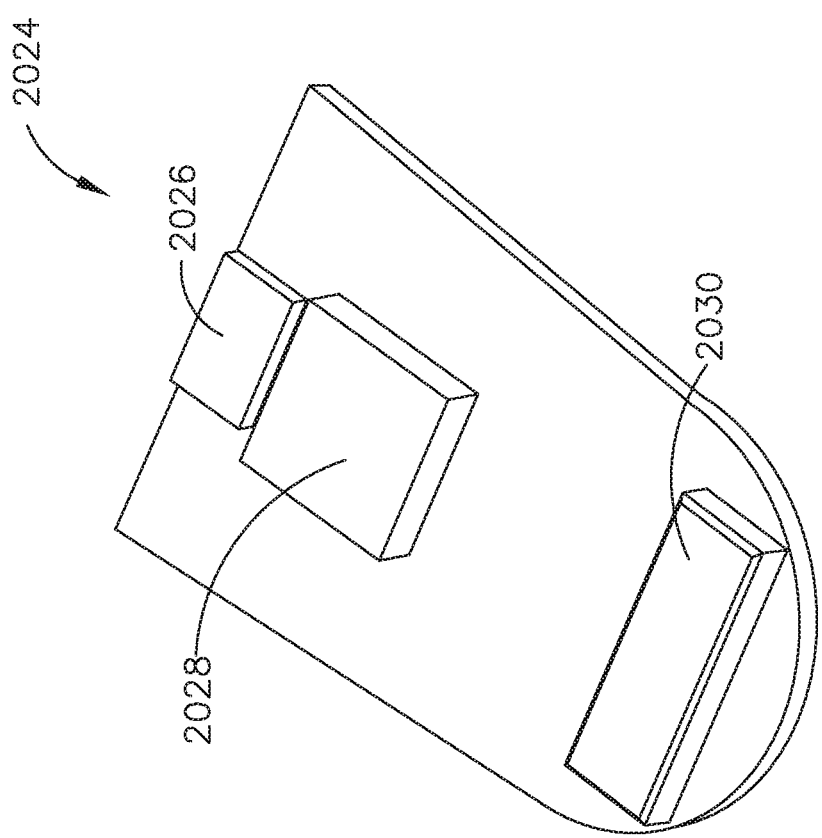
FIG. 22 is a schematic view of a sensor of the tissue thickness sensing assembly according to one aspect of this disclosure.

In some aspects, the surgical instrument can include a sensor or sensor assembly that is configured to detect the thickness of tissue clamped by the end effector. One such aspect is depicted in FIGS. 21-22, which are a perspective view of an end effector 2020 comprising a tissue thickness sensing assembly 2022 and a schematic view of a sensor 2024 of the tissue thickness sensing assembly 2022, in accordance with one or more aspects of the present disclosure. The tissue thickness sensing assembly 2022 can comprise a sensor 2024 disposed on a first jaw 2034 or RF cartridge 2042 and a magnetic element 2032, such as a permanent magnet, disposed on a second jaw 2036 of the end effector 2020. In one aspect, the sensor 2024 is disposed at or adjacent to the distal end 2038 of the first jaw 2034, such that it is positioned distally with respect to the electrodes of the RF cartridge, and the magnetic element 2032 is correspondingly disposed at or adjacent to the distal end 2040 of the second jaw 2036. The sensor 2024 can comprise a magnetic field sensing element 2026 that is configured to detect the movement of the magnetic element 2006, such as a Hall effect sensor configured to detect changes in a magnetic field surrounding the Hall effect sensor caused by the movement of the magnetic element 2032. When the operator closes the end effector 2020, the magnetic element 2032 rotates downwardly closer to the magnetic field sensing element 2026, thereby varying the magnetic field detected by the magnetic field sensing element 2026 as the jaw or jaws rotate into the closed (or clamped position). The strength of the magnetic field from the magnetic element 2032 sensed by the magnetic field sensing element 2026 is indicative of the distance between the first jaw 2034 and the second jaw 2036, which in turn is indicative of the thickness of the tissue clamped therebetween. For instance, a larger distance between the first jaw 2034 and the second jaw 2036, and therefore a weaker magnetic field detected by the magnetic field sensing element 2026, may indicate that thick tissue is present between the first jaw 2034 and the second jaw 2036. Conversely, a shorter distance between the first jaw 2034 and the second jaw 2036, and therefore a stronger magnetic field detected by the magnetic field sensing element 2026, may indicate that thin tissue is present between the first jaw 2034 and the second jaw 2036. The magnetic field sensing element 2026 can be configured to detect and generate a signal corresponding to the relative or absolute strength of the sensed magnetic field, thereby allowing the surgical instrument to detect the relative or absolute thickness of the clamped tissue according to the resolution of the magnetic field sending elements 2026.

In another aspect, the tissue thickness sensing assembly 2022 can comprise a displacement sensor that is disposed at the pivot joint between the first jaw 2034 and the second jaw 2036. In this aspect, the displacement sensor is configured to detect the position of the jaws 2034, 2036 relative to each other, which in turn is indicative of the thickness of the tissue grasped therebetween when the end effector 2020 is in the clamped position. For example, in one aspect described in U.S. Patent Application Pub. No. 2014/0296874 wherein the anvil 1810 comprises pivot pins that are received within corresponding openings disposed on the elongate channel (FIG. 4), the tissue thickness sensing assembly 2022 can comprise a sensor positioned adjacent to, or within, the openings of the elongate channel 1602. In this aspect, as the anvil 1810 is closed, the pivot pins slide through the openings and into contact with the sensor, causing the sensor to generate a signal indicating that the anvil 1810 is closed.

In other aspects, the tissue thickness sensing assembly 2022 can further comprise a reed switch sensor, a displacement sensor, an optical sensor, a magneto-inductive sensor, a force sensor, a pressure sensor, a piezo-resistive film sensor, an ultrasonic sensor, an eddy current sensor, an accelerometer, a pulse oximetry sensor, a temperature sensor, a sensor configured to detect an electrical characteristic of a tissue path (such as capacitance or resistance), or any combination thereof. In one such aspect, the tissue thickness sensing assembly 2022 can comprise a first electrical sensor disposed on the first jaw 2034 and a corresponding second electrical sensor disposed on the second jaw 2036, wherein the first sensor is configured to transmit an electrical current that is detected by the second sensor through tissue captured by the end effector 2020. The detected current can be utilized by the tissue thickness sensing assembly 2022 to determine the thickness of the clamped tissue as tissue resistivity is a function of its thickness (and tissue type, among a variety of other factors).

The tissue thickness sensing assembly 2022 can be in signal communication with a controller 2102 via a wired or wireless connection such that any signal generated by the tissue thickness sensing assembly 2022 is relayed to the controller 2102. For example, the tissue thickness sensing assembly 2022 can comprise a transmitter 2028 configured to transmit the signals generated by the magnetic field sensing element 2026 via a wired or wireless connection to a receiver, which in turn is communicably coupled to the controller 2102. The tissue thickness sensing assembly 2022 can be configured to continuously monitor the thickness of the clamped tissue throughout the operation of the instrument by sampling the sensed parameter(s) or transmitting a feedback signal indicative of the sensed parameter(s) with a minimal time delay. In various aspects, the tissue thickness sensing assembly 2022 can comprise an analog sensor configured to generate a signal corresponding to relative or absolute thickness of the clamped tissue and/or a particular position of either of the first jaw 2034 or the second jaw 2036. In such aspects, an analog-to-digital converter may be positioned between the tissue thickness sensing assembly 2022 and the controller 2102. In various other aspects, the tissue thickness sensing assembly 2022 can comprise a digital sensor configured to generate a signal indicative only of whether the jaws 2034, 2036 are opened or closed.

In some aspects, the tissue thickness sensing assembly 2022 can further comprise a power source 2030 operably connected to the magnetic field sensing element 2026. The power source 2030 can be separate from any other power source associated with the surgical instrument. Alternatively, the issue thickness sensing assembly 2022 can be interconnected with one or more power sources associated with the surgical instrument.

Figure 23:
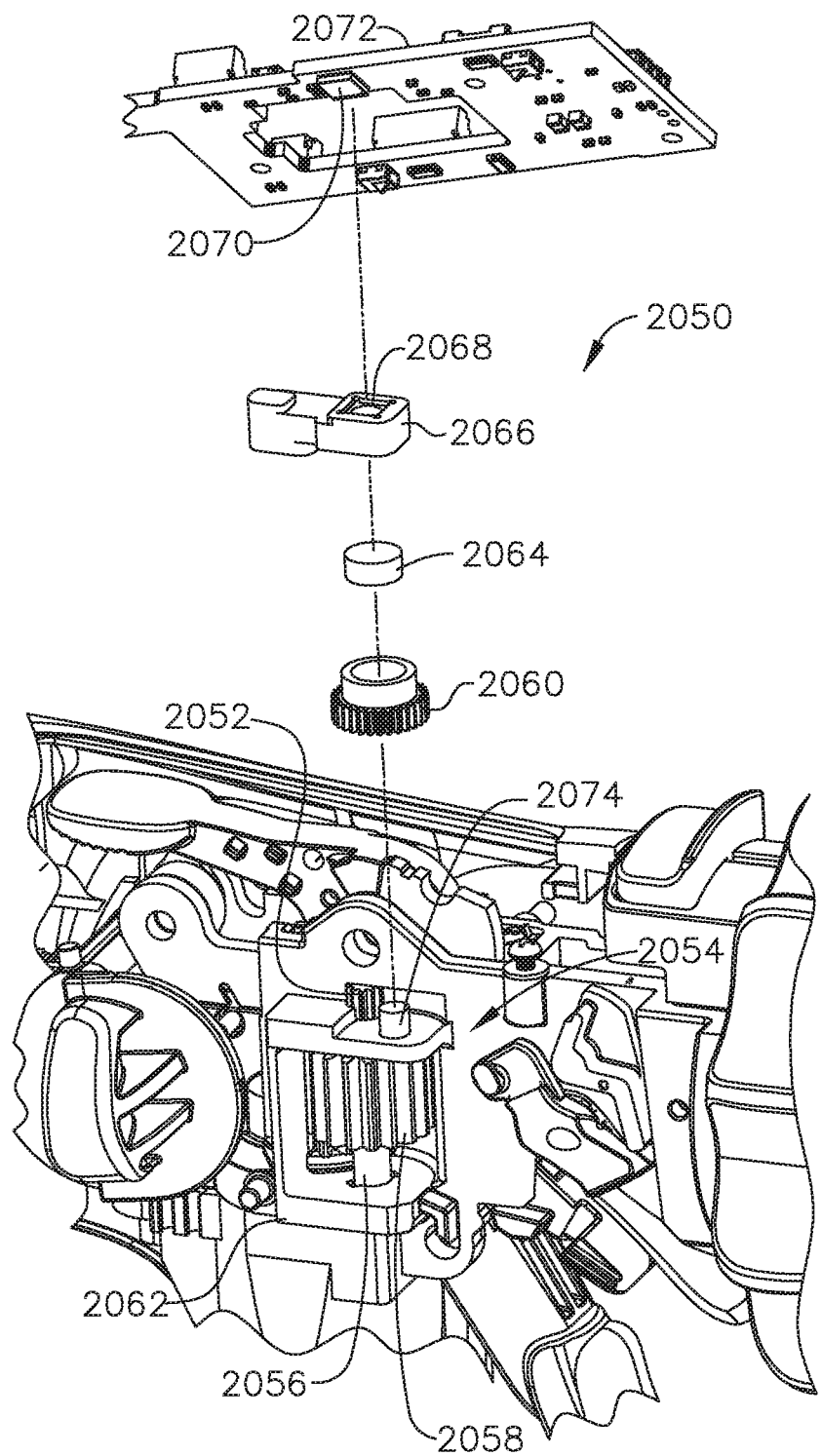
FIG. 23 is an exploded perspective view of a position sensing assembly according to one aspect of this disclosure.

In some aspects, the surgical instrument can include a sensor or sensor assembly configured to detect the position of the longitudinally movable drive member 540 (FIG. 3), knife bar 1320 (FIG. 4), knife member 1330 (FIG. 4), cutting blade 1334 (FIG. 4), and/or other components of the firing drive system 530 (FIG. 3). In various aspects, the position sensing assembly 2050 can be configured to track the linear displacement of the component of the firing drive system 530 utilizing sensors configured to track the rotation of a gear arrangement 2054 engaged with the firing drive system 530. For example, FIG. 23 is an exploded perspective view of a position sensing assembly 2050 configured to detect and track the linear position of the longitudinally movable drive member 540. In the aspect illustrated in FIG. 23, the surgical instrument comprises a drive gear 2058 that is operably driven through a drive shaft 2056 by the electric motor 505 (FIG. 1). The drive gear 2058 meshingly engages the rack of drive teeth 542 (FIG. 3) of the longitudinally movable drive member 540, thereby allowing the motor 505 to drive the linear displacement of the longitudinally movable drive member 540. Rotation of the drive gear 2058 in a first direction causes the longitudinally movable drive member 540 to advance in a distal direction and rotation of the drive gear 2058 in a second direction causes the longitudinally movable drive member 540 to retract in a proximal direction P. In various aspects, the gear arrangement 2054 of the position sensing assembly 2050 can be positioned at or adjacent to the drive gear 2058 engaged with the longitudinally movable drive member 540, as illustrated in FIG. 23. In other aspects, the gear arrangement 2054 of the position sensing assembly 2050 can be positioned downstream of the drive gear 2058 in the firing drive system 530 and/or engaged with other components of the firing drive system 530.

In the illustrated aspect, the gear arrangement 2054 of the position sensing assembly 2050 comprises a first gear 2052 that rotates about the shaft 2056 accordingly to the rotation of the drive gear 2058. Thus, rotation of the first gear 2052 about the shaft 2056 corresponds to the longitudinal translation of the longitudinally movable drive member 540 as driven by the drive gear 2058. The position sensing assembly 2050 further comprises a magnet 2064 that rotates in a manner corresponding to the rotation of the first gear 2052. In one aspect, the magnet 2064 is disposed on the first gear 2052. In this aspect, one revolution of the first gear 2052, and thus the magnet 2064, corresponds to one revolution of the drive gear 2058. In another aspect, the gear arrangement 2054 is configured to serve as a gear reducer assembly providing an alternative ratio between the number of revolutions of the drive gear 2058 and the magnet 2064. In one such aspect illustrated in FIG. 23, the gear arrangement 2054 comprises a second gear 2060, which is meshingly engaged with the first gear 2052. In this aspect, the magnet 2064 is disposed on the second gear 2060. The gear ratio connection between the first gear 2052 and the second gear 2060 can be configured such that a single revolution of the magnet 2064 corresponds to a set linear displacement of the longitudinally movable drive member 540. For example, the gear ratio connection between the first gear 2052 and the second gear 2060 can be configured such that a single revolution of the magnet 2064 can correspond to a full stroke of the longitudinally movable drive member 540. Thus, one full stroke of the longitudinally movable drive member 540 in either the distal or proximal directions corresponds to a single rotation of the second gear 2060. Since the magnet 2064 is coupled to the second gear 260, the magnet 2064 thus makes one full rotation with each full stroke of the longitudinally movable drive member 540.

The position sensing assembly 2050 further comprises a position sensor 2070 operably connected to a circuit 2072. The position sensor 2070 comprises one or more magnetic sensing elements, such as Hall effect elements, and is positioned in proximity to the magnet 2064. As the magnet 2064 rotates, the magnetic sensing elements of the position sensor 2070 determine the absolute angular position of the magnet 2064 over a revolution. In aspects of the surgical instrument wherein one revolution of the magnet 2064 corresponds to one full stroke of the longitudinally movable drive member 540, the particular angular position of the magnet 2064 thus corresponds to a particular linear position of the longitudinally movable drive member 540. In one aspect, the position sensing assembly 2050 is configured to provide a unique position signal corresponding to the location of the longitudinally movable drive member 540 according to the precise angular position of the magnet 2064 as detected by the position sensor 2070.

The position sensor 2070 can comprise any number of magnetic sensing elements, such as magnetic sensors classified according to whether they measure the total magnetic field or the vector components of the magnetic field. A series of n switches, where n is an integer greater than one, may be employed alone or in combination with gear reduction to provide a unique position signal for more than one revolution of the magnet 2064. The state of the switches can be fed back to a controller 2080 that applies logic to determine a unique position signal corresponding to the linear displacement of the longitudinally movable drive member 540.

In one aspect, the position sensor 2070 is supported by a position sensor holder 2066 defining an aperture 2068 configured to contain the position sensor 270 in precise alignment with the magnet 2064 rotating below. The magnet 2064 can be coupled to a structural element 2062, such as a bracket, that supports to gear arrangement 2054 and to the circuit 2072.

Figure 24:
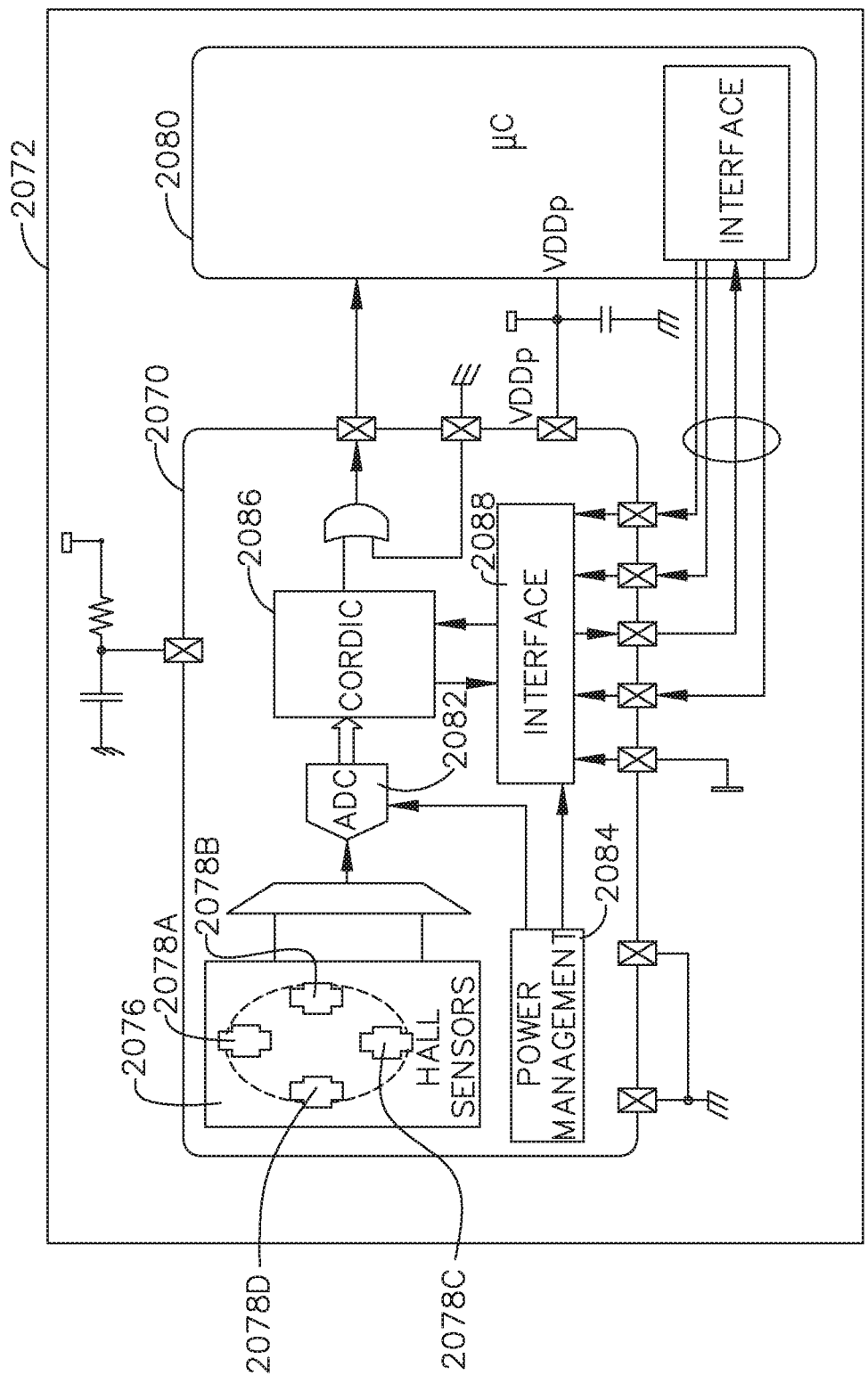
FIG. 24 is a diagram of a circuit and a position sensor of a position sensing assembly according to one aspect of this disclosure.

FIG. 24 is a diagram of a circuit 2072 and a position sensor 2070 of a position sensing assembly 2050, in accordance with one or more aspects of the present disclosure. The position sensor 2070 may be implemented as an AS5055EQFT single-chip magnetic rotary position sensor available from Austria Microsystems, AG. The position sensor 2070 is interfaced with a controller 2080, such as a microcontroller, to provide a system that is able to detect the absolute position of the longitudinally movable drive member 540 and/or other components of the firing drive system 530. In one aspect, the position sensor 2070 is a low-voltage and low-power component and includes four Hall effect elements 2078A, 2078B, 2078C, 2078D in an area 2076 of the position sensor 2070 that is located above the magnet 2064. A high-resolution ADC 2082 and a smart power management controller 2084 are also provided on the chip. A CORDIC (Coordinate Rotation Digital Computer) processor 2086, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as an SPI interface 2088, to the controller 2080. The position sensor 2070 provides 12 or 14 bits of resolution. The position sensor 2070 may be an AS5055 chip provided in a small QFN 16-pin 4×4×0.85 mm package. In the AS5055 position sensor 2070, the Hall effect elements 2078A, 2078B, 2078C, 2078D are capable producing a voltage signal that is indicative of the absolute position of the magnet 2064 in terms of the angle over a single revolution of the magnet 2064. This value of the angle, which is unique position signal, is calculated by the CORDIC processor 2086 is stored onboard the AS5055 position sensor 2070 in a register or memory. The value of the angle that is indicative of the position of the magnet 2064 over one revolution is provided to the controller 2080 in a variety of techniques, e.g., upon power up or upon request by the controller 2080.

Although the position sensor 2070 is depicted in FIG. 24 as including four Hall effect elements, in other aspects of the surgical instrument, the number of Hall effect elements included in the position sensor 2070 can vary. Generally, the number of Hall effect elements will correspond to the degree of resolution desired for the position sensor 2070 as a larger number of Hall effect elements would allow the position sensor 2070 to detect finer movements of the longitudinally movable drive member 540. In various aspects, the distance between the Hall effect elements can be uniform, i.e., the Hall effect elements can be evenly positioned, so that each Hall effect element corresponds to a set displacement distance of the longitudinally movable drive member 540. Additional aspects of the position sensing assembly 2050, the circuit 2072, and the position sensor 2070 are described in U.S. patent application Ser. No. 15/130,590, entitled SYSTEMS AND METHODS FOR CONTROLLING A SURGICAL STAPLING AND CUTTING INSTRUMENT, which is incorporated by reference in its entirety.

In other aspects, the knife bar 1320, knife member 1330, cutting blade 1334, and/or other components of the firing drive system 530 could alternatively be configured to include a rack of drive teeth that meshingly engage the gear arrangement 2054 of the position sensing assembly 2050. In such aspects of the surgical instrument, the position sensing assembly 2050 is configured to track the linear displacement of the particular component of the firing drive system 530, rather than being connected to the drive gear 2058 and/or shaft 2056 driving the displacement of the longitudinally movable drive member 540. Accordingly, it should be appreciated that the principles discussed with respect to the aspect wherein the displacement of the longitudinally movable drive member 540 is tracked are equally applicable to aspects of a position sensing assembly 2050 configured to detect the linear displacement of the knife bar 1320, knife member 1330, cutting blade 1334, and/or other components of the firing drive system 530.

In other aspects, the position sensing assembly 2050 comprises contact or non-contact linear displacement sensors configured to track the linear displacement of the firing drive system 530. The linear displacement sensors can comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable linearly arranged Hall effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

Figure 25:
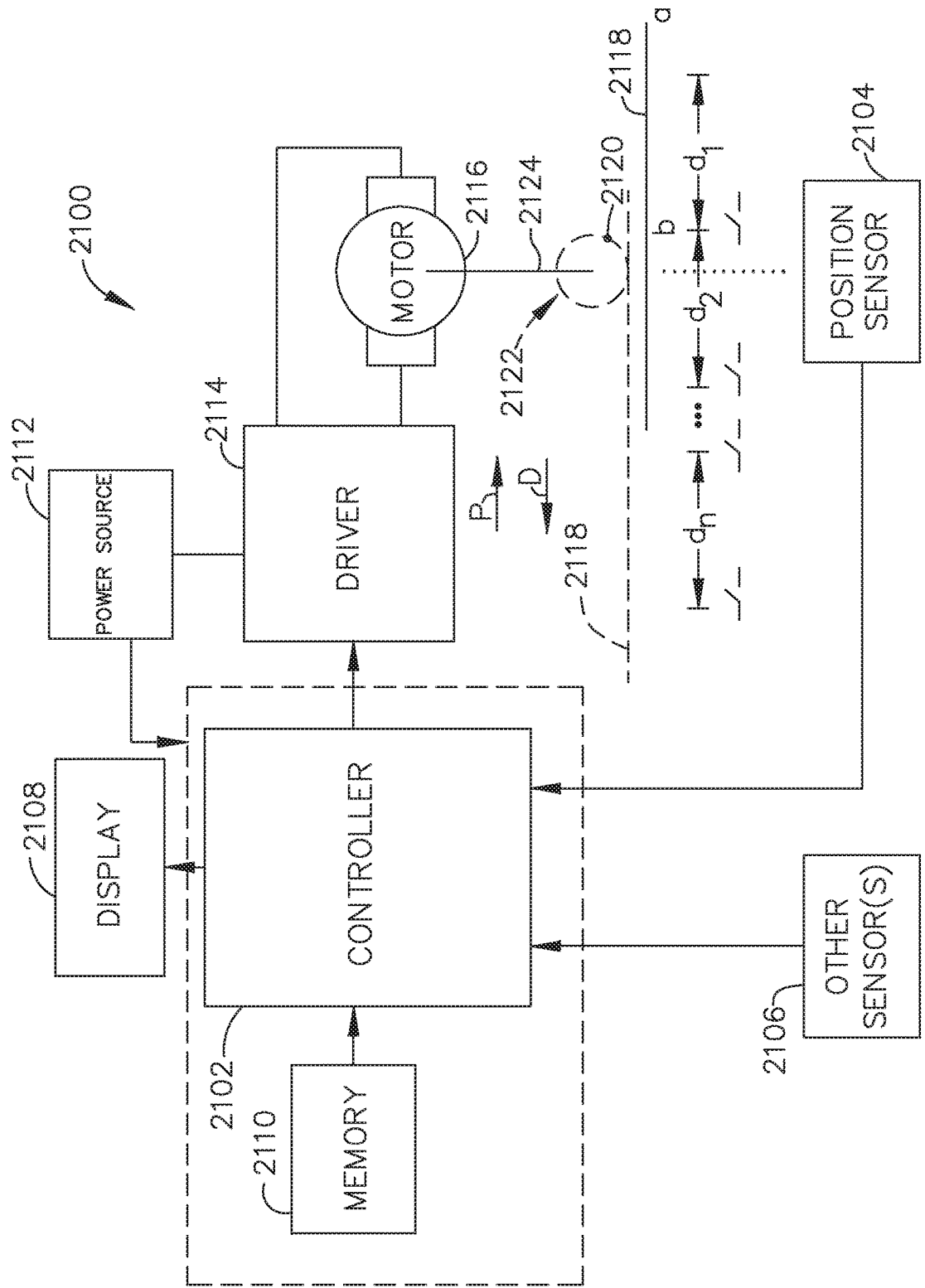
FIG. 25 is a block diagram of one example of a surgical instrument configured to display various statuses of the surgical instrument according to one aspect of this disclosure.
Figure 26:
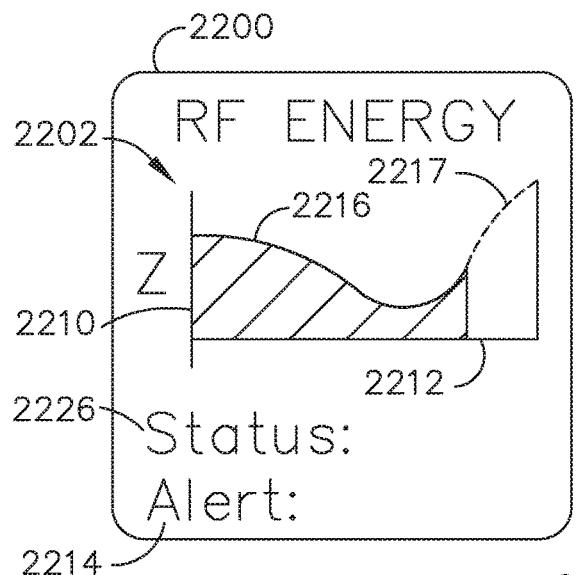
FIG. 26 is a display depicting RF energy status information of the surgical instrument according to one aspect of this disclosure.
Figure 27:
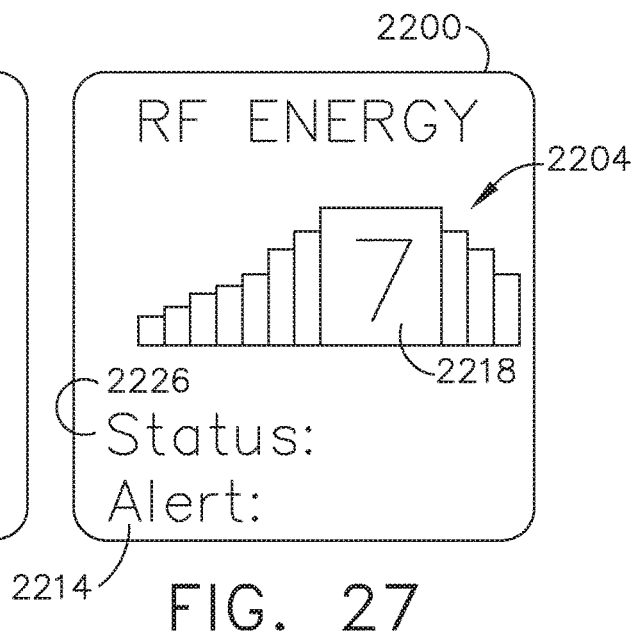
FIG. 27 is a display depicting RF energy status information of the surgical instrument according to one aspect of this disclosure.
Figure 28:
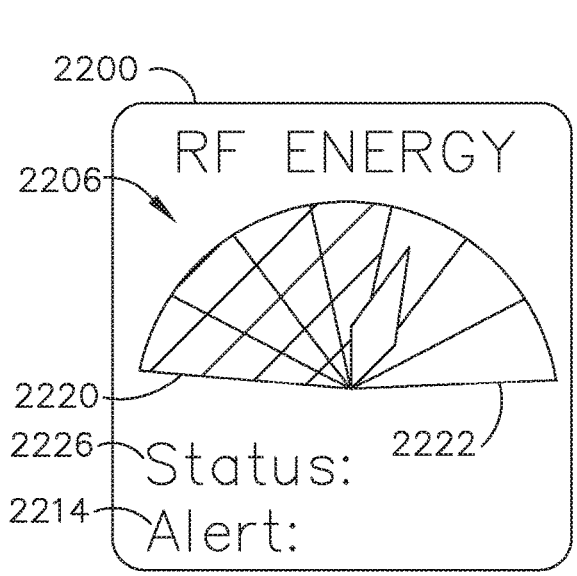
FIG. 28 is a display depicting RF energy status information of the surgical instrument according to one aspect of this disclosure.
Figure 29:
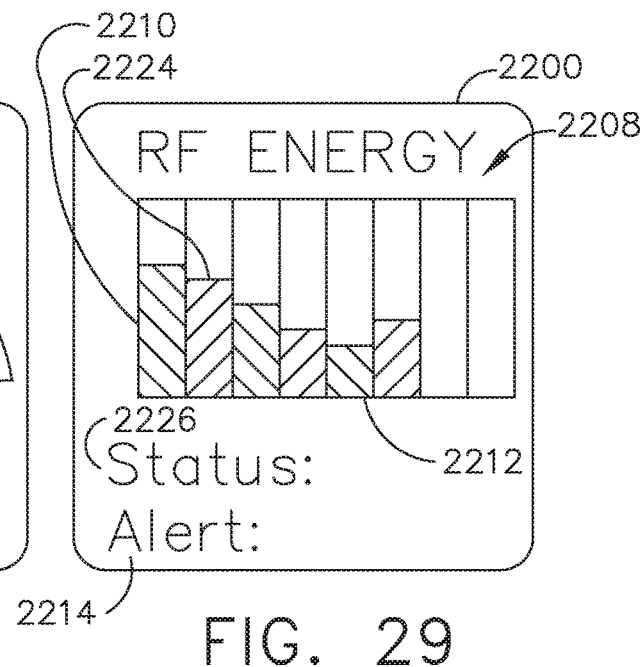
FIG. 29 is a display depicting RF energy status information of the surgical instrument according to one aspect of this disclosure.
Figure 30:
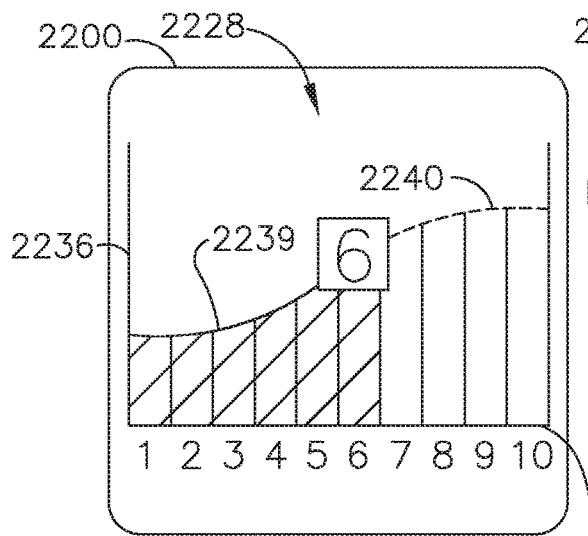
FIG. 30 is a display depicting temperature information of the surgical instrument according to one aspect of this disclosure.
Figure 31:
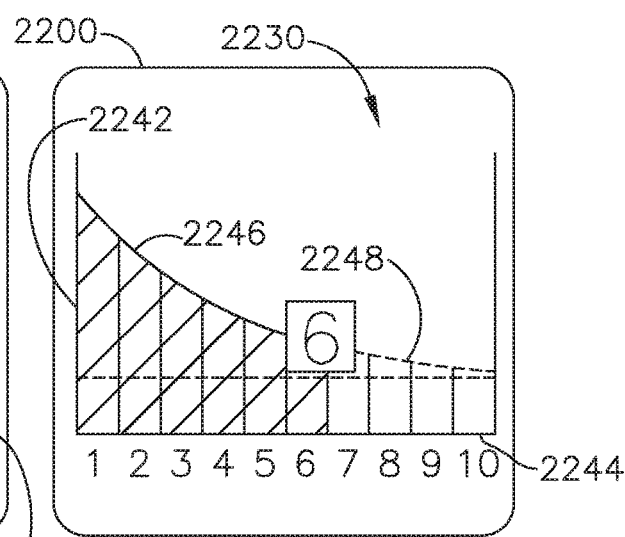
FIG. 31 is a display depicting tissue water content information of the surgical instrument according to one aspect of this disclosure.
Figure 32:
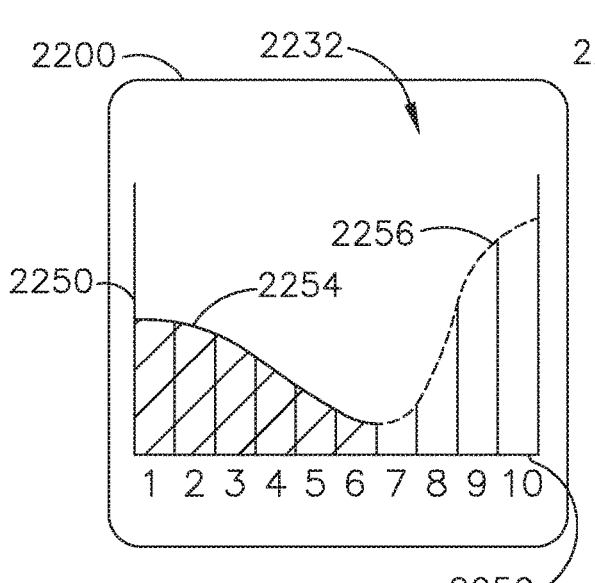
FIG. 32 is a display depicting operational progress information of the surgical instrument according to one aspect of this disclosure.
Figure 33:
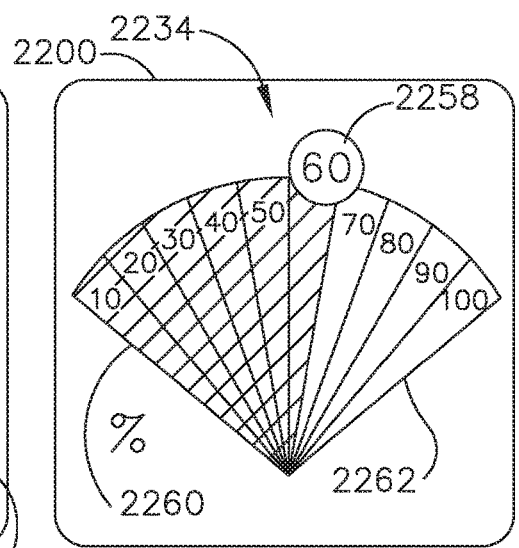
FIG. 33 is a display depicting operational progress information of the surgical instrument according to one aspect of this disclosure.
Figure 34:
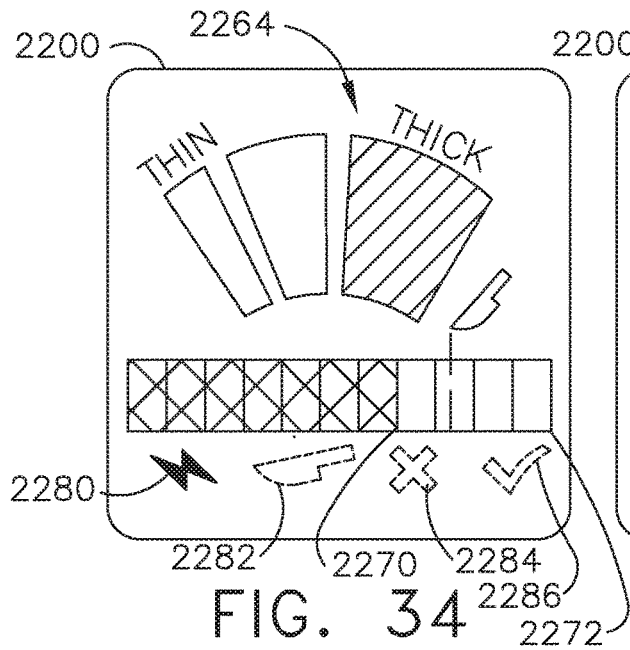
FIG. 34 is a display depicting tissue and operational progress information of the surgical instrument according to one aspect of this disclosure.

FIG. 25 is a block diagram of one example of a surgical instrument 2100 programmed to display various statuses of the surgical instrument 2100, in accordance with one or more aspects of the present disclosure. The surgical instrument 2100 comprises a controller 2102 that is operably connected to one or more sensors 2104, 2106 and a display 2108, which may be disposed on the exterior casing of the surgical instrument 2100. The controller 2102 embodies or executes a logic that controls the operation of the surgical instrument 2100 according to a variety of inputs, such as signals received from the one or more sensors 2104, 2106 with which the controller 2102 is in signal communication. In various aspects, the controller 2102 comprises a processor, such as a CPU, operably connected to a memory 2110 storing program instructions that, when executed by the processor, cause the controller 2102 and/or surgical instrument 2100 to execute a process dictated by the program instructions. In other aspects, the controller 2102 comprises a control circuit that is configured to execute a process according to digital or analog signal input. The control circuit can comprise an ASIC, a FPGA, or any other circuit that is manufacturable or programmable to execute a logic.

The controller 2102 is configured to display various statuses associated with the use of the surgical instrument 2100 on the display 2108 according to input received from a variety of sensors. One such sensor includes the position sensor 2104, which can include the position sensing assembly 2050 (FIG. 23), as described above. Other sensors 2106 from which the controller 2102 receives input can include the trigger sensing assembly 2005 (FIGS. 19-20) and the tissue thickness sensing assembly 2022 (FIGS. 21-22), as described above.

The surgical instrument 2100 further includes a motor 2116, such as an electric motor, that drives a rotatable shaft 2124, which operably interfaces with a gear assembly 2122 that is mounted in meshing engagement with a set, or rack, of drive teeth, such as in a rack and pinion arrangement, on a displacement member 2118. In the position sensing assembly 2050, the displacement member 2118 can include, for example, the longitudinally movable drive member 540 of the firing drive system 530. A sensor element or magnet 2120 can be operably coupled to a gear assembly 2122 such that a single revolution of the magnet 2120 corresponds to some linear longitudinal translation of the displacement member 2118. The position sensor 2104 can then further include a plurality of magnetic sensing elements configured to detect the angular position of the magnet 2120, which corresponds to the linear position of the displacement member 2118 and thus allows the position sensor 2104 to detect the absolute or relative position of the displacement member 2118. The position sensor 2104 can further be configured to relay a feedback signal to the controller 2102 that is indicative of the position of the displacement member 2118. A driver 2114 is operably connected to the motor 2116 and configured to provide a drive signal thereto that sets the velocity at which the motor 2116 is driven, the current drawn by the motor 2116, the voltage at which the motor 2116 is set, or a variety of other motor 2116 characteristics. A power source 2112 supplies power to any or all of the driver 2114, motor 2116, controller 2102, display 2108, sensors 2104, 2106, or other components of the surgical instrument 2100.

In some aspects, the surgical instrument 2100 can include a sensing assembly that is configured to detect the progress or advancement of the closure mechanism. In various aspects, the closure mechanism sensing assembly can comprise the trigger sensing assembly 2005 described above. As the closure trigger 512 is utilized to actuate the closure drive system 510, which in turn causes the closure shuttle 1914 (FIG. 5) to advance, the actuation or position of the closure trigger 512 can thus be detected as a proxy for the progress or advancement of the closure mechanism.

In other aspects, the closure mechanism sensing assembly can be similar to the position sensing assembly 2050 described above with respect to the firing drive system 530 and illustrated in FIGS. 23-24. The closure mechanism sensing assembly of the surgical instrument 2100 can include the position sensor 2104, which can be provided in addition to or in lieu of the position sensor described with respect to the position sensing assembly 2050. In these aspects, the displacement member 2118 can include one or more components of the closure mechanism, such as the closure shuttle 1914, proximal closure tube 1910, and/or distal closure tube 1930, comprise rack of drive teeth that are meshingly engaged with a corresponding gear assembly 2122 supporting a magnet 2120 thereon. As the displacement member 2118 of the closure mechanism advances distally or proximally, the magnet 2120 is caused to rotate in a first direction or a second direction. The position sensor 2104 further includes a plurality of magnetic sensing elements, such as Hall effect elements, that are positioned in proximity to the magnet 2120. As the magnet 2120 rotates, the magnetic sensing elements of the position sensor 2104 determine the absolute angular position of the magnet 2120 over a revolution. As the angular position of the magnet 2120 corresponds to the position of the displacement member 2118 of the closure mechanism with which the gear assembly 2122 is engaged, the closure tube sensing assembly can thus detect the absolute position of the component of the closure mechanism. Additional details regarding these aspects of the closure mechanism sensing assembly are described above with respect to the position sensing assembly 2050.

The velocity at which the knife bar 1320 is being translated by the firing drive system 530 and/or the end effector 1500 is being closed by the closure mechanism can be determined in various aspects utilizing a position sensor 2104 to track the position of a displacement member 2118 in combination with a timer or timing circuit. As the displacement member 2118 is being translated, the position sensor 2104 can determine its position $d_1, d_2, \ldots, d_n$ at a series of discrete time intervals or time stamps $t_1, t_2, \ldots, t_n$ provided by the timer. The timer can include a continuously running timer, i.e., a clock, or a timer that is initiated upon activation of either of the firing or closure mechanisms. In one aspect, for each discrete position measurement taken by the position sensor 2104, the controller 2102 accesses the timer to retrieve a time stamp according to the receipt time of the position measurement. The controller 2102 can then calculate the velocity of the displacement member 2118 over a set time period according to the change in its displacement position over time. As the velocity of the displacement member 2118 corresponds in a known manner to either the velocity at which the knife bar 1320 is translated or the velocity at which the end effector 1500 is closed, the controller 2102 can thus determine the firing or closure velocity of the surgical instrument 2100.

The other sensors 2106 can additionally include a cartridge sensor. In one aspect, the cartridge sensor includes the channel circuit 1670 (FIG. 10), which can be configured to detect the presence and/or status of an RF cartridge 1700 via the exposed contacts 1676 positioned to make electrical contact with the corresponding exposed contacts 1756 of the RF cartridge 1700. In another aspect, the cartridge sensor includes a sensor, such as the cartridge present sensor and/or cartridge condition sensor disclosed in U.S. Patent Application Pub. No. 2014/0296874, that is positioned with the elongated channel 1602 comprising electrical contacts that output a logic zero when the circuit is open and a logic one when the circuit is closed, i.e., the RF cartridge 1700 is positioned correctly within the elongated channel 1602.

The other sensors 2106 can additionally include a temperature sensor that is configured to detect the temperature of the tissue being sealed by the RF energy. In one aspect, the temperature sensor includes a temperature sensing circuit disclosed as described in U.S. Pat. No. 8,888,776, entitled ELECTROSURGICAL INSTRUMENT EMPLOYING AN ELECTRODE, which is incorporated by reference in its entirety. In this aspect, the temperature sensing circuit can be configured to apply a voltage potential that is a function of the temperature sensed by the temperature sensing circuit. The temperature sensing circuit can be configured to apply a first voltage potential to the gate terminal when it detects a first temperature, a second voltage potential when it detects a second temperature, and a third voltage potential when it detects a third temperature, and so forth. In various aspects, the temperature sensing circuit can decrease the voltage potential applied to the gate terminal as the temperature of the electrode increases. For example, the temperature sensing circuit can be configured to apply a first voltage potential to the gate terminal when a first temperature is detected by the temperature sensing circuit and, in addition, a second voltage potential, which is lower than the first voltage potential, when the temperature sensing circuit detects a second temperature which is higher than the first temperature. Correspondingly, the temperature sensing circuit can increase the voltage potential applied to the gate terminal as the temperature of the electrode decreases. The change in the voltage potential generated by the temperature sensing circuit can be detected by, for example, a circuit in order to generate a feedback signal indicative of the temperature experienced or sensed by the circuit that is then transmitted to the controller 2102. The temperature sensing circuit can be included with the first jaw 1600 (FIG. 3), the second jaw 1800 (FIG. 3), and/or the cartridge 1700 (FIG. 2). In aspects wherein the cartridge 1700 includes the temperature sensing circuit, the feedback signal generated by the temperature sensing circuit can be transmitted to the channel circuit 1670 through the electrical connection between the corresponding exposed contacts 1676, 1756. The channel circuit 1670 can then transmit the feedback signal to the controller 2102.

The other sensors 2106 can additionally include tissue sensors that are configured to measure one or more characteristics of the tissue undergoing to clamping, sealing, stapling, and/or cutting operations of the surgical instrument 2100. In one aspect, the other sensors 2106 comprise a tissue impedance sensor that is configured to measure the impedance of the clamped tissue as RF energy is applied. The tissue impedance sensor comprises, for example, electrodes and an impedance monitoring circuit that are configured to measure the current between the electrodes and/or the impedance of the tissue between the electrodes, as described in U.S. Pat. No. 5,817,093, entitled IMPEDANCE FEEDBACK MONITOR WITH QUERY ELECTRODE FOR ELECTROSURGICAL INSTRUMENT, which is incorporated by reference in its entirety. The electrodes of the tissue impedance sensor can be the same electrodes 1736R, 1736L, 1738R, 1738R for delivery of the therapeutic RF energy or different electrodes. In aspects wherein the tissue impedance sensor electrodes are different than the therapeutic electrodes, the frequency of RF energy delivered through the tissue impedance sensor electrodes can be different from the frequency of energy delivered through the therapeutic electrodes to reduce electrical interference. The tissue impedance sensor electrodes comprise at least two electrically opposite electrodes that are arranged on the end effector 1500 such that they contact the tissue clamped thereby. The tissue impedance sensor electrodes can be located either on the same surface or opposing surfaces of the end effector 1500 between a portion of the engaged tissue. As the voltage supplied to the tissue impedance sensor electrodes by, for example, the RF generator 400 (FIG. 1) is known and the current between the electrodes is detectable by the impedance monitoring circuit, the impedance of the tissue is thus calculable. In one aspect, the impedance monitoring circuit can calculate the impedance of the clamped tissue itself and then transmit a feedback signal indicative of the impedance to the controller 2102. In another aspect, the impedance monitoring circuit can transmit a feedback signal indicative of the detected current between the electrodes to the controller 2102, which then calculates the impedance of the tissue.

In totality, the various sensors or sensor assemblies disclosed herein can be utilized by the surgical instrument 2100 to monitor the position of the closure trigger 512, the advancement of the closure drive system 510 and/or components of the closure mechanism, the thickness of the clamped tissue, the position of the knife bar 1320 and/or other components of the firing drive system 530, the presence of the RF cartridge 1700, the status of the RF cartridge 1700, the closure speed of the end effector 1500, and various other operational statuses of the surgical instrument 2100. These states, parameters, positions, or other information associated with the operation of the surgical instrument 2100 can be tracked by the controller 2102 through feedback signals transmitted from the various sensing assemblies. The controller 2102 can then cause the display 2108 to display one or more of the monitored variables associated with the operation of the surgical instrument 2100 in a graphical format for viewing by the operators of the surgical instrument 2100.

FIGS. 26-39 are displays depicting various statuses, parameters, or other information associated with the operation of the surgical instrument, in accordance with one or more aspects of the present disclosure. In various aspects depicted in FIGS. 26-29, the display 2200 of the surgical instrument can be configured to graphically represent the status of the RF energy being supplied to the tissue engaged by the end effector 1500 (FIG. 1). The status of the supplied RF energy can be represented in the format of a graph 2202, a numerical value 2204, a dial 2206, or a bar graph 2208. The RF energy delivered to the tissue corresponds to the tissue impedance 2210 measured, for example, by a tissue impedance sensor, as described above. Furthermore, the tissue impedance 2210 varies as a function of time 2212 because the properties of the engaged tissue change due to the application of mechanical force from the jaws of the end effector 1500 and RF energy. One such change in the properties of the engaged tissue is the egress of water from the tissue. Another such change in the properties of the engaged tissue is the change in conductance of the tissue fibers as RF energy is applied. Therefore in some aspects, the display 2200 can be configured to depict the change in tissue impedance 2210 over time 2212 as, for example, a curve 2216 in a graph 2202 or a series of bars 2224 indicating measurements of the tissue impedance 2210 at discrete time intervals in a bar graph 2208. The display 2200 can additionally be configured to depict an expected curve 2217 of the impedance 2210 over time 2212 that is calculated by the controller 2102 according to an algorithm executed thereby. In other aspects, the display 2200 can represent the tissue impedance 2210 as a numeral 2218. The numeral 2218 can represent the absolute value of the measured impedance in, for example, ohms. Alternatively, the numeral 2218 can represent the relative value or ratio of the measured impedance between a maximum and minimum impedance value. Furthermore, the size that the numeral 2218 is depicted on the display 2200 can correspond to the relative size of the value. The dial 2206 format of the display 2200 can likewise depict the measured tissue impedance relative to a maximum impedance 2222 and a minimum impedance 2220.

The display 2200 can also be configured to depict one or more alerts 2214 or statuses 2226 according to the operation of the surgical instrument 2100. The alerts 2214 can include warnings that the tissue impedance has exceeded a maximum tissue impedance, that the electrodes have lost energy, that the measured tissue impedance is deviating from an expected tissue impedance as calculated by the controller 2102 or stored on the memory 2110, and that the application time of the RF energy has exceeded a maximum or expected time. The statuses 2226 can include the current or subsequent stage or step of the process of using the surgical instrument 2100.

In addition to displaying the RF energy being supplied to the tissue, the display 2200 can also be configured to depict a variety of other parameters, statuses, or other information as determined by the sensing assemblies in communication with the controller 2102. In one aspect, the display 2200 can be configured to depict a temperature status 2228 of the tissue to which RF energy is being applied. The temperature can be determined by, for example, a temperature sensing circuit, as described above. In various aspects, the temperature status 2228 can be depicted as an absolute value of the measured temperature or a relative value of the measured temperature between a minimum and maximum temperature. In one aspect, the temperature status 2228 can be depicted as a curve 2239 of the absolute or relative temperature 2236 as a function of time 2238. The display 2200 can additionally be configured to depict an expected curve 2240 of the temperature 2236 over time 2238 that is calculated by the controller 2102 according to an algorithm executed thereby.

In another aspect, the display 2200 can be configured to depict the water content status 2230 of the tissue. The water content of the tissue can be determined, for example, as a function of the change in impedance of the tissue during the clamping and RF sealing operations executed by the surgical instrument 2100. As the change in mechanical properties of a particular tissue type over time are experimentally known and the change in tissue impedance as a result of the change in tissue mechanical properties is likewise experimentally known, the controller 2102 can isolate these effects from the measured change in tissue impedance over time, calculate the change in tissue water content, and then cause the display 2200 to depict the calculated water content status 2230. As described above with respect to other tissue or surgical instrument parameters, the display 2200 can depict the tissue water content status 2230 in the format of a graph, a numeral, a dial, or any other such graphical representation. In one aspect, the display 2200 can depict the change in tissue water content 2242 over time 2244 as a curve 2246. The display 2200 can additionally be configured to depict an expected curve 2248 of the water content 2242 over time 2244 that is calculated by the controller 2102 according to an algorithm executed thereby.

In other aspects, the display 2200 can be configured to depict the seal completion status 2232 or completion status 2234 according to the operation of the surgical instrument 2100. The seal completion status 2232 can correspond, for example, to the RF energy status depicted in FIGS. 26-29 and indicate the currently measured delivery of RF energy relative to an expected value. For example, in FIG. 32 the seal completion status 2232 is depicted graphically as a measured curve 2254 of the tissue impedance 2250 over time 2252 as compared to an expected curve 2256 of the tissue impedance 2250 over time 2252. The ratio between the measured curve 2254 and the expected curve 2256 graphically depicts the relative progress of the application of RF energy relative to an expected progress, which can be determined experimentally and stored on the memory 2110 to be accessed by the controller 2102. In one aspect, the completion status 2234 can represent the seal completion status in an alternative graphical format. In another aspect, the completion status 2234 can represent the percentage of number of steps executed or completed by the surgical instrument 2100 or the percentage completion of any individual step, such as the advancement of the closure mechanism or the current longitudinal displacement of the knife bar 1320 (FIG. 4) relative to the total longitudinal displacement thereof in the step of firing the knife bar 1320. The current progress can be tracked by the controller 2102 in combination with the various sensing assemblies of the surgical instrument 2100. The completion status 2234 can be displayed in the format of a dial depicting a percentage 2258 between a minimum percentage 2260 and a maximum percentage 2262.

In various aspects depicted in FIGS. 34-37, the display 2200 can be configured to display the thickness of the tissue engaged by the end effector 1500, the advancement of a displacement member, such as the knife bar 1320, and various statuses associated with the tissue thickness and/or the displacement member. The thickness of the tissue engaged by the end effector 1500 can be detected, e.g., by a tissue thickness sensing assembly 2022 in communication with the controller 2102, as described above. In various aspects, the controller 2102 can cause the display 2200 to depict the tissue thickness according to the feedback signal generated by the tissue thickness sensing assembly 2202 as either an absolute or a relative value in a variety of different graphical formats, such as a series of discrete zones 2264 ranging from thin to thick, as a graph 2266, or as a dial 2268, among others.

Figure 35:
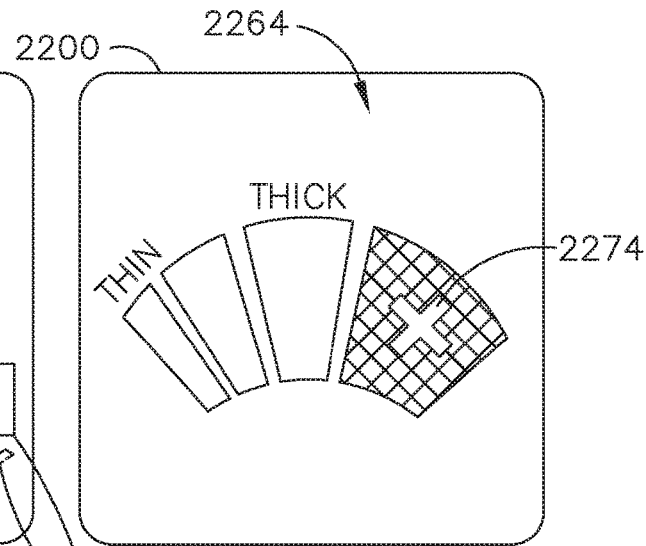
FIG. 35 is a display depicting a warning of the surgical instrument according to one aspect of this disclosure.
Figure 36:
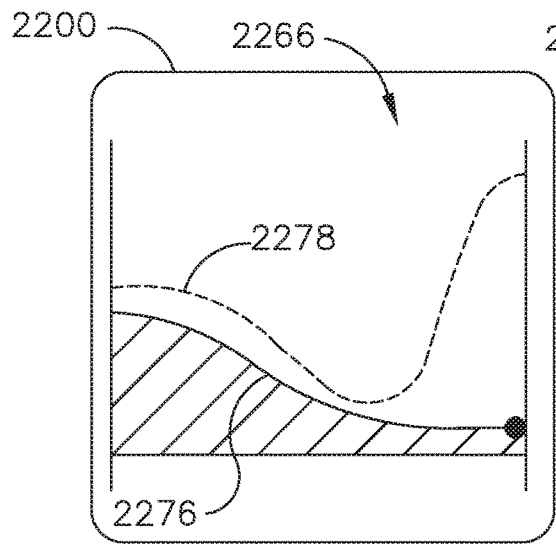
FIG. 36 is a display depicting a warning of the surgical instrument according to one aspect of this disclosure.
Figure 37:
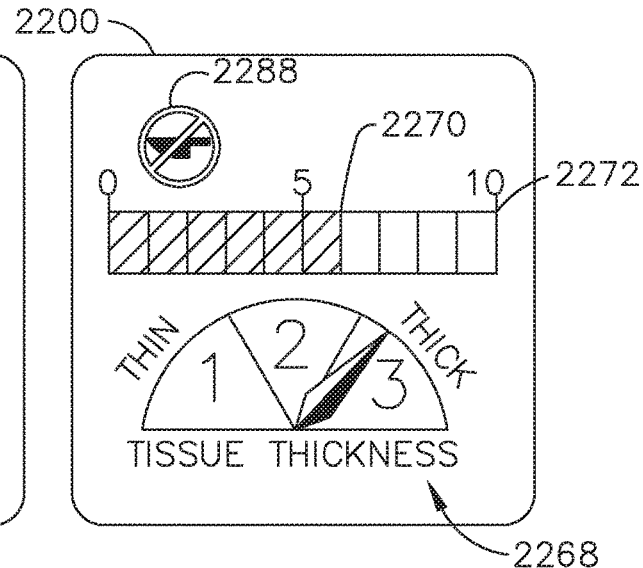
FIG. 37 is a display depicting status, operational progress, and tissue information of the surgical instrument according to one aspect of this disclosure.
Figure 38:
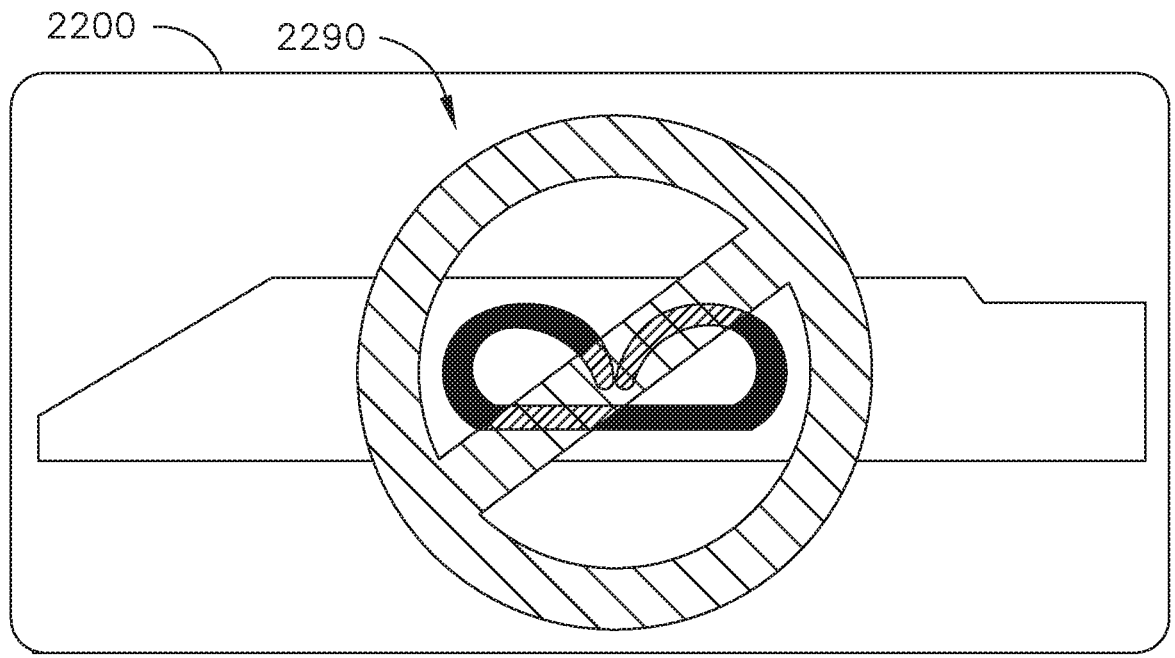
FIG. 38 is a display depicting RF cartridge status information of the surgical instrument according to one aspect of this disclosure.
Figure 39:
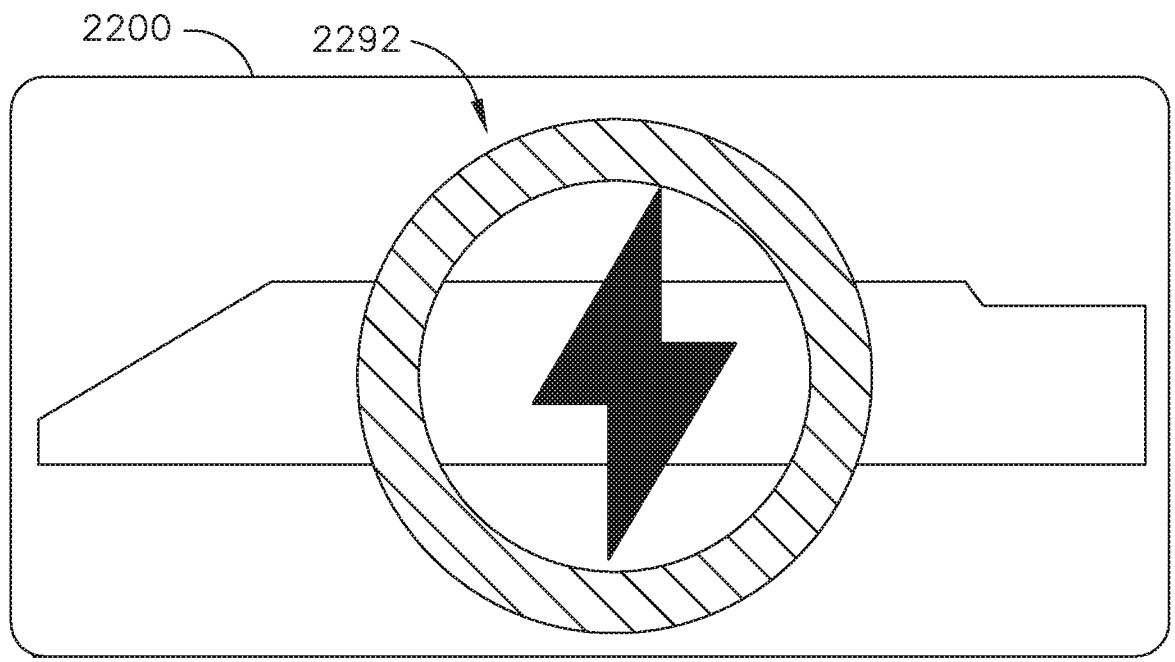
FIG. 39 is a display depicting RF cartridge status information of the surgical instrument according to one aspect of this disclosure.

The display 2200 can additionally comprise alerts to provide graphical warnings to users that the tissue is too thick or too thin for a particular operation. For example, an alert can comprise an icon 2274, such as an "X" as depicted in FIG. 35, that is overlaid on the display 2200 to indicate to the operator that the surgical instrument 2100 is currently or will be operating outside of desired conditions. In other aspects, the icon 2274 may or may not be overlaid on the various graphical formats 2264, 2266, 2268 indicating tissue thickness. Various other graphical warnings can be utilized, including icons of different designs, changes in color, or textual warnings. As another example, an alert can comprise a graphical depiction that a curve 2276 of the tissue thickness, displacement member velocity, or other parameter measured by or calculated from the various sensing assemblies is deviating from an expected curve 2278. In such aspects, various other additional alerts can accompany the depicted alert, such as textual alerts, icons, changes in color, and the like.

In one aspect, the display 2200 can additionally be configured to depict the position of the knife bar 1320. The position of the knife bar 1320 can be detected by, for example, a position sensing assembly 2050 in communication with the controller 2102, as described above. In various aspects, the controller 2102 can cause the display 2200 to depict the knife bar 1320 displacement according to the feedback signal generated by the position sensing assembly 2050 as, for example, a linear measured position 2270 of the knife bar 1320 relative to a maximum position 2272 thereof. The maximum position 2272 can include a maximum incision length desired for a particular surgical operation or an absolute maximum length that the knife bar 1320 can translate.

In another aspect, the display 2200 can additionally be configured to depict the advancement or status of the closure mechanism. The advancement of the closure mechanism can be detected, e.g., by a closure trigger sensing assembly 2005 in communication with the controller 2102, as discussed above, or a position sensing assembly 2050 configured to detect a position of a displacement member 2118 of the closure mechanism, as described above with respect to FIG. 25. In various aspects, the controller 2102 can cause the display 2200 to depict the closure mechanism advancement according to the feedback signal generated by the trigger sensing assembly 2005 or the position sensing assembly 2050 as, for example, a detected position of the closure shuttle 1914 relative to a maximum position thereof.

In some aspects, the controller 2102 can be configured to populate the display 2200 with a variety of icons when certain events or statuses occur. For example, a first icon 2280 can indicate that RF energy is currently or has been successfully applied to the tissue. A second icon 2282 can indicate that the knife bar 1320 is currently or has been successfully fired. A third icon 2284 can indicate that an error has occurred at some point during the operation of the instrument. A fourth icon 2286 can indicate that all of the steps of the operation of the instrument have been successfully completed. A fifth icon 2288 can indicate that an error has occurred with a specific component of the instrument, such as the knife bar 1320. The display 2200 can additionally be configured to display any other such type of icon indicating that a step or process is complete or that an event has occurred, such as an error. The various icons can be configured to illuminate, become visible, or change color when the status is active or the event has occurred.

In some aspects, the display 2200 can be configured to indicate whether a correct or incorrect cartridge type has been loaded into the end effector 1500, i.e., inserted into the elongate channel 1602 (FIG. 10). The channel circuit 1670 can be configured to read or detect the type of cartridge that is received by the end effector 1500 via a sensor or electrical communication between the channel circuit 1670 and the cartridge. In one aspect, the cartridges comprise a memory storing an identifier or value indicative of the cartridge type that is transmitted to the channel circuit 1670 upon the cartridge being inserted into the elongate channel 1602 of the end effector 1500. The channel circuit 1670, which is communicably coupled to the controller 2102, is configured to then transmit the cartridge type identifier or value to the controller 2102. The logic executed by the controller 2102 can then compare the cartridge type to the expected cartridge type. If the cartridge type and the expected cartridge type do not match, then the controller 2102 can cause the display 2200 to depict a first icon 2290. If the cartridge type and the expected cartridge type do match, then the controller 2102 can cause the display 2200 to depict a second icon 2292. In the aspect depicted in FIGS. 38-39, the first icon 2290 corresponds to a staple cartridge being inserted when an RF cartridge is expected and the second icon 2292 corresponds to an RF cartridge being inserted when an RF cartridge is expected.

The various aspects of the display 2200 depicted in FIGS. 26-39 can represent individual representations of a screen displayed to an operator or portions of a screen displayed to an operator. In various aspects, operators can switch between the various screens via user input or the controller 2102 can automatically adjust the display 2200 according to the operation of the surgical instrument 2100. In various aspects, the display 2200 can include a graphical user interface that can be manipulated via, for example, a capacitive touchscreen.

The display 2200 as described herein can include one or more screens disposed on or connected with the surgical instrument for graphically displaying information captured by the various sensing assemblies. In one aspect, the display 2200 comprises a single screen positioned on the exterior casing of the surgical instrument, as depicted in FIG. 1. In aspects utilizing multiple screens, the screens can be positioned adjacently to each other or separately from each other. The display 2200 can be positioned directly on the surgical instrument, can be removably connectable to the surgical instrument such that the display 2200 is brought into signal communication with the controller when connected to the surgical instrument, or can be otherwise associated with the surgical instrument.

The functions or processes of monitoring various statuses of the surgical instrument via various sensing assemblies described herein may be executed by any of the processing circuits, either individually or in combination, described herein, such as the onboard circuit board 1152 described in connection with FIGS. 5 and 15, the channel circuit 1670 described in connection with FIG. 10, the flexible circuit assemblies 1730L, 1730R described in connection with FIGS. 10-13, the controller 2080 described in connection with FIG. 24, and the controller 2102 described in connection with FIG. 25.

Aspects of the surgical instrument may be practiced without the specific details disclosed herein. Some aspects have been shown as block diagrams rather than detail. Parts of this disclosure may be presented in terms of instructions that operate on data stored in a computer memory. Generally, aspects described herein which can be implemented, individually and/or collectively, by a wide range of hardware, software, firmware, or any combination thereof can be viewed as being composed of various types of "electrical circuitry." Consequently, "electrical circuitry" includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer or processor configured by a computer program, which at least partially carries out processes and/or devices described herein), electrical circuitry forming a memory device (e.g., forms of random access memory), and/or electrical circuitry forming a communications device (e.g., a modem, communications switch, or optical-electrical equipment). These aspects may be implemented in analog or digital form, or combinations thereof.

The foregoing description has set forth aspects of devices and/or processes via the use of block diagrams, flowcharts, and/or examples, which may contain one or more functions and/or operation. Each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), Programmable Logic Devices (PLDs), circuits, registers and/or software components, e.g., programs, subroutines, logic and/or combinations of hardware and software components, logic gates, or other integrated formats. Some aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

The mechanisms of the disclosed subject matter are capable of being distributed as a program product in a variety of forms, and that an illustrative aspect of the subject matter described herein applies regardless of the particular type of signal bearing medium used to actually carry out the distribution. Examples of a signal bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a electrical conductor communications link, a electrical conductorless communication link (e.g., transmitter, receiver, transmission logic, reception logic, etc.).

The foregoing description of these aspects has been presented for purposes of illustration and description. It is not intended to be exhaustive or limiting to the precise form disclosed. Modifications or variations are possible in light of the above teachings. These aspects were chosen and described in order to illustrate principles and practical application to thereby enable one of ordinary skill in the art to utilize the aspects and with modifications as are suited to the particular use contemplated. It is intended that the claims submitted herewith define the overall scope.

EXAMPLES

Various aspects of the subject matter described herein are set out in the following examples:

Example 1. A surgical instrument comprising: a circuit configured to deliver RF energy to a cartridge disposed in an end effector configured to receive the cartridge; a closure mechanism configured to transition the end effector between an open position and a closed position; a display; and a control circuit operably coupled to the display, the control circuit configured to: determine an amount of RF energy delivered to a tissue through the cartridge; display the amount of RF energy on the display; determine a position of the closure mechanism; and display the position of the closure mechanism on the display.

Example 2. The surgical instrument of Example 1, wherein the control circuit is configured to receive a signal from an impedance sensor configured to measure an impedance of the tissue disposed between a first electrode and a second electrode, wherein the control circuit is configured to determine the amount of RF energy delivered to the tissue according to the impedance of the tissue.

Example 3. The surgical instrument of one or more of Example 1 through Example 2, wherein the control circuit is configured to receive a signal from a position sensor configured to detect a position of a displacement member of the closure mechanism, wherein the control circuit is configured to determine the position of the closure mechanism according to the position of the displacement member.

Example 4. The surgical instrument of one or more of Example 1 through Example 3, further comprising: a closure trigger configured to drive the closure mechanism between a first position and a second position; and a closure trigger sensor configured to detect a position of the closure trigger; wherein the control circuit is configured to determine the position of the closure mechanism according to the position of the closure trigger.

Example 5. The surgical instrument of one or more of Example 1 through Example 4, wherein the control circuit is configured to receive a signal from a sensor configured to detect a position of the end effector between the open position and the closed position, wherein the control circuit is configured to determine the position of the closure mechanism according to the position of the end effector.

Example 6. The surgical instrument of one or more of Example 1 through Example 5, wherein the control circuit is configured to receive a signal from a cartridge sensor configured to detect a cartridge type of the cartridge received by the end effector, wherein the control circuit is configured to display whether the cartridge type matches an expected cartridge type on the display.

Example 7. A surgical instrument comprising: a circuit configured to deliver RF energy to a cartridge disposed in an end effector; a closure mechanism configured to transition the end effector between an open position and a closed position; a display; and a processor operably coupled to the display; a memory operably coupled to the processor, the memory storing program instructions that, when executed by the processor, cause the processor to: determine a status of RF energy delivered to a tissue through the cartridge; display the status of RF energy; determine a status of the closure mechanism; and display the status of the closure mechanism.

Example 8. The surgical instrument of Example 7, wherein the memory stores program instructions that when executed by the processor, cause the processor to receive a signal from an impedance sensor configured to measure an impedance of the tissue between a first electrode and a second electrode, wherein the processor is configured to determine the status of RF energy applied to the tissue according to the impedance of the tissue.

Example 9. The surgical instrument of Example 7, wherein the memory stores program instructions that when executed by the processor, cause the processor to receive a signal from a position sensor configured to detect a position of a displacement member of the closure mechanism, wherein the processor is configured to determine the status of the closure mechanism according to the position of the displacement member.

Example 10. The surgical instrument of one or more of Example 7 through Example 9, further comprising: a closure trigger configured to drive the closure mechanism between a first position and a second position; and a closure trigger sensor configured to detect a position of the closure trigger; wherein the surgical instrument determines the status of the closure mechanism according to the position of the closure trigger.

Example 11. The surgical instrument of one or more of Example 7 through Example 10, wherein the memory stores program instructions that when executed by the processor, cause the processor to receive a signal from a sensor configured to detect a position of the end effector between the open position and the closed position, wherein the processor is configured to determine the status of the closure mechanism according to the position of the end effector.

Example 12. The surgical instrument of one or more of Example 7 through Example 11, wherein the memory further stores program instructions that when executed by the processor, cause the processor to receive a signal from a cartridge sensor configured to detect a cartridge type of the cartridge received by the end effector, wherein the processor is configured to display whether the cartridge type matches an expected cartridge type on the display.

Example 13. A method of controlling a display in a surgical instrument, the surgical instrument comprising a circuit configured to deliver RF energy to a cartridge disposed within an end effector configured to receive the cartridge, a closure mechanism configured to transition the end effector between an open position and a closed position, a display, and a control circuit coupled to the display, the method comprising: determining, by the control circuit, an amount of RF energy applied to a tissue through the cartridge; displaying, by the control circuit, the amount of RF energy on the display; determining, by the control circuit, a position of the closure mechanism; and displaying, by the control circuit, the position of the closure mechanism on the display.

Example 14. The method of Example 13, further comprising: measuring, by an impedance sensor, an impedance of the tissue between a first electrode and a second electrode:

wherein the control circuit determines the amount of RF energy applied to the tissue according to the impedance of the tissue.

Example 15. The method of one or more of Example 13 through Example 14, further comprising: detecting, by a position sensor, a position of a displacement member of the closure mechanism; wherein the control circuit determines the position of the closure mechanism according to the position of the displacement member.

Example 16. The method of one or more of Example 13 through Example 15, further comprising: detecting, by a closure trigger sensor, a position of a closure trigger configured to drive the closure mechanism between a first position and a second position; wherein the control circuit determines the position of the closure mechanism according to the position of the closure trigger.

Example 17. The method of one or more of Example 13 through Example 16, further comprising: detecting, by a sensor, a position of the end effector between the open position and the closed position: wherein the control circuit determines the position of the closure mechanism according to the position of the end effector.

Example 18. The method of one or more of Example 13 through Example 17, further comprising: detecting, by a cartridge sensor, a cartridge type of the cartridge received by the end effector; and displaying, by the control circuit, whether the cartridge type matches an expected cartridge type on the display.

The invention claimed is:

1. A surgical instrument comprising:
a handle assembly;
a circuit configured to deliver RF energy to a cartridge disposed in an end effector configured to receive the cartridge;
a closure mechanism configured to transition the end effector between an open position and a closed position;
a display located on the handle assembly for displaying information about a monitored parameter to a user of the surgical instrument; and
a control circuit operably coupled to the display, the control circuit configured to:
receive a signal from an impedance sensor configured to measure an impedance of a tissue disposed between a first electrode and a second electrode;
determine an amount of RF energy delivered to the tissue through the cartridge according to the impedance of the tissue;
display the amount of RF energy delivered to the tissue on the display;
display an alert on the display when the measured tissue impedance deviates from an expected tissue impedance;
determine a position of the closure mechanism; and
display the position of the closure mechanism on the display,
wherein the control circuit is further configured to:
determine a thickness of the tissue disposed between the first electrode and the second electrode;
display the thickness of the tissue on the display; and
provide a warning to the user responsive to determining that the thickness of the tissue is greater than a first thickness and/or lower than a second thickness.

2. The surgical instrument of claim 1, wherein the control circuit is configured to receive a signal from a position sensor configured to detect a position of a displacement member of the closure mechanism, wherein the control circuit is configured to determine the position of the closure mechanism according to the position of the displacement member.

3. The surgical instrument of claim 1, further comprising:
a closure trigger configured to drive the closure mechanism between a first position and a second position; and
a closure trigger sensor configured to detect a position of the closure trigger;
wherein the control circuit is configured to determine the position of the closure mechanism according to the position of the closure trigger.

4. The surgical instrument of claim 1, wherein the control circuit is further configured to display the measured tissue impedance with respect to time.

5. The surgical instrument of claim 1, wherein the control circuit is further configured to:
determine a water content status of the tissue disposed between the first electrode and the second electrode; and
display the water content status on the display.

6. The surgical instrument of claim 1, wherein the amount of RF energy is displayed as a graphical representation on the display.

7. The surgical instrument of claim 1, wherein the control circuit is further configured to:
display an alert on the display when the measured impedance exceeds a maximum tissue impedance.

8. A surgical instrument, comprising:
a handle assembly;
a circuit configured to deliver RF energy to a cartridge disposed in an end effector configured to receive the cartridge;
a closure mechanism configured to transition the end effector between an open position and a closed position;
a display located on the handle assembly for displaying information about a monitored parameter to a user of the surgical instrument; and
a control circuit operably coupled to the display, the control circuit configured to:
determine an amount of RF energy delivered to a tissue through the cartridge;
display the amount of RF energy delivered to the tissue on the display;
determine a position of the closure mechanism, wherein the control circuit is configured to receive a signal from a sensor configured to detect a position of the end effector as the end effector is transitioned between the open position and the closed position, wherein the control circuit is configured to determine the position of the closure mechanism according to the position of the end effector; and
display the position of the closure mechanism on the display,
wherein the control circuit is further configured to:
determine a thickness of the tissue disposed between a first electrode and a second electrode;
display the thickness of the tissue on the display; and
provide a warning to the user responsive to determining that the thickness of the tissue is greater than a first thickness and/or lower than a second thickness.

9. The surgical instrument of claim 1, wherein the control circuit is configured to receive a signal from a cartridge sensor configured to detect a cartridge type of the cartridge received by the end effector, wherein the control circuit is configured to display whether the cartridge type matches an expected cartridge type on the display.

10. A surgical instrument comprising:
a handle assembly;
a circuit configured to deliver RF energy to a cartridge disposed in an end effector;
a closure mechanism configured to transition the end effector between an open position and a closed position;
a display located on the handle assembly for displaying information about a monitored parameter to a user of the surgical instrument; and
a processor operably coupled to the display;
a memory operably coupled to the processor, the memory storing program instructions that, when executed by the processor, cause the processor to:
receive a signal from an impedance sensor configured to measure an impedance of a tissue positioned between a first electrode and a second electrode;
compare the measured tissue impedance to an expected tissue impedance;
determine a status of RF energy delivered to the tissue through the cartridge according to the measured tissue impedance;
display the status of RF energy on the display, wherein the status of RF energy comprises an alert when the measured tissue impedance deviates from the expected tissue impedance;
determine a status of the closure mechanism; and
display the status of the closure mechanism on the display,
wherein the memory further stores program instructions that, when executed by the processor, cause the processor to:
determine a thickness of the tissue disposed between the first electrode and the second electrode;
display the thickness of the tissue on the display; and
provide a warning to the user responsive to determining that the thickness of the tissue is greater than a first thickness and/or lower than a second thickness.

11. The surgical instrument of claim 10, wherein the memory stores program instructions that when executed by the processor, cause the processor to receive a signal from a position sensor configured to detect a position of a displacement member of the closure mechanism, wherein the processor is configured to determine the status of the closure mechanism according to the position of the displacement member.

12. The surgical instrument of claim 10, further comprising:
a closure trigger configured to drive the closure mechanism between a first position and a second position; and
a closure trigger sensor configured to detect a position of the closure trigger;
wherein the surgical instrument determines the status of the closure mechanism according to the position of the closure trigger.

13. The surgical instrument of claim 10, wherein the memory stores program instructions that when executed by the processor, cause the processor to receive a signal from a sensor configured to detect a position of the end effector between the open position and the closed position, wherein the processor is configured to determine the status of the closure mechanism according to the position of the end effector.

14. The surgical instrument of claim 10, wherein the memory further stores program instructions that when executed by the processor, cause the processor to receive a signal from a cartridge sensor configured to detect a cartridge type of the cartridge received by the end effector, wherein the processor is configured to display whether the cartridge type matches an expected cartridge type on the display.

15. A method of controlling a display in a surgical instrument, the surgical instrument comprising a handle assembly, a circuit configured to deliver RF energy to a cartridge disposed within an end effector configured to receive the cartridge, a closure mechanism configured to transition the end effector between an open position and a closed position, a display located on the handle assembly for displaying information about a monitored parameter to a user of the surgical instrument, and a control circuit coupled to the display, the method comprising:
measuring, by an impedance sensor, an impedance of a tissue between a first electrode and a second electrode;
determining, by the control circuit, an amount of RF energy applied to the tissue through the cartridge according to the impedance of the tissue;
displaying, by the control circuit, the amount of RF energy on the display;
displaying an alert on the display when the measured impedance exceeds a maximum tissue impedance;
determining, by the control circuit, a position of the closure mechanism;
displaying, by the control circuit, the position of the closure mechanism on the display,
determining, by the control circuit, a thickness of the tissue disposed between the first electrode and the second electrode;
displaying, by the control circuit, the thickness of the tissue on the display; and
providing, by the control circuit, a warning to the user responsive to determining that the thickness of the tissue is greater than a first thickness and/or lower than a second thickness.

16. The method of claim 15, further comprising:
detecting, by a position sensor, a position of a displacement member of the closure mechanism;
wherein the control circuit determines the position of the closure mechanism according to the position of the displacement member.

17. The method of claim 15, further comprising:
detecting, by a closure trigger sensor, a position of a closure trigger configured to drive the closure mechanism between a first position and a second position;
wherein the control circuit determines the position of the closure mechanism according to the position of the closure trigger.

18. The method of claim 15, further comprising:
detecting, by a sensor, a position of the end effector between the open position and the closed position:
wherein the control circuit determines the position of the closure mechanism according to the position of the end effector.

19. The method of claim 15, further comprising:
detecting, by a cartridge sensor, a cartridge type of the cartridge received by the end effector; and
displaying, by the control circuit, whether the cartridge type matches an expected cartridge type on the display.

* * * * *